United States Patent
Kim et al.

(10) Patent No.: US 11,849,595 B2
(45) Date of Patent: Dec. 19, 2023

(54) NEAR-INFRARED ABSORBERS, NEAR-INFRARED ABSORBING/BLOCKING FILMS AND PHOTOELECTRIC DEVICES AND ORGANIC SENSORS AND ELECTRONIC DEVICES

(71) Applicant: Samsung Electronics Co., Ltd., Suwon-si (KR)

(72) Inventors: Hwang Suk Kim, Suwon-si (KR); Ohkyu Kwon, Seoul (KR); Bum Woo Park, Hwaseong-si (KR); Kwang Hee Lee, Hwaseong-si (KR); Dong-Seok Leem, Seongnam-si (KR); Hyesung Choi, Seoul (KR); Dongseon Lee, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 385 days.

(21) Appl. No.: 16/944,873

(22) Filed: Jul. 31, 2020

(65) Prior Publication Data
US 2021/0036251 A1   Feb. 4, 2021

(30) Foreign Application Priority Data
Aug. 2, 2019 (KR) .................. 10-2019-0094525

(51) Int. Cl.
| C07D 285/14 | (2006.01) |
| C07D 293/10 | (2006.01) |
| H10K 30/20 | (2023.01) |
| H10K 30/87 | (2023.01) |
| H10K 85/10 | (2023.01) |

(52) U.S. Cl.
CPC ............ H10K 30/20 (2023.02); C07D 285/14 (2013.01); C07D 293/10 (2013.01); H10K 30/87 (2023.02); H10K 85/111 (2023.02)

(58) Field of Classification Search
CPC .......................... C07D 285/14; C07D 293/10
See application file for complete search history.

(56) References Cited

U.S. PATENT DOCUMENTS

2018/0142153 A1   5/2018   Kirsch et al.

FOREIGN PATENT DOCUMENTS

| CN | 101885837 A | 11/2010 |
| JP | 2008-057569 A | 3/2008 |
| JP | 2018-006700 A | 1/2018 |
| KR | 10-2018-0002824 A | 1/2018 |

OTHER PUBLICATIONS

Qian, Gang et al., "Synthesis and Application of Thiadiazoloquinoxaline-Containing Chromophores as Dopants for Efficient Near-Infrared Organic Light-Emitting Diodes", J. Phys. Chem., vol. 113, No. 4, pp. 1589-1595, 2009.

Qi, Ji et al., "Highly Stable Organic Small Molecular Nanoparticles as an Advanced and Biocompatible Phototheranostic Agent of Tumor in Living Mice", ACS Nano, vol. 11, pp. 7177-7188, 2017.

Primary Examiner — Shawquia Jackson
(74) Attorney, Agent, or Firm — Harness, Dickey & Pierce, P.L.C.

(57) ABSTRACT

A near-infrared absorber includes a compound represented by Chemical Formula 1. A near-infrared absorbing/blocking film, a photoelectric device, an organic sensor, and an electronic device may include the near-infrared absorber.

[Chemical Formula 1]

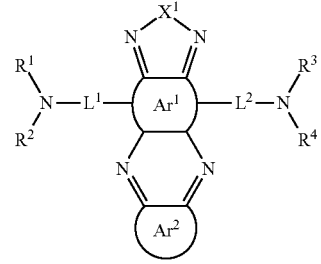

In Chemical Formula 1, $Ar^1$, $Ar^2$, $X^1$, $L^1$, $L^2$, $R^1$, $R^2$, $R^3$, and $R^4$ are the same as defined in the detailed description.

23 Claims, 14 Drawing Sheets

NEAR-INFRARED ABSORBERS, NEAR-INFRARED ABSORBING/BLOCKING FILMS AND PHOTOELECTRIC DEVICES AND ORGANIC SENSORS AND ELECTRONIC DEVICES

CROSS-REFERENCE TO RELATED APPLICATION

This application claims priority to and the benefit of, under 35 U.S.C. § 119, Korean Patent Application No. 10-2019-0094525 filed in the Korean Intellectual Property Office on Aug. 2, 2019, the entire contents of which are incorporated herein by reference.

BACKGROUND

1. Field

A near-infrared (NIR) absorber, a near-infrared absorbing/blocking film, a photoelectric device, an organic sensor, and an electronic device are disclosed.

2. Description of the Related Art

An imaging device is used in a digital camera and a camcorder, etc., to capture an image and to store it as an electrical signal, and the imaging device includes a sensor separating incident light according to a wavelength and converting each component to an electrical signal.

Recently, photoelectric devices in the near-infrared region for improving sensitivity of a sensor in a low-illumination environment or for use as a biometric device have been studied.

SUMMARY

Some example embodiments provide a near-infrared absorber having improved near-infrared light absorption characteristics.

Some example embodiments provide a film including the near-infrared absorber.

Some example embodiments provide a photoelectric device including the near-infrared absorber.

Some example embodiments provide an organic sensor including the near-infrared absorber or the photoelectric device.

Some example embodiments provide an electronic device including the photoelectric device or the organic sensor.

According to some example embodiments, a near-infrared absorber including a compound represented by Chemical Formula 1 is provided.

[Chemical Formula 1]

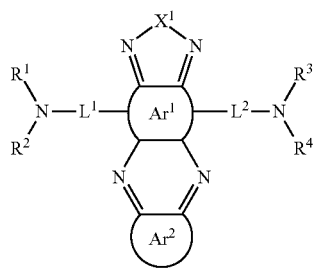

In Chemical Formula 1, $A^1$ is a substituted or unsubstituted C6 to C30 aromatic ring, a substituted or unsubstituted C3 to C30 heteroaromatic ring, or a combination thereof, $Ar^2$ is a substituted or unsubstituted C6 to C30 aromatic ring, a substituted or unsubstituted C3 to C30 heteroaromatic ring, or a combination thereof, $X^1$ is O, S, Se, Te, S(=O), S(=O$_2$), NR$^a$, CR$^b$R$^c$, or SiR$^d$R$^e$ (wherein R$^a$, R$^b$, R$^c$, and R$^d$ are independently hydrogen, a C1 to C6 alkyl group, a C1 to C6 haloalkyl group, a C6 to C12 aryl group, a C3 to C12 heteroaryl group, a halogen, a cyano group, or a combination thereof), $L^1$ and $L^2$ are independently a substituted or unsubstituted C3 to C20 heteroarylene group or a fused ring of a substituted or unsubstituted C6 to C20 arylene group and a substituted or unsubstituted C3 to C20 heteroarylene group, $R^1$, $R^2$, $R^3$, and $R^4$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C3 to C30 heteroaryl group, a substituted or unsubstituted silyl group, a halogen, or a combination thereof, and $R^1$ and $R^2$ may independently be present or be linked to each other to form a ring, and $R^3$ and $R^4$ may independently be present or be linked to each other to form a ring.

In Chemical Formula 1, $A^1$ may be benzene, a substituted or unsubstituted naphthalene, a substituted or unsubstituted anthracene, a substituted or unsubstituted phenanthrene, a substituted or unsubstituted tetracene, or a substituted or unsubstituted pyrene.

In Chemical Formula 1, $A^1$ may be a substituted or unsubstituted quinoline, a substituted or unsubstituted isoquinoline, a substituted or unsubstituted quinoxaline, a substituted or unsubstituted quinazoline, or a substituted or unsubstituted phenanthroline.

In Chemical Formula 1, $A^1$ may be one of the moieties represented by Chemical Formula A-1.

[Chemical Formula A-1]

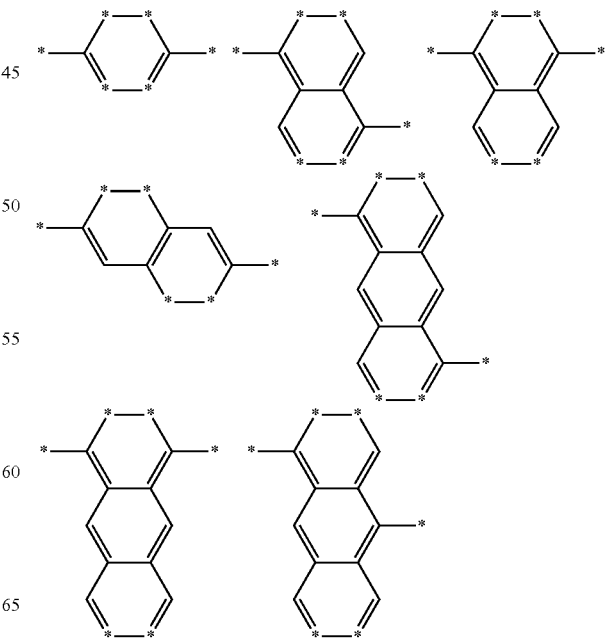

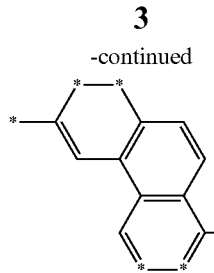

In Chemical Formula A-1, hydrogen of each aromatic ring may be replaced by a halogen, a cyano group, a C1 to C10 alkyl group, a C1 to C10 haloalkyl group, a silyl group, or a C1 to C10 alkylsilyl group, *'s inside the aromatic ring are linking portions with an N—$X^1$—N-containing pentagonal ring and an N-containing hexagonal ring, and *'s of the left and right linking groups are portions linked to $L^1$ and $L^2$ of Chemical Formula 1.

In Chemical Formula 1, $A^1$ may be one of the moieties represented by Chemical Formula A-2.

[Chemical Formula A-2]

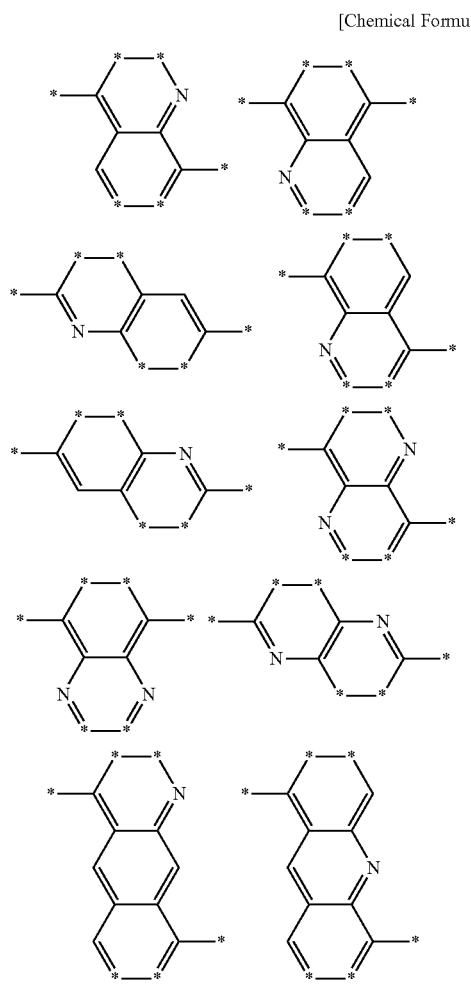

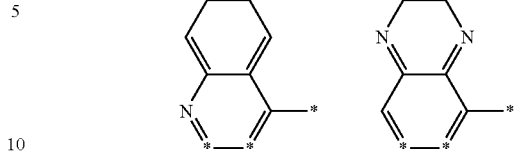

In Chemical Formula A-2, hydrogen of each aromatic ring may be replaced by a halogen, a cyano group, a C1 to C10 alkyl group, a C1 to C10 haloalkyl group, a silyl group, or a C1 to C10 alkylsilyl group, *'s inside the aromatic ring are linking portions with an N—$X^1$—N-containing pentagonal ring and an N-containing hexagonal ring, and *'s of the left and right linking groups are portions linked to $L^1$ and $L^2$ of Chemical Formula 1.

In Chemical Formula 1, Ar¹ may be a substituted or unsubstituted benzene, a substituted or unsubstituted naphthalene, a substituted or unsubstituted acenaphthene, a substituted or unsubstituted anthracene, a substituted or unsubstituted phenanthrene, a substituted or unsubstituted tetracene, or a substituted or unsubstituted pyrene.

In Chemical Formula 1, $Ar^2$ may be a substituted or unsubstituted quinoline, a substituted or unsubstituted isoquinoline, a substituted or unsubstituted quinoxaline, a substituted or unsubstituted quinazoline, a substituted or unsubstituted phenanthroline, a substituted or unsubstituted pyrimidine, or a substituted or unsubstituted benzodithiophene.

In Chemical Formula 1, $Ar^2$ may be one of the moieties represented by Chemical Formula B-1.

[Chemical Formula B-1]

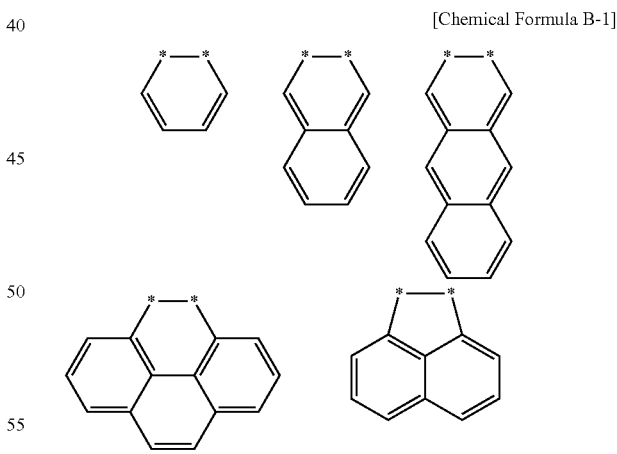

In Chemical Formula B-1, hydrogen of each aromatic ring may be replaced by a halogen, a cyano group, a C1 to C10 alkyl group, a C1 to C10 haloalkyl group, —$SiH_3$, a C1 to C10 alkylsilyl group, a C6 to C20 aryl group, or a C3 to C20 heteroaryl group, and *'s inside the aromatic ring are linking portions with the N-containing hexagonal ring of Chemical Formula 1.

In Chemical Formula 1, $Ar^2$ may be one of the moieties represented by Chemical Formula B-2.

[Chemical Formula B-2]

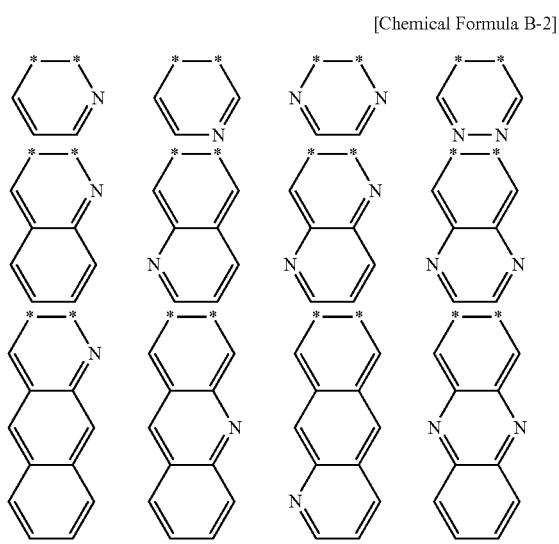

In Chemical Formula B-2,
hydrogen of each aromatic ring may be replaced by a halogen, a cyano group, a C1 to C10 alkyl group, a C1 to C10 haloalkyl group, —$SiH_3$, a C1 to C10 alkylsilyl group, a C6 to C20 aryl group, or a C3 to C20 heteroaryl group, and *'s inside the aromatic ring are linking portions with the N-containing hexagonal ring of Chemical Formula 1.

In Chemical Formula 1, Are may be one of the moieties represented by Chemical Formula B-3a or Chemical Formula B-3b.

[Chemical Formula B-3a]

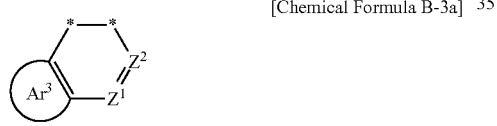

In Chemical Formula B-3a,
$Z^1$ and $Z^2$ are independently N or $CR^a$ (wherein $R^a$ is hydrogen, a C1 to C6 alkyl group, a C1 to C10 haloalkyl group, —$SiH_3$, a C1 to C10 alkylsilyl group, —$NH_2$, a C1 to C10 alkylamine group, a C6 to C12 aryl group, a C3 to C12 heteroaryl group, a halogen, a cyano group, or a combination thereof), $Ar^3$ is a substituted or unsubstituted C6 to C30 arene group or a substituted or unsubstituted C3 to C30 heteroarene group, and

*'s inside the aromatic ring are linking portions with the N-containing hexagonal ring of Chemical Formula 1,

[Chemical Formula B-3b]

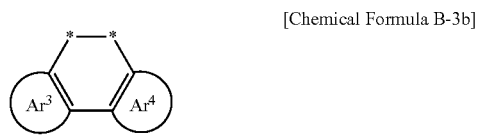

wherein, in Chemical Formula B-3b,
$Ar^3$ and $Ar^4$ are independently a substituted or unsubstituted C6 to C30 arene group or a substituted or unsubstituted C3 to C30 heteroarene group, and

*'s inside the aromatic ring are linking portions with the N-containing hexagonal ring of Chemical Formula 1.

The moiety represented by Formula B-3a may be represented by Chemical Formula B-3aa, and the moiety represented by Chemical Formula B-3b may be represented by Chemical Formula B-3bb.

[Chemical Formula B-3aa]

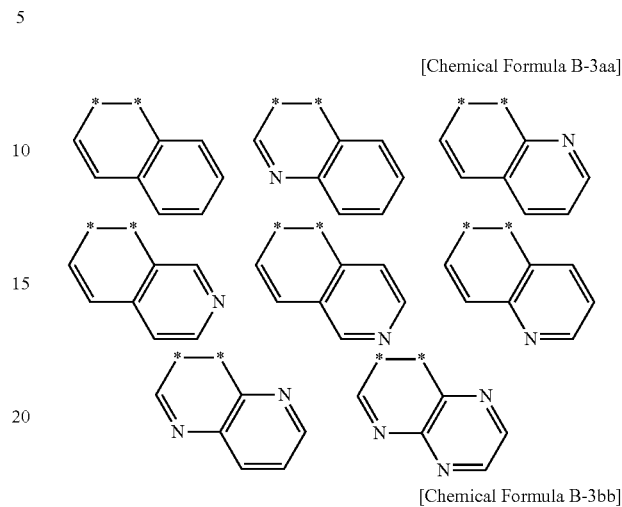

[Chemical Formula B-3bb]

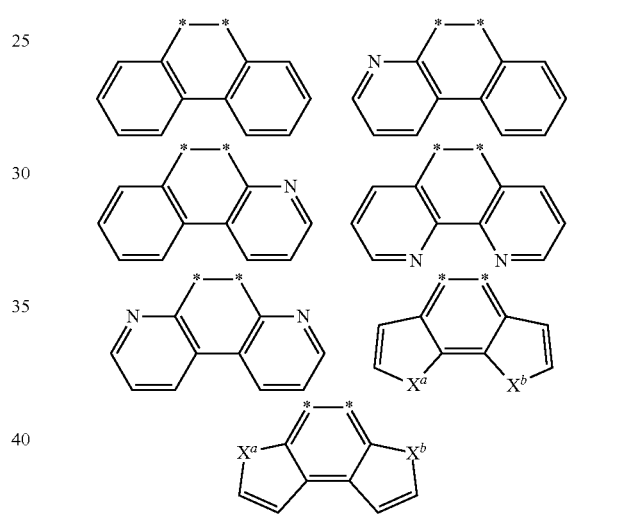

In Chemical Formulas B-3aa and B-3bb,
hydrogen of each aromatic ring may be replaced by a halogen, a cyano group, a C1 to C10 alkyl group, a C1 to C10 haloalkyl group, —$SiH_3$, a C1 to C10 alkylsilyl group, a C6 to C20 aryl group, or a C3 to C20 heteroaryl group,

*'s inside the aromatic ring are linking portions with the N-containing hexagonal ring of Chemical Formula 1, and $X^a$ and $X^b$ are independently —O—, —S—, —Se—, —Te—, —$NR^a$—, —$SiR^bR^c$—, or —$GeR^dR^e$— (wherein $R^a$, $R^b$, $R^c$, $R^d$, and $R^e$ are independently hydrogen, a halogen, a substituted or unsubstituted C1 to C10 alkyl group, or a substituted or unsubstituted C6 to C10 aryl group).

In Chemical Formula 1, $L^1$ and $L^2$ may be the same or different and may be selected from Chemical Formulas C-1 to C-4.

(C-1)

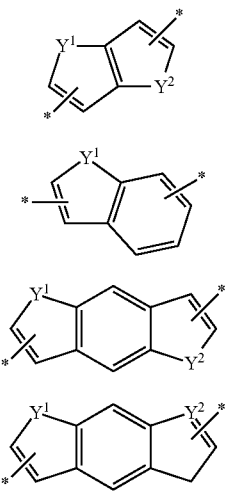

(C-2)
(C-3)
(C-4)
(C-5)

In Chemical Formulas C-1 to C-4, $Y^1$ and $Y^2$ are independently O, S, Se, Te, S(=O), S(=O)$_2$, NR$^a$, or SiR$^b$R$^c$ (wherein R$^a$, R$^b$, and R$^c$ are independently hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof), R$^b$ and R$^c$ are independently present or linked to each other to form a ring, and

* is a linking point with Chemical Formula 1.

In Chemical Formula 1, *—N(R$^1$)(R$^2$) and *—N(R$^3$)(R$^4$) may be independently represented by Chemical Formula D-1 or D-2.

[Chemical Formula D-1]

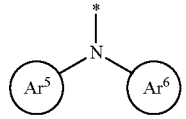

In Chemical Formula D-1,

Ar$^5$ and Ar$^6$ are independently a substituted or unsubstituted C6 to C30 aryl group or a substituted or unsubstituted C3 to C30 heteroaryl group, and

* is a linking point with Chemical Formula 1,

[Chemical Formula D-2]

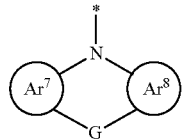

In Chemical Formula D-2,

Ar$^7$ and Ar$^8$ are independently a substituted or unsubstituted C6 to C30 arene group or a substituted or unsubstituted C3 to C30 heteroarene group, G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))— (wherein R$^a$, R$^b$, R$^c$, R$^d$, R$^e$, R$^f$, R$^g$, R$^h$, and R$^i$ are independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a ring, and n of —(CR$^f$R$^g$)$_n$— is an integer of 1 or 2), and

* is a linking point with Chemical Formula 1.

Chemical Formula D-1 may be represented by Chemical Formula D-1a or D-1b.

[Chemical Formula D-1a]

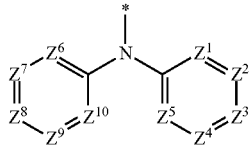

In Chemical Formula D-1a, $Z^1$ to $Z^{10}$ are independently N or CR$^a$ (wherein R$^a$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof), when $Z^1$ to $Z^{10}$ are CR$^a$, R$^a$'s may independently be present or two adjacent groups of $Z^1$ to $Z^{10}$ may be linked to each other to form a 5-membered aromatic ring or a 6-membered aromatic ring, and

* is a linking point with Chemical Formula 1.

[Chemical Formula D-1b]

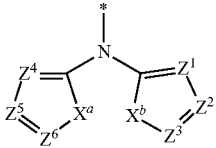

In Chemical Formula D-1b,

X$^a$ and X$^b$ are independently —O—, —S—, —Se—, —Te—, —NR$^a$—, —SiR$^b$R$^b$—, or —GeR$^d$R$^e$— (wherein R$^a$, R$^b$, R$^c$, R$^d$, and R$^e$ are independently hydrogen, a halogen, a substituted or unsubstituted C1 to C10 alkyl group, or a substituted or unsubstituted C6 to C10 aryl group), $Z^1$ to $Z^6$ are independently N or CR$^x$ (wherein R$^x$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof), when $Z^1$ to $Z^6$ are CR$^a$, R$^a$'s may independently be present or two adjacent groups of $Z^1$ to $Z^6$ may be linked to each other to form a 5-membered aromatic ring or a 6-membered aromatic ring, and

* is a linking point with Chemical Formula 1.

Chemical Formula D-2 may be represented by Chemical Formula D-2a, Chemical Formula D-2b, or Chemical Formula D-2c.

[Chemical Formula D-2a]

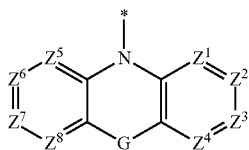

In Chemical Formula D-2a,

G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))— (wherein R$^a$, R$^b$, R$^c$, R$^d$, R$^e$, R$^f$, R$^g$, R$^h$, and R$^i$ are independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a ring, and n of —(CR$^f$R$^g$)$_n$— is an integer of 1 or 2), $Z^1$ to $Z^8$ are independently N or CR$^x$ (wherein R$^x$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof), when $Z^1$ to $Z^8$ are CR$^x$, R$^x$ may independently be present or two adjacent groups of $Z^1$ to $Z^8$ may be linked to each other to form a 5-membered aromatic ring or a 6-membered aromatic ring, and

* is a linking point with Chemical Formula 1.

[Chemical Formula D-2b]

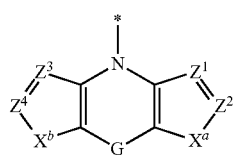

[Chemical Formula D-2c]

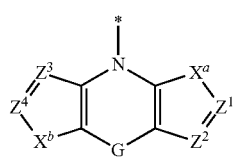

In Chemical Formula D-2b and Chemical Formula D-2c,

G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))— (wherein R$^a$, R$^b$, R$^c$, R$^d$, R$^e$, R$^f$, R$^g$, R$^h$, and R$^i$ are independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a ring, and n of —(CR$^f$R$^g$)$_n$— is an integer of 1 or 2), $X^a$ and $X^b$ are independently —O—, —S—, —Se—, —Te—, —NR$^p$—, —SiR$^q$R$^r$— or —GeR$^s$R$^t$— (wherein R$^p$, R$^q$, R$^r$, R$^s$, and R$^t$ are independently hydrogen, a halogen, a substituted or unsubstituted C1 to C10 alkyl group, or a substituted or unsubstituted C6 to C10 aryl group), $Z^1$ to $Z^4$ are independently N or CR$^x$ (wherein R$^x$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof), and when $Z^1$ to $Z^4$ are CR$^x$, R$^x$'s may independently be present or two adjacent groups of $Z^1$ to $Z^6$ may be linked to each other to form a 5-membered aromatic ring or a 6-membered aromatic ring.

A peak absorption wavelength of the near-infrared absorber may be in a wavelength region of about 750 nm to about 3000 nm.

According to some example embodiments, a near-infrared absorbing/blocking film including the near-infrared absorber is provided.

According to some example embodiments, a photoelectric device includes a first electrode and a second electrode facing each other, and an active layer between the first electrode and the second electrode, wherein the active layer includes a near-infrared absorber including the compound represented by Chemical Formula 1.

According to some example embodiments, an active layer including the photoelectric device is provided.

According to some example embodiments, an electronic device including the photoelectric device or the organic sensor is provided.

According to some example embodiments, a photoelectric device includes a first electrode and a second electrode facing each other; an active layer between the first electrode and the second electrode; and a charge auxiliary layer between the active layer and the first electrode, or the active layer and the second electrode, wherein the charge auxiliary layer includes a near-infrared absorber that includes the compound represented by Chemical Formula 1.

The active layer may further include the near-infrared absorber.

According to some example embodiments, an organic sensor may include a semiconductor substrate; a first photoelectric device on the semiconductor substrate and configured to selectively absorb light in a first near-infrared wavelength region; and an additional sensor configured to selectively absorb light in a separate wavelength region that is different from the first near-infrared wavelength region. The first photoelectric device may include a near-infrared absorber that includes the compound represented by Chemical Formula 1.

The additional sensor may be an infrared light sensor at least partially embedded within the semiconductor substrate, and the separate wavelength region may be a separate near-infrared wavelength region that is different from the first near-infrared wavelength region. The first photoelectric device and the infrared light sensor may overlap in a vertical direction that is perpendicular to a top surface of the semiconductor substrate.

The additional sensor may include a plurality of photodiodes at least partially embedded within the semiconductor substrate, the plurality of photodiodes configured to selectively absorb light in separate visible wavelength regions. The first photoelectric device and the plurality of photodiodes may overlap in a vertical direction that is perpendicular to a top surface of the semiconductor substrate.

The organic sensor may further include an additional photoelectric device on the semiconductor substrate, the additional photoelectric device being between the first photoelectric device and the semiconductor substrate, the additional photoelectric device configured to selectively absorb light in an additional wavelength region that is different from the first near-infrared wavelength region and the separate visible wavelength regions.

The additional sensor may include at least one additional photoelectric device vertically stacked between the first photoelectric device and the semiconductor substrate, each separate photoelectric device of the at least one additional photoelectric device including a separate photoelectric conversion layer and configured to selectively absorb light in a respective wavelength region that is different from the first near-infrared wavelength region.

The first photoelectric device may include a first electrode and a second electrode facing each other; and an active layer between the first electrode and the second electrode. The active layer may include the near-infrared absorber.

The first photoelectric device may include a first electrode and a second electrode facing each other; an active layer between the first electrode and the second electrode; and a charge auxiliary layer between the active layer and the first electrode, or the active layer and the second electrode. The charge auxiliary layer may include the near-infrared absorber.

The near-infrared absorber may exhibit good absorbing properties in the near-infrared region and thus, may be effectively used in photoelectric devices and/or organic sensors.

DETAILED DESCRIPTION

Figure 1:
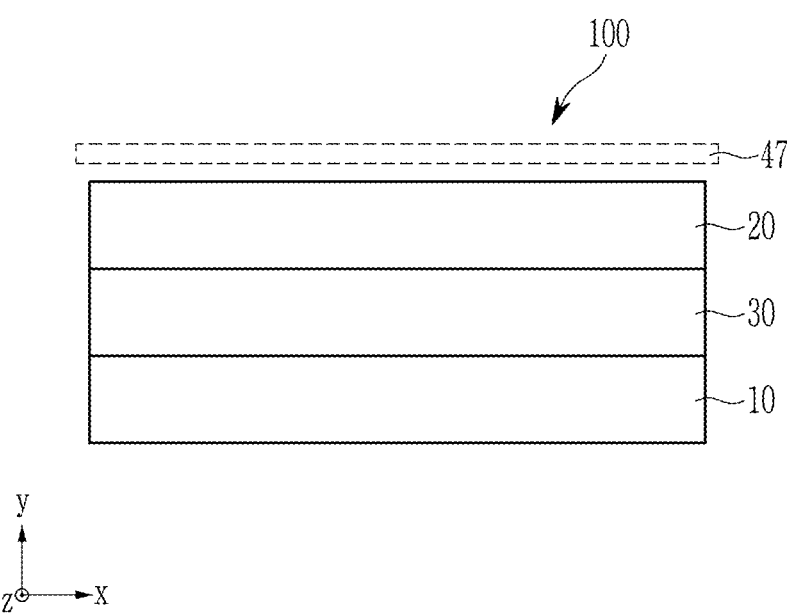
FIG. 1 is a cross-sectional view showing a photoelectric device according to some example embodiments.

Hereinafter, example embodiments will hereinafter be described in detail, and may be easily performed by a person having an ordinary skill in the related art. However, this disclosure may be embodied in many different forms and is not to be construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present. It will further be understood that when an element is referred to as being "on" another element, it may be above or beneath the other element.

It will be understood that elements and/or properties thereof may be recited herein as being "the same" or "equal" as other elements, and it will be further understood that elements and/or properties thereof recited herein as being "the same" as or "equal" to other elements may be "the same" as or "equal" to or "substantially the same" as or "substantially equal" to the other elements and/or properties thereof. Elements and/or properties thereof that are "substantially the same" as or "substantially equal" to other elements and/or properties thereof will be understood to include elements and/or properties thereof that are the same as or equal to the other elements and/or properties thereof within manufacturing tolerances and/or material tolerances. Elements and/or properties thereof that are the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

In the drawings, parts having no relationship with the description are omitted for clarity of the embodiments, and the same or similar constituent elements are indicated by the same reference numeral throughout the specification.

Hereinafter, "combination" includes a mixture of two or more, inter-substitution, and a laminate structure of two or more.

As used herein, when specific definition is not otherwise provided, "substituted" refers to replacement of a hydrogen of a compound or a functional group by a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a silyl group, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, or a combination thereof.

As used herein, when specific definition is not otherwise provided, "hetero" refers to one including 1 to 4 heteroatoms selected from N, O, S, Se, Te, Si, and Pi.

As used herein, when a definition is not otherwise provided, "aromatic ring" refers to a functional group in which all atoms in the cyclic functional group have a p-orbital, and wherein these p-orbitals are conjugated and "heteroaromatic ring" refers to the aromatic ring including a heteroatom. The "aromatic ring" refers to a C6 to C30 arene group, for example a C6 to C20 arene group or a C6 to C30 aryl group, for example a C6 to C20 aryl group. The "heteroaromatic ring" refers to a C3 to C30 heteroarene group, for example a C3 to C20 heteroarene group or a C6 to C30 heteroaryl group, for example a C6 to C20 heteroaryl group.

As used herein, "arene group" refers to a hydrocarbon group having an aromatic ring, and includes monocyclic and polycyclic hydrocarbon groups, and the additional ring of the polycyclic hydrocarbon group may be an aromatic ring or a nonaromatic ring. "Heteroarene group" refers to an arene group including 1 to 3 heteroatoms selected from N, O, S, P, and Si.

As used herein, when a definition is not otherwise provided, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like; a group in which two or more hydrocarbon aromatic moieties may be linked by a sigma bond, for example a biphenyl group, a terphenyl group, a quarterphenyl group, and the like; and a group in which two or more hydrocarbon aromatic moieties are fused directly or indirectly to provide a non-aromatic fused ring, for example a fluorenyl group. The aryl group may include a monocyclic, polycyclic or fused polycyclic (i.e., rings sharing adjacent pairs of carbon atoms) functional group.

As used herein, when a definition is not otherwise provided, "heteroaryl group" refers to a group including at least one heteroatom selected from N, O, S, Se, Te, P, and Si instead of carbon (C) in the ring. When the heteroaryl group is a fused ring, is a fused ring, at least one of rings of the heteroaryl group may have a heteroatom or each ring may have a heteroatom.

As used herein, when a definition is not otherwise provided, "ring" refers to an aromatic ring, a non-aromatic ring, a heteroaromatic ring, a hetero non-aromatic ring, a fused ring thereof, and/or a combination thereof. The aromatic ring are the same as described above and the non-aromatic ring may be a C3 to C30 cycloalkyl group, a C3 to C30 cycloalkenyl group, or a C3 to C30 cycloalkynyl group.

As used herein, when a definition is not otherwise provided, "halogen" may be one of F, Cl, Br, or I, and the haloalkyl group may be an alkyl group in which at least one hydrogen is replaced by a halogen and may be, for example, a perfluoroalkyl group such as —CF$_3$.

Hereinafter, a near-infrared absorber according to some example embodiments is described. The near-infrared absorber may be referred to herein interchangeably as a "near-infrared absorbing compound."

The near-infrared absorber includes a compound represented by Chemical Formula 1.

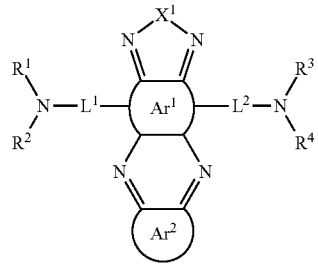

[Chemical Formula 1]

In Chemical Formula 1,

A$^1$ is a substituted or unsubstituted C6 to C30 aromatic ring, a substituted or unsubstituted C3 to C30 heteroaromatic ring, or a combination thereof, Ar$^2$ is a substituted or unsubstituted C6 to C30 aromatic ring, a substituted or unsubstituted C3 to C30 heteroaromatic ring, or a combination thereof, X$^1$ is O, S, Se, Te, S(=O), S(=O$_2$), NR$^a$, CR$^b$R$^c$, or SiR$^d$R$^e$ (wherein R$^a$, R$^b$, R$^c$, and R$^d$ are independently hydrogen, a C1 to C6 alkyl group, a C1 to C6 haloalkyl group, a C6 to C12 aryl group, a C3 to C12 heteroaryl group, a halogen, a cyano group, or a combination thereof), L$^1$ and L$^2$ are independently a substituted or unsubstituted C3 to C20 heteroarylene group, or a fused ring of a substituted or unsubstituted C6 to C20 arylene group and a substituted or unsubstituted C3 to C20 heteroarylene group, R$^1$, R$^2$, R$^3$, and R$^4$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C3 to C30 heteroaryl group, a substituted or unsubstituted silyl group, a halogen, or a combination thereof, and R$^1$ and R$^2$ may independently be present or be linked to each other to form a ring, and R$^3$ and R$^4$ may independently be present or be linked to each other to form a separate ring.

It is desirable that a material absorbing light in a long wavelength like the near-infrared light has small HOMO-LUMO bandgap energy, also referred to herein as small bandgap energy, low bandgap energy, or the like. In order to have the small bandgap energy, a conjugation length thereof may be made to be longer, but when the conjugation length becomes long, a deposition process is difficult to apply. The near-infrared absorber represented by Chemical Formula 1 has a donor-acceptor-donor structure that a core of a conjugation structure having electron-accepting characteristics (an N—X$^1$—N-containing pentagonal ring and an N-containing hexagonal ring in Chemical Formula 1) is linked to an amine groups (*—N(R$^1$)(R$^2$) and *—N(R$^3$)(R$^4$)) having electron-donating characteristics through L$^1$ and L$^2$, and thus the near-infrared absorber has strong charge transfer characteristics and may effectively absorb light in a near-infrared wavelength region due to low bandgap energy. In addition, the near-infrared absorber has improved thermal stability and may be appropriate for a deposition process. Accordingly, a layer and/or structure that includes the near-infrared absorber may have improved sensitivity to and/or absorbance of light in the near-infrared wavelength. A device configured to selectively absorb and/or convert (into electrical signals, e.g., photoelectrically convert) near-infrared light (e.g., a sensor) may have improved performance and/or efficiency based on including the near-infrared absorber, for example in an active layer configured to selectively absorb and/or convert (into electrical signals, e.g., photoelectrically convert) said near-infrared light.

In Chemical Formula 1, $A^1$ may be benzene, a substituted or unsubstituted naphthalene, a substituted or unsubstituted anthracene, a substituted or unsubstituted phenanthrene, a substituted or unsubstituted tetracene, or a substituted or unsubstituted pyrene.

In Chemical Formula 1, $A^1$ may be a substituted or unsubstituted quinoline, a substituted or unsubstituted isoquinoline, a substituted or unsubstituted quinoxaline, a substituted or unsubstituted quinazoline, or a substituted or unsubstituted phenanthroline.

In Chemical Formula 1, $A^1$ may be one moiety of a set of moieties represented by Chemical Formula A-1, each moiety including at least one aromatic ring and left and right linking groups.

[Chemical Formula A-1]

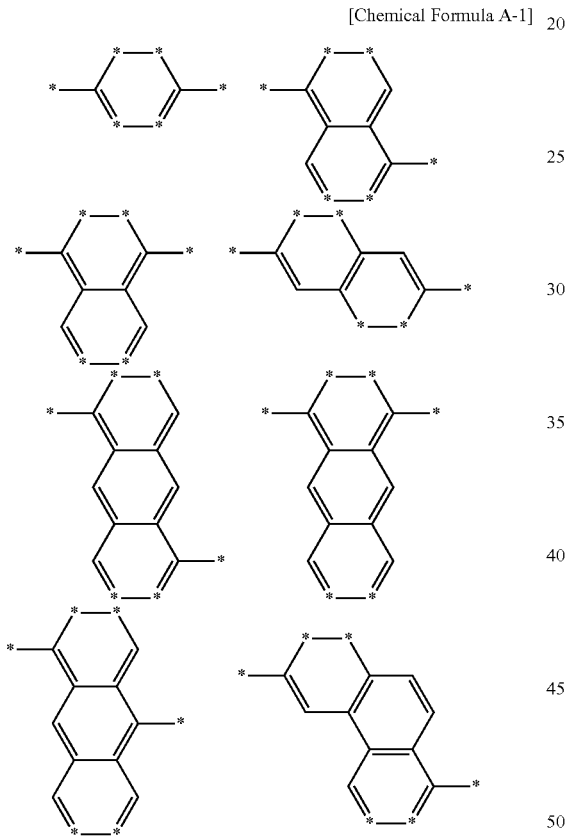

[Chemical Formula A-2]

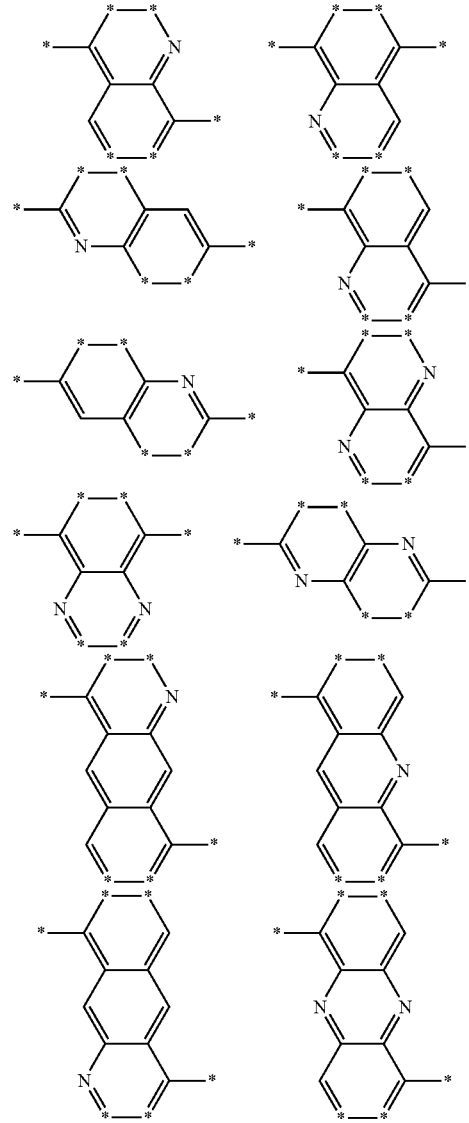

In Chemical Formula A-1, hydrogen of each aromatic ring may be replaced by a halogen, a cyano group, a C1 to C10 alkyl group, a C1 to C10 haloalkyl group, a silyl group, or a C1 to C10 alkylsilyl group, separate adjacent pairs of *'s inside the at least one aromatic ring are linking portions with separate, respective ones of an N—$X^1$—N-containing pentagonal ring of Chemical Formula 1 and an N-containing hexagonal ring of Chemical Formula 1, and *'s of the left and right linking groups are portions linked to separate, respective ones of $L^1$ and $L^2$ of Chemical Formula 1.

In Chemical Formula 1, $A^1$ may be one moiety of a set of moieties represented by Chemical Formula A-2, each moiety including at least one aromatic ring and left and right linking groups.

In Chemical Formula A-2, hydrogen of each aromatic ring may be replaced by a halogen, a cyano group, a C1 to C10 alkyl group, a C1 to C10 haloalkyl group, a silyl group, or a C1 to C10 alkylsilyl group, separate adjacent pairs of *'s inside the at least one aromatic ring are linking portions with separate, respective ones of an N—$X^1$—N-containing pentagonal ring of Chemical Formula 1 and an N-containing hexagonal ring of Chemical Formula 1, and *'s of the left and right linking groups are portions linked to separate, respective ones of $L^1$ and $L^2$ of Chemical Formula 1.

In Chemical Formula 1, Are may be a substituted or unsubstituted benzene, a substituted or unsubstituted naphthalene, a substituted or unsubstituted acenaphthene, a substituted or unsubstituted anthracene, a substituted or unsubstituted phenanthrene, a substituted or unsubstituted tetracene, or a substituted or unsubstituted pyrene.

In Chemical Formula 1, $Ar^2$ may be a substituted or unsubstituted quinoline, a substituted or unsubstituted isoquinoline, a substituted or unsubstituted quinoxaline, a substituted or unsubstituted quinazoline, a substituted or unsubstituted phenanthroline, a substituted or unsubstituted pyrimidine, or a substituted or unsubstituted benzodithiophene.

In Chemical Formula 1, Ar$^2$ may be one moiety of a set of moieties represented by Chemical Formula B-1, each moiety including at least one aromatic ring.

[Chemical Formula B-1]

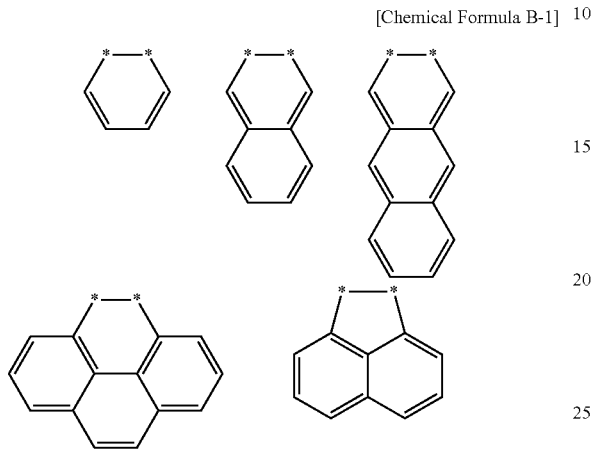

In Chemical Formula B-1, hydrogen of each aromatic ring may be replaced by a halogen, a cyano group, a C1 to C10 alkyl group, a C1 to C10 haloalkyl group, —SiH$_3$, a C1 to C10 alkylsilyl group, a C6 to C20 aryl group, or a C3 to C20 heteroaryl group, and *'s inside the at least one aromatic ring are linking portions with the N-containing hexagonal ring of Chemical Formula 1.

In Chemical Formula 1, Ar$^2$ may be one moiety of a set of moieties represented by Chemical Formula B-2, each moiety including at least one aromatic ring.

[Chemical Formula B-2]

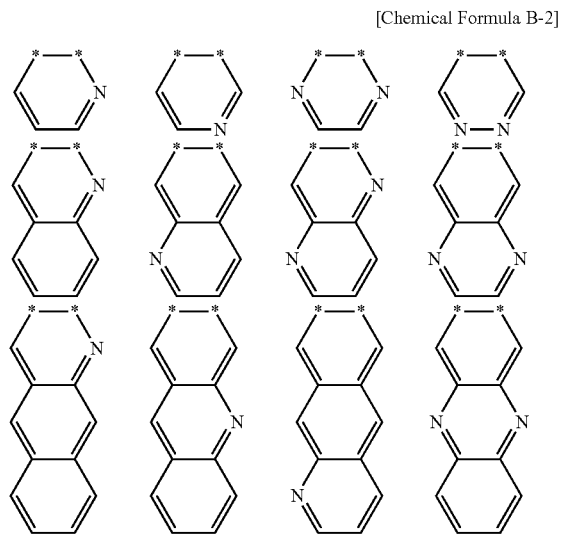

In Chemical Formula B-2, hydrogen of each aromatic ring may be replaced by a halogen, a cyano group, a C1 to C10 alkyl group, a C1 to C10 haloalkyl group, —SiH$_3$, a C1 to C10 alkylsilyl group, a C6 to C20 aryl group, or a C3 to C20 heteroaryl group, and *'s inside the at least one aromatic ring are linking portions with the N-containing hexagonal ring of Chemical Formula 1.

In Chemical Formula 1, Ar$^2$ may be a moiety represented by Chemical Formula B-3a or Chemical Formula B-3b.

[Chemical Formula B-3a]

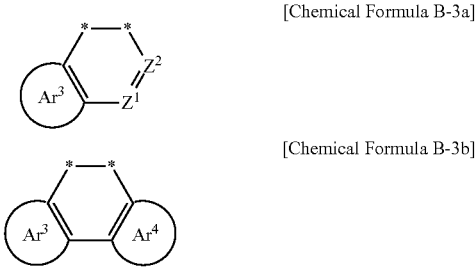

[Chemical Formula B-3b]

In Chemical Formula B-3a,

Z$^1$ and Z$^2$ are independently N or CR$^a$ (wherein R$^a$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof), Ar$^3$ is a substituted or unsubstituted C6 to C30 arene group or a substituted or unsubstituted C3 to C30 heteroarene group, and

*'s inside the at least one aromatic ring are linking portions with the N-containing hexagonal ring of Chemical Formula 1.

In Chemical Formula B-3b,

Ar$^3$ and Ar$^4$ are independently a substituted or unsubstituted C6 to C30 arene group or a substituted or unsubstituted C3 to C30 heteroarene group,

*'s inside the at least one aromatic ring are linking portions with the N-containing hexagonal ring of Chemical Formula 1.

The moiety represented by Chemical Formula B-3a may be represented by Chemical Formula B-3aa, and the moiety represented by Chemical Formula B-3b may be represented by Chemical Formula B-3bb, each moiety including at least one aromatic ring.

[Chemical Formula B-3aa]

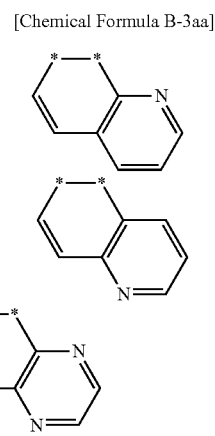

-continued

[Chemical Formula B-3bb]

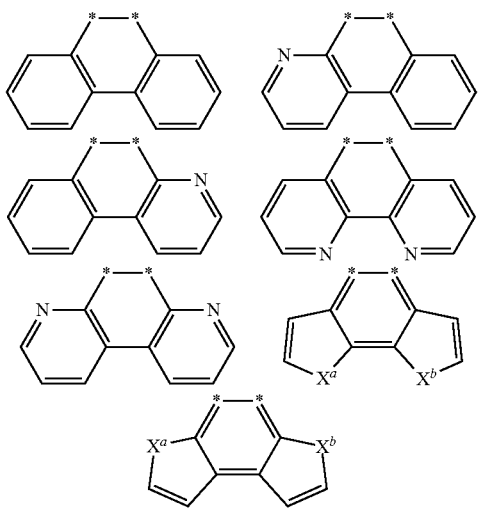

In Chemical Formula B-3aa and Chemical Formula B-3bb, hydrogen of each aromatic ring may be replaced by a halogen, a cyano group, a C1 to C10 alkyl group, a C1 to C10 haloalkyl group, —SiH$_3$, a C1 to C10 alkylsilyl group, a C6 to C20 aryl group, or a C3 to C20 heteroaryl group,

*'s inside the at least one aromatic ring are linking portions with the N-containing hexagonal ring of Chemical Formula 1, and $X^a$ and $X^b$ are independently —O—, —S—, —Se—, —Te—, —NR$^a$—, —SiR$^b$R$^b$—, or —GeR$^d$R$^e$— (wherein R$^a$, R$^b$, R$^c$, R$^d$, and R$^e$ are independently hydrogen, a halogen, a substituted or unsubstituted C1 to C10 alkyl group, or a substituted or unsubstituted C6 to C10 aryl group).

For example, in Chemical Formulas B-3aa and B-3bb, the halogen may be one of F, Cl, Br, or I, and the haloalkyl group may be an alkyl group in which at least one hydrogen is replaced by a halogen, for example a perfluoroalkyl group such as —CF$_3$.

In Chemical Formula 1, L$^1$ and L$^2$ may be a linker including a hetero ring (e.g., a single ring or a fused ring) in which a hetero atom included in the ring may enhance charge transfer characteristics and reduce bandgap energy.

L$^1$ and L$^2$ may be the same as or different from each other, and may each be represented by one of Chemical Formulas C-1 to C-4.

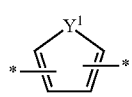 (C-1)

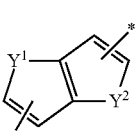 (C-2)

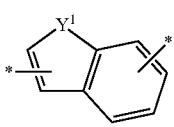 (C-3)

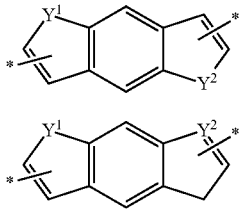 (C-4)

(C-5)

In Chemical Formulas C-1 to C-4,

Y$^1$ and Y$^2$ are independently O, S, Se, Te, S(=O), S(=O)$_2$, NR$^a$, or SiR$^b$R$^c$ (wherein R$^a$, R$^b$, and R$^c$ are independently hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof), R$^b$ and R$^c$ are independently present or linked to each other to form a ring, and each * is a linking point with Chemical Formula 1.

L$^1$ and L$^2$ may be linked to a symmetrical position or to an asymmetrical position with respect to Ar$^1$.

In Chemical Formula 1, *—N(R$^1$)(R$^2$) and *—N(R$^3$)(R$^4$) may be independently represented by Chemical Formula D-1 or D-2.

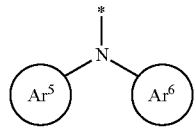 [Chemical Formula D-1]

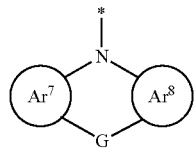 [Chemical Formula D-2]

In Chemical Formula D-1,

Ar$^5$ and Ar$^6$ are independently a substituted or unsubstituted C6 to C30 aryl group or a substituted or unsubstituted C3 to C30 heteroaryl group, and

* is a linking point with Chemical Formula 1, wherein, in Chemical Formula D-2,

A$^1$ and Ar$^8$ are independently a substituted or unsubstituted C6 to C30 arene group or a substituted or unsubstituted C3 to C30 heteroarene group, G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))— (wherein R$^a$, R$^b$, R$^c$, R$^d$, R$^e$, R$^f$, R$^g$, R$^h$, and R$^i$ are independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a ring, and n of —(CR$^f$R$^g$)$_n$— is an integer of 1 or 2), and

* is a linking point with Chemical Formula 1.

Chemical Formula D-1 may be represented by Chemical Formula D-1a or D-1b.

[Chemical Formula D-1a]

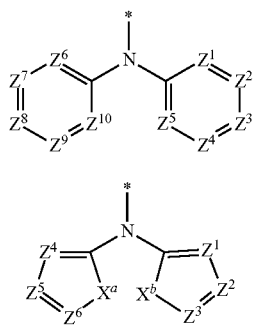

[Chemical Formula D-1b]

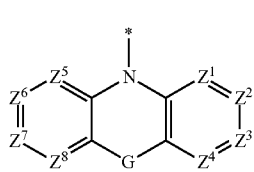

In Chemical Formula D-1a, $Z^1$ to $Z^{10}$ are independently N or $CR^a$ (wherein $R^a$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof), when $Z^1$ to $Z^{16}$ are $CR^a$, $R^a$'s may independently be present or two adjacent groups of $Z^1$ to $Z^{16}$ may be linked to each other to form a 5-membered aromatic ring or a 6-membered aromatic ring, and

* is a linking point with Chemical Formula 1.

According to some example embodiments, at least one of $Z^1$ to $Z^5$ and/or at least one of $Z^6$ to $Z^{16}$ in Chemical Formula D-1a may be N. According to some example embodiments, at least two of $Z^1$ to $Z^5$ and/or at least two of $Z^6$ to $Z^{16}$ in Chemical Formula D-1a may be N.

In Chemical Formula D-1b, $X^a$ and $X^b$ are independently —O—, —S—, —Se—, —Te—, —NR$^a$—, —SiR$^b$R$^b$—, or —GeR$^d$R$^e$— (wherein $R^a$, $R^b$, $R^c$, $R^d$, and $R^e$ are independently hydrogen, a halogen, a substituted or unsubstituted C1 to C10 alkyl group, or a substituted or unsubstituted C6 to C10 aryl group), $Z^1$ to $Z^6$ are independently N or $CR^x$ (wherein $R^x$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof), when $Z^1$ to $Z^6$ are $CR^x$, $R^x$'s are independently present or two adjacent groups of $Z^1$ to $Z^6$ are linked to each other to form a 5-membered aromatic ring or a 6-membered aromatic ring, and

* is a linking point with Chemical Formula 1.

According to some example embodiments, at least one of $Z^1$ to $Z^3$ and/or at least one of $Z^4$ to $Z^6$ in Chemical Formula D-1b may be N. According to some example embodiments, at least two of $Z^1$ to $Z^3$ and/or at least two of $Z^4$ to $Z^6$ in Chemical Formula D-1b may be N.

Chemical Formula D-2 may be represented by Chemical Formula D-2a, Chemical Formula D-2b, or Chemical Formula D-2c.

[Chemical Formula D-2a]

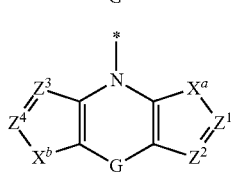

[Chemical Formula D-2b]

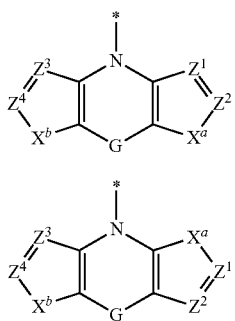

[Chemical Formula D-2c]

In Chemical Formula D-2a,

G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))— (wherein $R^a$, $R^b$, $R^c$, $R^d$, $R^e$, $R^f$, $R^g$, $R^h$, and $R^i$ are independently hydrogen, a halogen, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and $R^i$ are independently present or are linked to each other to form a ring, and n of —(CR$^f$R$^g$)$_n$— is an integer of 1 or 2), $Z^1$ to $Z^8$ are independently N or $CR^x$ (wherein $R^x$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof), when $Z^1$ to $Z^8$ are $CR^x$, $R^x$ may independently be present or two adjacent groups of $Z^1$ to $Z^8$ may be linked to each other to form a 5-membered aromatic ring or a 6-membered aromatic ring, and

* is a linking point with Chemical Formula 1.

According to some example embodiments, at least one of $Z^1$ to $Z^4$ and/or at least one of $Z^5$ to $Z^8$ in Chemical Formula D-2a may be N. According to some example embodiments, at least two of $Z^1$ to $Z^4$ and/or at least two of $Z^5$ to $Z^8$ in Chemical Formula D-2a may be N.

In Chemical Formulas D-2b and D-2c,

G is a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))— (wherein $R^a$, $R^b$, $R^c$, $R^d$, $R^e$, $R^f$, $R^g$, $R^h$, and $R^i$ are independently hydrogen, a halogen, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and $R^i$ are independently present or are linked to each other to form a ring, and n of —(CR$^f$R$^g$)$_n$— is an integer of 1 or 2), $X^a$ and $X^b$ are independently —O—, —S—, —Se—, —Te—, —NR$^p$—, —SiR$^q$R$^r$— or —GeR$^s$R$^t$— (wherein $R^p$, $R^q$, $R^r$, $R^s$, and $R^t$ are independently hydrogen, a halogen, a substituted or unsubstituted C1 to C10 alkyl group, or a substituted or unsubstituted C6 to C10 aryl group), $Z^1$ to $Z^4$ are independently N or $CR^x$ (wherein $R^x$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof), and when $Z^1$ to $Z^4$ are $CR^x$, $R^x$'s may independently be present or two adjacent groups of $Z^1$ to $Z^6$ may be linked to each other to form a 5-membered aromatic ring or a 6-membered aromatic ring.

According to some example embodiments, at least one of $Z^1$ and $Z^2$ and/or at least one of $Z^3$ and $Z^4$ in Chemical Formula D-2b may be N. According to some example embodiments, $Z^1$ and $Z^2$ and/or $Z^3$ and $Z^4$ in Chemical Formula D-2b may be N.

According to some example embodiments, at least one of $Z^1$ and $Z^2$ and/or at least one of $Z^3$ and $Z^4$ in Chemical Formula D-2c may be N. According to some example embodiments, $Z^1$ and $Z^2$ and/or $Z^3$ and $Z^4$ in Chemical Formula D-2c may be N.

Chemical Formula D-1 may be represented by one of Chemical Formulas D-1-1 to D-1-12.

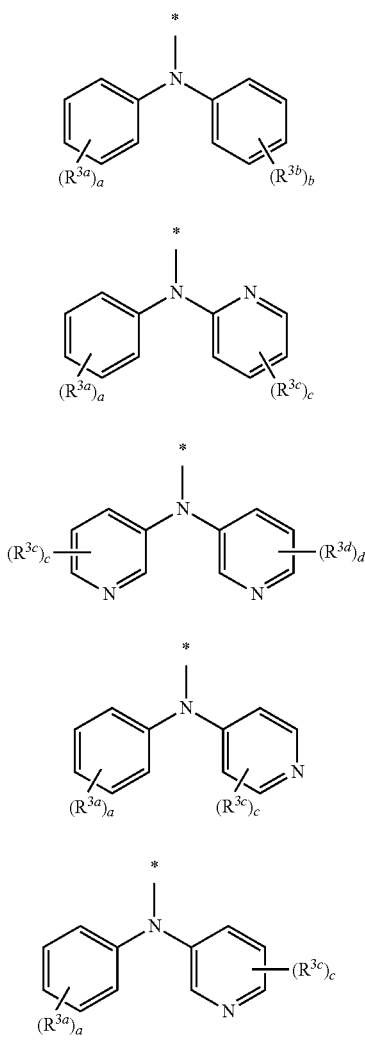
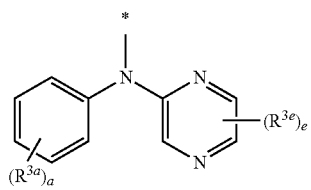
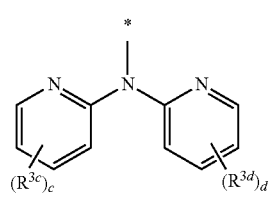
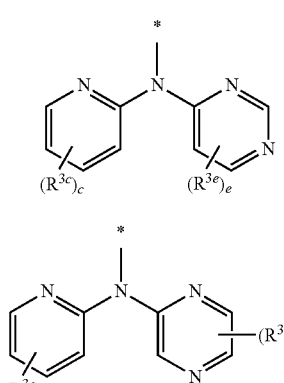
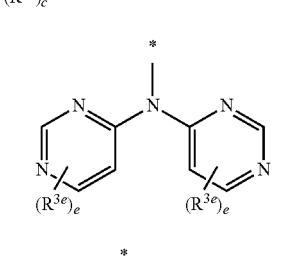
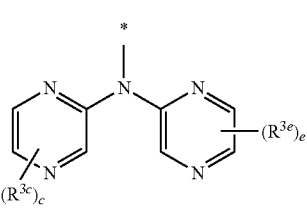

In Chemical Formulas D-1-1 to D-1-12,
a and b are independently an integer of 1 to 5,
c and d are independently an integer of 1 to 4,
e is an integer of 1 to 3, and
$R^{3a}$ to $R^{3e}$ are independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally when a, b, c, d, and e are two or more, adjacent two groups of a plurality of $R^{3a}$'s, adjacent two groups of a plurality of $R^{3b}$'s, adjacent two groups of a plurality of a plurality of $R^{3b}$'s, adjacent two groups of a plurality of $R^{3d}$'s, or adjacent two groups of a plurality of We's are linked to each other to form a 5-membered aromatic ring or a 6-membered aromatic ring.

Chemical Formula D-2 may be represented by one of Chemical Formulas D-2-1 to D-2-12.

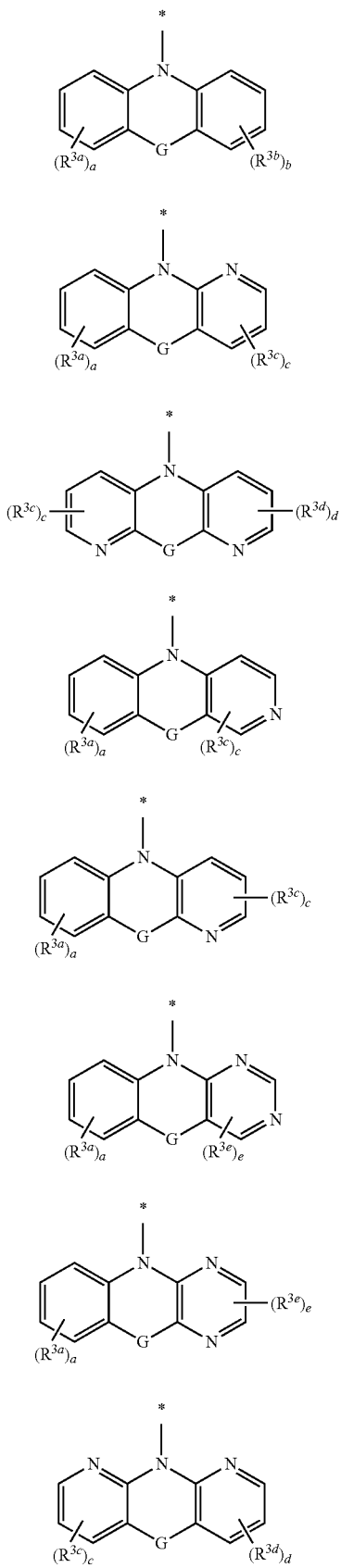

In Chemical Formulas D-2-1 to D-2-12,
a and b are independently an integer of 1 to 4,
c and d are independently an integer of 1 to 3,
e is an integer of 1 or 2,
G is a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))— (wherein R$^a$, R$^b$, R$^c$, R$^d$, R$^e$, R$^f$, R$^g$, R$^h$, and R$^i$ are independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a ring, and n of —(CR$^f$R$^g$)$_n$— is an integer of 1 or 2), and R$^{3a}$ to R$^{3e}$ are independently hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally when a, b, c, d, and e are two or more, adjacent two groups of a plurality of R$^{3a}$'s, adjacent two groups of a plurality of R$^{3b}$'s, adjacent two groups of a plurality of R$^{c}$'s, adjacent two groups of a plurality of R$^{3d}$'s, or adjacent two groups of a plurality of R$^{3e}$'s are linked to each other to form a 5-membered aromatic ring or a 6-membered aromatic ring.

The near-infrared absorber may absorb light in a near-infrared wavelength region. The near-infrared absorber may have a peak absorption wavelength ($\lambda_{max}$) of, for example, greater than or equal to about 750 nm, greater than or equal to about 780 nm, greater than or equal to about 790 nm, greater than or equal to about 800 nm, greater than or equal to about 810 nm, greater than or equal to about 820 nm, or greater than or equal to about 830 nm. The near-infrared absorber may have a peak absorption wavelength ($\lambda_{max}$) of, for example, about 750 nm to about 3000 nm, about 750 nm to about 2500 nm, about 780 nm to about 2200 nm, about 790 nm to about 2100 nm, about 800 nm to about 2000 nm, about 810 nm to about 2000 nm, about 820 nm to about 2000 nm, or about 830 nm to about 2000 nm.

The near-infrared absorber may exhibit good charge transfer characteristics, and thus, it has good photoelectric conversion characteristics that absorb (e.g., selectively absorb) light and/or convert it (e.g., photoelectrically convert it) into an electrical signal, and thus may be effectively used as a photoelectric conversion material for photoelectric devices. Accordingly, a photoelectric device that includes the near-infrared absorber, for example in an active layer and/or charge auxiliary layer of the photoelectric device (e.g., active layer 30 shown in FIGS. 1 and 2 and/or charge auxiliary layers 40 and 45 shown in FIG. 2) may have improved operational performance and/or efficiency, for example having improved operational performance and/or efficiency with regard to implementing photoelectric conversion of incident near-infrared light, based on including the near-infrared absorber.

The near-infrared absorber has good heat resistance, and thus may prevent or reduce thermal decomposition during deposition, and thus may be repeatedly deposited. The near-infrared absorber may be thermally or vacuum deposited and may be deposited, for example, by sublimation. For example, deposition by sublimation may be confirmed by thermogravimetric analysis (TGA), and at a thermogravimetric analysis at a pressure of less than or equal to about 10 Pa, a temperature at which a 10% weight loss relative to an initial weight may be less than or equal to about 400° C., for example less than or equal to about 390° C., less than or equal to about 380° C., less than or equal to about 370° C., less than or equal to about 360° C., or less than or equal to about 350° C. For example, at a thermogravimetric analysis of the near-infrared absorber at a pressure of less than or equal to about 10 Pa, for example temperature at which a 10% weight loss relative to an initial weight may be about 230° C. to about 400° C.

Some example embodiments provide a near-infrared absorbing/blocking film including the near-infrared absorber.

The near-infrared absorbing/blocking film may be applied to various fields requiring light absorption characteristics in a near-infrared wavelength region.

The near-infrared absorber has both light absorption characteristics and photoelectric characteristics in a near-infrared wavelength region, and thus it may be effectively used as a photoelectric conversion material.

FIG. 1 is a cross-sectional view of a photoelectric device according to some example embodiments.

Referring to FIG. 1, a photoelectric device 100 according to some example embodiments includes a first electrode 10 and a second electrode 20 facing each other and an active layer 30 disposed between the first electrode 10 and the second electrode 20.

A substrate (not shown) may be disposed at the side of the first electrode 10 or the second electrode 20. The substrate may be for example made of (e.g., may at least partially comprise) an inorganic material such as glass; an organic material such as polycarbonate, polymethylmethacrylate, polyethyleneterephthalate, polyethylenenaphthalate, polyamide, polyethersulfone, or a combination thereof; or a silicon wafer. The substrate may be omitted.

One of the first electrode 10 or the second electrode 20 is an anode and the other is a cathode. For example, the first electrode 10 may be a cathode and the second electrode 20 may be an anode.

At least one of the first electrode 10 or the second electrode 20 may be a light-transmitting electrode and the light-transmitting electrode may be for example made of a conductive oxide such as an indium tin oxide (ITO), indium zinc oxide (IZO), zinc oxide (ZnO), tin oxide (SnO), aluminum tin oxide (AITO), and fluorine doped tin oxide (FTO), or a metal thin layer of a single layer or a multilayer. When one of the first electrode 10 or the second electrode 20 is a non-light-transmitting electrode, it may be made of for example an opaque conductor such as aluminum (Al), silver (Ag), or gold (Au). For example, the first electrode 10 and the second electrode 20 may be all light-transmitting electrodes. For example, the second electrode 20 may be a light receiving electrode disposed at a light receiving side.

The active layer 30 is a layer including a p-type semiconductor and an n-type semiconductor configured to provide a pn junction, which is a layer that may produce excitons by receiving light from outside (e.g., an exterior of the active layer 30) and then separating holes and electrons from the produced excitons.

The p-type semiconductor and the n-type semiconductor may be independently a light absorbing material that is configured to absorb (e.g., selectively absorb) light in at least one portion of a wavelength region and the aforementioned near-infrared absorber may be a p-type semiconductor or an n-type semiconductor. For example, the aforementioned near-infrared absorber may be used for a p-type semiconductor and fullerene or a fullerene derivative may be included as an n-type semiconductor. Accordingly, it will be understood that the active layer 30 may at least partially comprise the aforementioned near-infrared absorber (e.g., may include the near-infrared absorber and either fullerene or a fullerene derivative). The active layer 30, and thus the photoelectric device 100 may have improved near-infrared light absorption characteristics (e.g., may have improved sensitivity to light in a near-infrared wavelength region, improved absorbance of light in the near-infrared wavelength region, etc.) and thus improved photoelectric conversion performance and/or efficiency and/or improved thermal stability based on the active layer including the aforementioned near-infrared absorber. In some example embodiments, the active layer 30 may be a near-infrared absorbing/blocking film that includes the near-infrared absorber.

The active layer 30 may include an intrinsic layer in which the aforementioned near-infrared absorber (e.g., p-type semiconductor) and fullerene or a fullerene derivative (e.g., n-type semiconductor) are co-deposited. Herein, the p-type semiconductor and the n-type semiconductor may be included in a volume ratio of about 1:9 to about 9:1, for example about 2:8 to about 8:2, about 3:7 to about 7:3, about 4:6 to about 6:4, or about 5:5.

The active layer 30 may further include a p-type layer and/or an n-type layer in addition to the intrinsic layer. The p-type layer may include the aforementioned near-infrared absorber (e.g., p-type semiconductor) and the n-type layer may include the aforementioned n-type semiconductor (e.g., n-type semiconductor). For example, they may be included in various combinations of p-type layer/I layer, I layer/n-type layer, p-type layer/I layer/n-type layer, and the like.

The photoelectric device 100 may further include an auxiliary layer between the first electrode 10 and the active layer and/or the second electrode 20 and the active layer. The auxiliary layer may be a charge auxiliary layer or an optical auxiliary layer. This optoelectronic device (e.g., photoelectric device) is shown in FIG. 2.

Figure 2:
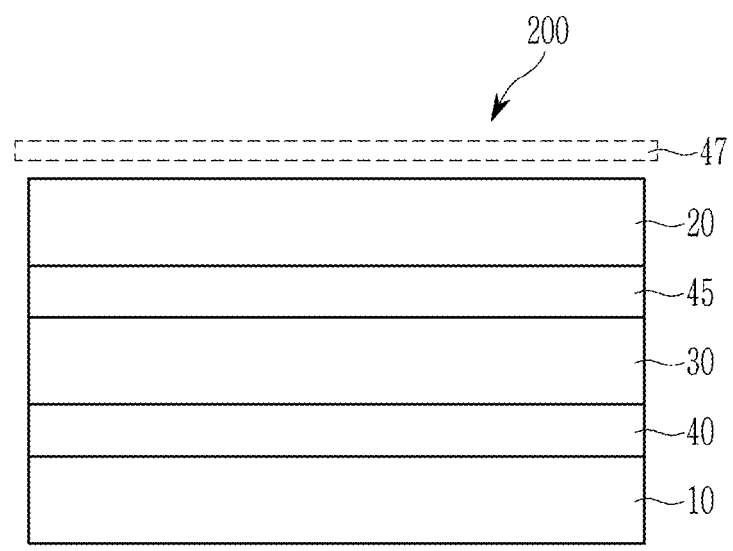
FIG. 2 is a cross-sectional view showing a photoelectric device according to some example embodiments.
Figure 2:
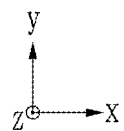

FIG. 2 is a cross-sectional view showing a photoelectric device according to some example embodiments.

Referring to FIG. 2, a photoelectric device 200 includes a first electrode 10 and a second electrode 20 facing each other, an active layer 30 between the first electrode 10 and the second electrode 20, a first auxiliary layer 40 between the first electrode 10 and the active layer 30, and a second auxiliary layer 45 between the second electrode 20 and the active layer 30. In some example embodiments, only one of the first auxiliary layer 40 or the second auxiliary layer 45 is included in the photoelectric device 200.

The first auxiliary layer 40 and the second auxiliary layer 45 may each be a charge auxiliary layer that may make holes and electrons separated in the active layer 30 be transported more easily to improve efficiency of the photoelectric device 200.

The charge auxiliary layers may include at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and/or 45 may include for example an organic material, an inorganic material, or an organic/inorganic material. The organic material may be an organic material having hole or electron characteristics and the inorganic material may be for example a metal oxide such as a molybdenum oxide, a tungsten oxide, or a nickel oxide.

The charge auxiliary layers 40 and/or 45 may include for example the aforementioned near-infrared absorber. In some example embodiments, the charge auxiliary layers 40 and/or 45 may include the aforementioned near-infrared absorber and the active layer 30 may also include the aforementioned near-infrared absorber. In some example embodiments, the charge auxiliary layers 40 and/or 45 may include the aforementioned near-infrared absorber and the active layer 30 may not include the aforementioned near-infrared absorber. The charge auxiliary layers 40 and/or 45, and thus the photoelectric device 200, may have improved near-infrared light absorption characteristics (e.g., may have improved sensitivity to light in a near-infrared wavelength region, improved absorbance of light in the near-infrared wavelength region, etc.) and thus improved photoelectric conversion performance and/or efficiency, and/or improved thermal stability based on the charge auxiliary layers 40 and/or 45 including the aforementioned near-infrared absorber.

The optical auxiliary layer may be disposed in the light incident direction of the photoelectric device. For example, when the second electrode 20 is a light receiving electrode (e.g., the electrode proximate to a surrounding environment from which light is received at the photoelectric device 200), the optical auxiliary layer may be disposed on the active layer 30. For example, the optical auxiliary layer may be disposed between the second electrode 20 and the active layer 30.

The photoelectric devices 100 and 200 may further include an anti-reflection layer 47 on one surface of the first electrode 10 or the second electrode 20. The anti-reflection layer 47 is disposed at a light incidence side and lowers reflectance of light of incident light and thereby light absorbance is further improved. For example, when light enters from the first electrode 10, the anti-reflection layer 47 may be disposed on the first electrode 10 while when light enters from the second electrode 20, the anti-reflection layer may be disposed under the second electrode 20.

The anti-reflection layer 47 may include, for example a material having a refractive index of about 1.6 to about 2.5 and may include for example at least one of a metal oxide, a metal sulfide, or an organic material having a refractive index within the ranges. The anti-reflection layer 47 may include, for example a metal oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganese-containing oxide, a chromium-containing oxide, a tellurium-containing oxide, or a combination thereof; a metal sulfide such as zinc sulfide; or an organic material such as an amine derivative, but is not limited thereto.

In the photoelectric devices 100 and 200, when light enters said photoelectric device 100 and/or 200 and thus enters the active layer 30 thereof from (e.g., via) the first electrode 10 or the second electrode 20, and the active layer 30 thus absorbs the light in a particular (or, alternatively, predetermined) wavelength region, excitons may be generated thereinside. The excitons are separated into holes and electrons in the active layer 30, and the separated holes are transported to an anode that is one of the first electrode 10 or the second electrode 20 and the separated electrons are transported to the cathode that is the other of the first electrode 10 and the second electrode 20 so as to flow (e.g., induce, generate, etc.) a current (e.g., an electrical current).

The photoelectric devices 100 and 200 may be applied to (e.g., included in) a solar cell, an image sensor, a photodetector, a photosensor, and an organic light emitting diode (OLED), but example embodiments are not limited thereto.

The photoelectric devices 100 and 200 may be applied to (e.g., included in) an organic sensor. The organic sensor may be an organic CMOS sensor, for example, an organic CMOS infrared light sensor or an organic CMOS image sensor.

In some example embodiments, the photoelectric device 100 may include the near-infrared absorber in any of the elements thereof, including, in addition to or alternative to the active layer 30, one or more of the first electrode 10 or the second electrode 20. In some example embodiments, the photoelectric device 200 may include the near-infrared absorber in any of the elements thereof, including, in addition to or alternative to the active layer 30 and/or one or more of the charge auxiliary layers 40/45, one or more of the first electrode 10 or the second electrode 20.

Figure 3:
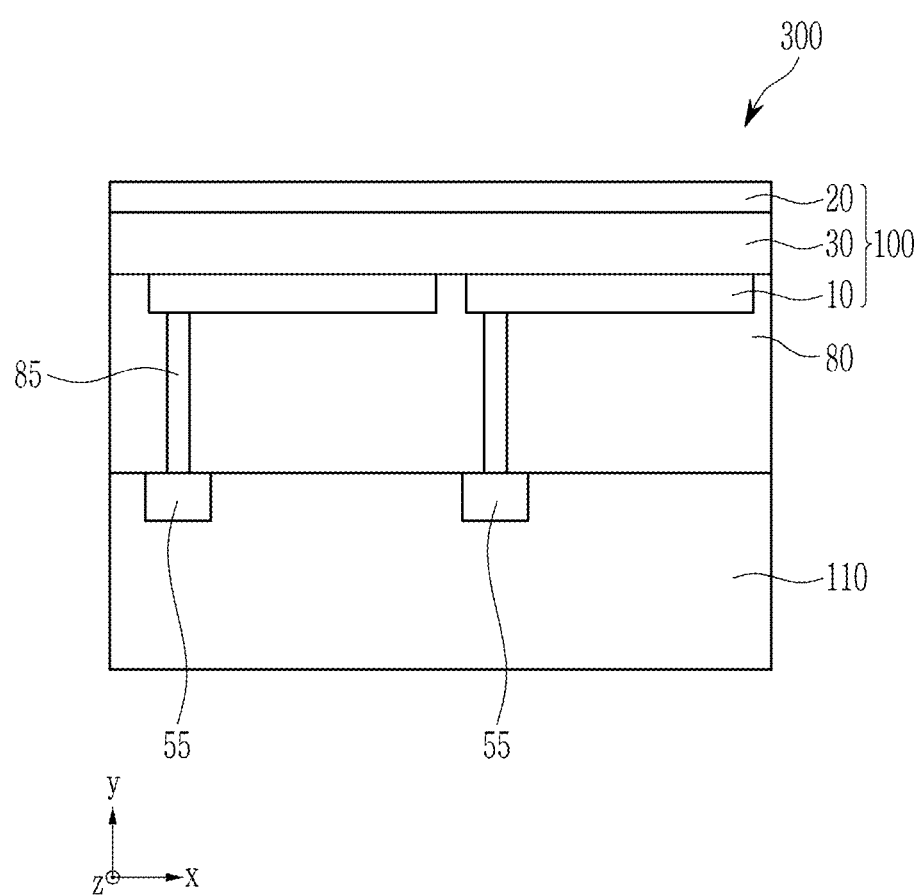
FIG. 3 is a cross-sectional view showing an organic sensor according to some example embodiments.

FIG. 3 is a cross-sectional view showing an organic sensor according to some example embodiments.

The organic sensor 300 according to some example embodiments includes a semiconductor substrate 110, an insulation layer 80, and a photoelectric device 100.

The semiconductor substrate 110 may be a silicon substrate and is integrated with a transmission transistor (not shown) and a charge storage 55. The charge storage 55 may be integrated in each pixel. The charge storage 55 is electrically connected to the photoelectric device 100 and information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the semiconductor substrate 110.

The insulation layer 80 is formed on the metal wire and pad. The insulation layer 80 may be made of an inorganic insulating material such as a silicon oxide and/or a silicon nitride, or a low dielectric constant (low K) material such as SiC, SiCOH, SiCO, and SiOF. The insulation layer 60 has a trench 85 exposing the charge storage 55. The trench 85 may be filled with fillers.

The aforementioned photoelectric device 100 is formed on the insulation layer 80. As described above, the photoelectric device 100 includes a first electrode 10, an active layer 30, and a second electrode 20. Even though a structure in which the first electrode 10, the active layer 30 and the second electrode 20 are sequentially stacked is shown as an example in the drawing, the present disclosure is not limited to this structure, and the second electrode 20, the active layer 30, and the electrodes 10 may be arranged in this order.

The first electrode 10 and the second electrode 20 may both be transparent electrodes, and the active layer 30 may be the same as described above with reference to FIGS. 1 and 2. The active layer 30 may selectively absorb light in a near-infrared wavelength region. Incident light from the side of the second electrode 20 may be photoelectrically converted by mainly absorbing light in a near-infrared wavelength region in the active layer 30. As noted above with reference to FIG. 1, the active layer 30 may include the aforementioned near-infrared absorber and thus may have improved sensitivity to near-infrared light, such that the operational performance and/or efficiency of the organic sensor 300 in absorbing and/or converting incident near-infrared light into electrical signals (e.g., photoelectric conversion performance and/or efficiency) may be improved.

Focusing lens (not shown) may be further formed on the photoelectric device 100. The focusing lens may control a direction of incident light and gather the light in one region. The focusing lens may have a shape of, for example, a cylinder or a hemisphere, but is not limited thereto.

Although the organic sensor to which the photoelectric device 100 of FIG. 1 is applied is illustrated in FIG. 3, the photoelectric device 200 according to FIG. 2 may be equally applied (e.g., included in place of photoelectric device 100 in the organic sensor 300).

The organic sensor according to some example embodiments may be an organic infrared light sensor, for example an iris sensor or a depth sensor.

The iris sensor identifies a person by using unique iris characteristics of every person and specifically, taking an image of an eye of a user within an appropriate distance, processing the image, and comparing it with his/her stored image.

The depth sensor identifies a shape and a location of an object from its three-dimensional information by taking an image of the object within an appropriate distance with a user and processing the image. This depth sensor may be for example used as a face recognition sensor.

Figure 4:
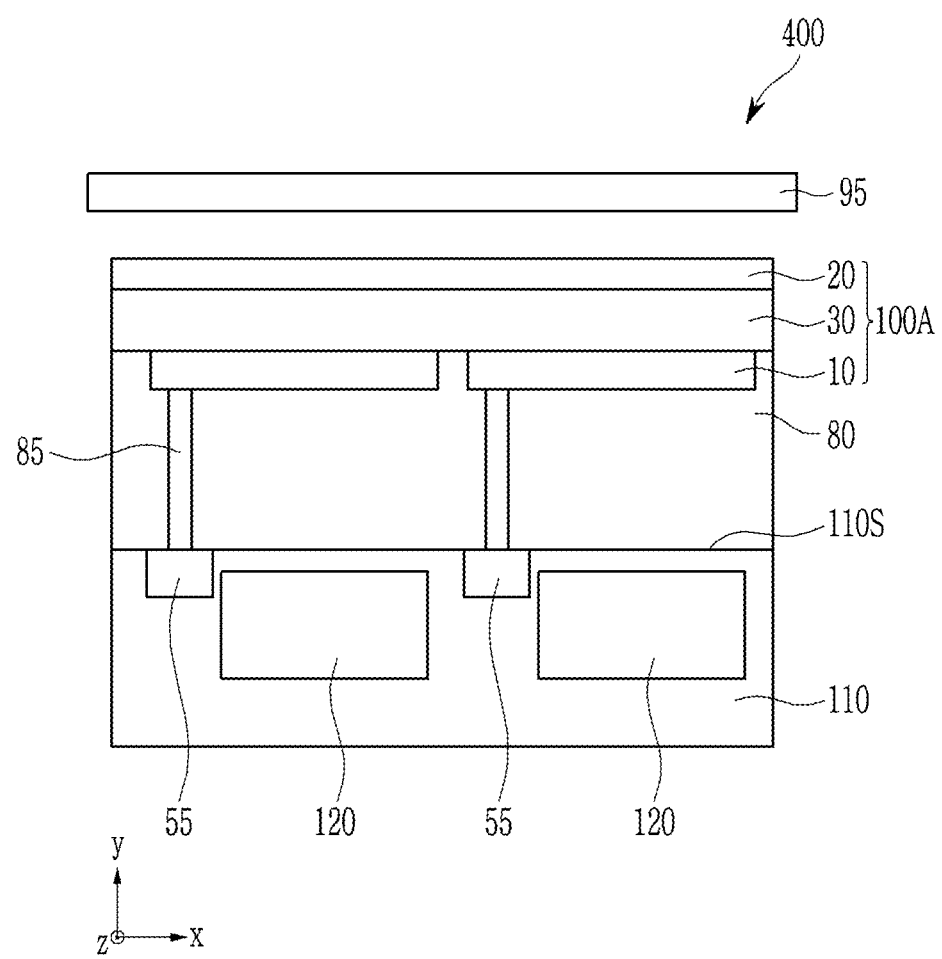
FIG. 4 is a cross-sectional view showing an organic sensor according to some example embodiments.

FIG. 4 is a cross-sectional view showing an organic sensor according to some example embodiments.

The organic sensor according to some example embodiments may include a plurality of sensors having different functions. For example, at least one of the plurality of sensors having different functions may be a biometric sensor, and the biometric sensor may be for example an iris sensor, a depth sensor, a fingerprint sensor, a blood vessel distribution sensor, and the like, but is not limited thereto. For example, one sensor of the plurality of sensors having different functions may be an iris sensor and another sensor of the plurality of sensors having different functions may be a depth sensor.

For example, a plurality of sensors may include, for example a first infrared light sensor configured to sense (e.g., selectively absorb and/or convert (into electrical signals, e.g., photoelectrically convert)) light in an infrared region (e.g., infrared wavelength region) having a first wavelength ($\lambda_1$) in an infrared wavelength region and a second infrared light sensor configured to sense (e.g., selectively absorb and/or convert (into electrical signals, e.g., photoelectrically convert)) light in an infrared region having a second wavelength ($\lambda_2$) in an infrared wavelength region (e.g., a same or different infrared wavelength region as the infrared wavelength region including the first wavelength ($\lambda_1$)).

The first wavelength ($\lambda_1$) and the second wavelength ($\lambda_2$) may be for example different in a wavelength region of about 750 nm to about 3000 nm, and for example a difference between the first wavelength ($\lambda_1$) and the second wavelength ($\lambda_2$) may be greater than or equal to about 30 nm, greater than or equal to about 50 nm, greater than or equal to about 70 nm, greater than or equal to about 80 nm, or greater than or equal to about 90 nm.

For example, one of the first wavelength ($\lambda_1$) or the second wavelength ($\lambda_2$) may belong to a wavelength region of about 780 nm to about 900 nm and the other of the first wavelength ($\lambda_1$) or the second wavelength ($\lambda_2$) may belong to a wavelength region of about 830 nm to about 1000 nm.

For example, one of the first wavelength ($\lambda_1$) or the second wavelength ($\lambda_2$) may belong to a wavelength region of about 780 nm to about 840 nm and the other of the first wavelength ($\lambda_1$) or the second wavelength ($\lambda_2$) may belong to a wavelength region of about 910 nm to about 970 nm.

For example, one of the first wavelength ($\lambda_1$) or the second wavelength ($\lambda_2$) may belong to a wavelength region of about 800 nm to about 830 nm and the other of the first wavelength ($\lambda_1$) or the second wavelength ($\lambda_2$) may belong to a wavelength region of about 930 nm to about 950 nm.

For example, one of the first wavelength ($\lambda_1$) or the second wavelength ($\lambda_2$) may belong to a wavelength region of about 805 nm to about 815 nm and the other of the first wavelength ($\lambda_1$) or the second wavelength ($\lambda_2$) may belong to a wavelength region of about 935 nm to about 945 nm.

For example, one of the first wavelength ($\lambda_1$) or the second wavelength ($\lambda_2$) may about 810 nm and the other of the first wavelength ($\lambda_1$) or the second wavelength ($\lambda_2$) may be about 940 nm.

The organic sensor 400 according to some example embodiments includes a dual bandpass filter 95, a first infrared light sensor 100A, an insulation layer 80, and a semiconductor substrate 110 integrated with a second infrared light sensor 120, such that the second infrared light sensor 120 is at least partially embedded within the semiconductor substrate 110. As shown in FIG. 4, the first infrared light sensor 100A and the second infrared light sensor 120 may be stacked, e.g., may overlap in a vertical direction that is perpendicular to the top surface 110S of the semiconductor substrate 110.

As shown in FIG. 4, dual bandpass filter 95 may be disposed on a front side of the organic sensor 400 and may selectively transmit infrared light (e.g., light in an infrared wavelength region) including the first wavelength ($\lambda_1$) and infrared light including the second wavelength ($\lambda_2$) and may block and/or absorb other light. Herein, other light may include light in an ultraviolet (UV) and visible region.

The first infrared light sensor 100A includes a first electrode 10, an active layer 30, and a second electrode 20. As shown in FIG. 4, the first infrared light sensor 100A may be the same as the photoelectric device 100 according to some example embodiments, including the example embodiments described with reference to FIG. 1, but it will be understood that, in some example embodiments, the first infrared light sensor 100A may be the same as the photoelectric device 200 according to some example embodiments, including the example embodiments described with reference to FIG. 2.

As shown in FIG. 4, the second infrared light sensor 120 may be integrated in the semiconductor substrate 110 and may be a photo-sensing device. The semiconductor substrate 110 (e.g., encompassed within a volume space defined by outer surfaces of the semiconductor substrate 110) may be for example a silicon substrate and may be integrated with the second infrared light sensor 120, the charge storage 55, and a transmission transistor (not shown).

The second infrared light sensor 120 may be a photodiode (e.g., a silicon-based photodiode) and may sense (e.g., absorb) entered light, and sensed information is transferred by the transmission transistor. Herein, the light entered into the second infrared light sensor 120 is light that passes through (e.g., is selectively transmitted by) the dual band-pass filter 95 and the first infrared light sensor 100A and may be infrared light in a particular (or, alternatively, predetermined) region including the second wavelength ($\lambda_2$). All infrared light in a particular (or, alternatively, predetermined) region including the first wavelength ($\lambda_1$) may be absorbed by the active layer 30 and may not reach the second infrared light sensor 120. In this case, a separate filter for wavelength selectivity with respect to the light entered into the second infrared light sensor 120 is not separately needed. However, for the time when all infrared light in a particular (or, alternatively, predetermined) region including the first wavelength ($\lambda_1$) is not absorbed by active layer 30, a filter between the first infrared light sensor 100A and the second infrared light sensor 120 may be further disposed.

Accordingly, in the organic sensor 400, the first infrared light sensor 100A may be understood to include a photoelectric device (e.g., photoelectric device 100 and/or 200) configured to sense (e.g., selectively absorb and/or convert (into electrical signals, e.g., photoelectrically convert)) light in a first near-infrared wavelength region of incident light (e.g., a first near-infrared wavelength region including the first wavelength ($\lambda_1$)), and the second infrared light sensor 120 may be understood to be an additional sensor configured to selectively absorb and/or convert (into electrical signals, e.g., photoelectrically convert) light in a separate wavelength region of incident light (e.g., a second near-infrared wavelength region that is different from the first near-infrared wavelength region and includes the second wavelength ($\lambda_2$) and excludes the first wavelength ($\lambda_1$)).

The organic sensor according to some example embodiments may include two infrared light sensors respectively performing separately functions and thus may work as a combination sensor. In addition, two sensors performing separately functions are stacked in each pixel, and thus the number of pixel performing functioning of each sensor is twice increased while maintaining a size and resultantly, sensitivity may be much improved.

As noted above with reference to FIG. 1, the active layer 30, or any portion of the photoelectric device 100 and/or 200, may include the aforementioned near-infrared absorber and thus may have improved sensitivity to and/or absorbance of near-infrared light, such that the operational performance and/or efficiency of the organic sensor 400 in absorbing and/or photoelectrically converting incident near-infrared light into electrical signals (e.g., photoelectric conversion performance and/or efficiency) may be improved. In some example embodiments, the second infrared sensor 120 may include the aforementioned near-infrared absorber and thus may have improved sensitivity to and/or absorbance of near-infrared light, such that the operational performance and/or efficiency of the organic sensor 400 in absorbing and/or converting incident near-infrared light into electrical signals (e.g., photoelectric conversion performance and/or efficiency) may be improved.

Figure 5:
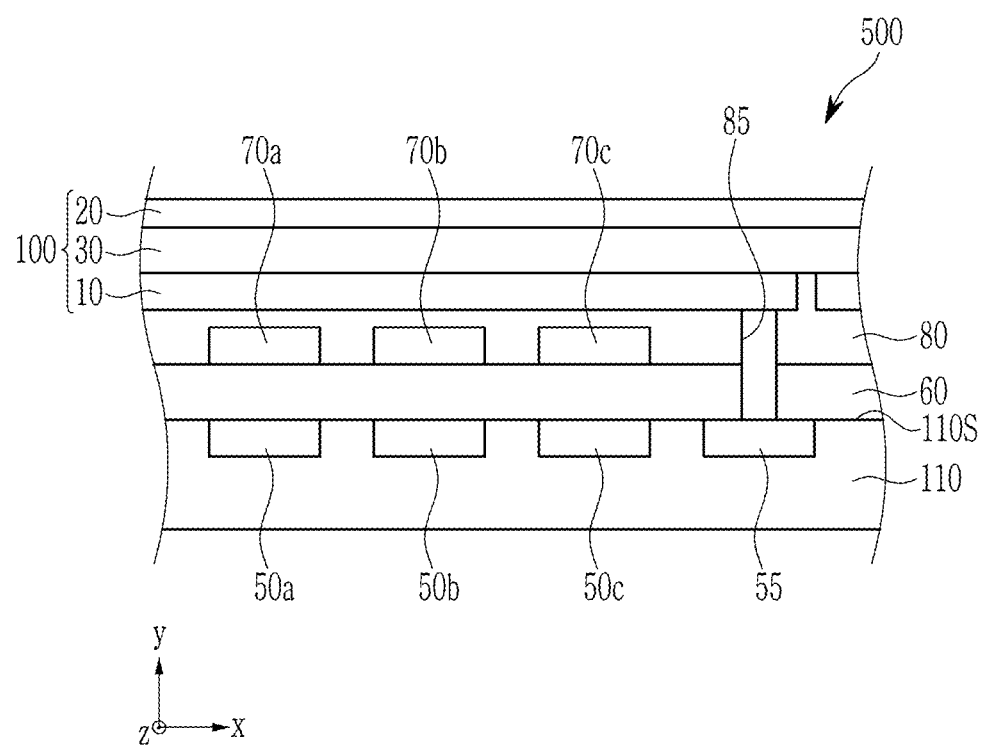
FIG. 5 is a cross-sectional view showing an organic sensor according to some example embodiments.

FIG. 5 is a cross-sectional view showing an example of an organic sensor according to some example embodiments.

An organic sensor according to some example embodiments may be an organic CMOS image sensor.

Referring to FIG. 5, an organic sensor 500 according to some example embodiments includes a semiconductor substrate 110 integrated with photo-sensing devices (e.g., photodiodes, including silicon-based photodiodes) 50a, 50b, and 50c, a transmission transistor (not shown), and a charge storage 55, a lower insulation layer 60, color filter layers 70a, 70b, and 70c, an upper insulation layer 80, and a photoelectric device 100.

The semiconductor substrate 110 may be integrated with photo-sensing devices 50a, 50b, and 50c such that the photo-sensing devices 50a, 50b, and 50c are at least partially embedded within the semiconductor substrate 110 and are vertically overlapped by the photoelectric device 100 in the vertical direction that is perpendicular to the top surface 110S, a transmission transistor (not shown), and a charge storage 55. The photo-sensing devices 50a, 50b, and 50c may be photodiodes (e.g., silicon-based photodiodes) that may be configured to sense (e.g., selectively absorb and/or convert (into electrical signals, e.g., photoelectrically convert)) light in different visible wavelength regions.

The photo-sensing devices 50a, 50b, and 50c, the transmission transistor, and/or the charge storage 55 may be integrated in each pixel. For example, the photo-sensing device 50a may be included in a red pixel, the photo-sensing device 50b may be included in a green pixel, and the photo-sensing device 50c may be included in a blue pixel.

The photo-sensing devices 50a, 50b, and 50c sense (e.g., selectively absorb and/or convert (into electrical signals, e.g., photoelectrically convert)) incident light, the information sensed by the photo-sensing devices may be transferred by the transmission transistor, the charge storage 55 is electrically connected to the photoelectric device 100, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing devices 50a and 50b.

The lower insulation layer 60 is formed on the metal wire and the pad. The lower insulation layer 60 may include a same or different material composition as the insulation layer 80.

Color filters 70a, 70b, and 70c are formed on the lower insulation layer 60. The color filters 70a, 70b, and 70c includes a red filter 70a formed in a red pixel, a green filter 70b formed in a green pixel, and a blue filter 70c formed in a blue pixel.

The insulation layer (also referred to as upper insulation layer) 80 is formed on the color filters 70a, 70b, and 70c.

The insulation layer 80 eliminates steps caused by the color filters 70a, 70b, and 70c and planarizes the surface.

The aforementioned photoelectric device 100 is formed on the insulation layer 80. As described above, the photoelectric device 100 includes a first electrode 10, an active layer 30, and a second electrode 20. Even though a structure in which the first electrode 10, the active layer 30 and the second electrode 20 are sequentially stacked is shown as an example in the drawing, the present disclosure is not limited to this structure, and the second electrode 20, the active layer 30, and the electrodes 10 may be arranged in this order.

The first electrode 10 and the second electrode 20 may both be transparent electrodes, and the active layer 30 is the same as described above. The active layer 30 may selectively absorb and/or convert (into electrical signals, e.g., photoelectrically convert) light in a near-infrared wavelength region. As noted above with regard to photoelectric devices 100 and 200, any portion of the photoelectric device 100 (e.g., first electrode 10, second electrode 20, and/or active layer 30) may include the aforementioned near-infrared absorber.

Incident light from the side of the second electrode 20 may be photoelectrically converted by mainly absorbing light in a near infra-red wavelength region in the active layer 30. Light in the remaining wavelength region may pass through the first electrode 10 and the color filters 70a, 70b, and 70c, the light in a red wavelength region passing through the color filter 70a may be sensed by the photo-sensing device 50a, the light in a green wavelength region passing through the color filter 70b may be sensed by the photo-sensing device 50b, and the light in a blue wavelength region passing through the color filter 70c may be sensed by the photo-sensing device 50c.

As noted above with reference to FIG. 1, the active layer 30 may include the aforementioned near-infrared absorber and thus may have improved sensitivity to near-infrared light, such that the operational performance and/or efficiency of the organic sensor 500 in absorbing and/or converting incident near-infrared light into electrical signals (e.g., photoelectric conversion performance and/or efficiency) may be improved.

Accordingly, where an organic sensor includes a photoelectric device that includes the near-infrared absorber and is configured to selectively absorb and/or convert (into electrical signals, e.g., photoelectrically convert) light in a first near-infrared wavelength region, the organic sensor may include an additional sensor that includes a plurality of photodiodes (e.g., photo-sensing devices 50a, 50b, 50c) at least partially embedded within the semiconductor substrate and configured to selectively absorb and/or convert (into electrical signals, e.g., photoelectrically convert) light in separate visible wavelength regions (e.g., red, blue, and/or green light).

Figure 6:
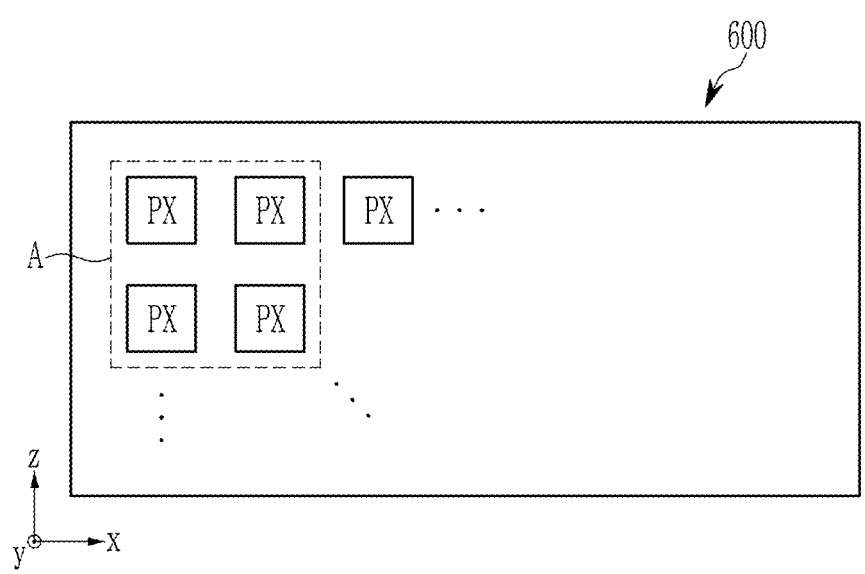
FIG. 6 is a schematic view showing an example of a pixel array of an organic sensor according to some example embodiments.

FIG. 6 is a schematic view showing an example of a pixel array of an organic sensor according to some example embodiments.

Referring to FIG. 6, an organic sensor 600 according to some example embodiments includes a plurality of pixels (PX) and the plurality of pixels (PX) may have a matrix array repeatedly arranged along rows and columns. The plurality of pixels (PX) may form ("at least partially comprise") a unit pixel group (A) of for example a 2×2 array of pixels as shown in FIG. 6. However, an arrangement of the pixels are not limited thereto but variously modified, and the unit pixel group (A) may be variously modified into different arrays of pixels, including a 3×3 array, a 4×4 array, or the like, besides the 2×2 array.

At least a part of the pixels may include a plurality of sensors having different functions inside one pixel, and the plurality of sensors may be stacked therein. In some example embodiments, each pixel (PX) may include two or more organic sensors that are configured to sense (e.g., absorb) light in different wavelength regions ("wavelength spectra of light") in relation to each other, and the organic sensors configured to sense the light in different wavelength regions each other may be stacked in a direction that is perpendicular (e.g., perpendicular within manufacturing tolerances and/or material tolerances) to a top surface 110S of a substrate of the organic sensor 600, as shown in at least FIG. 7 (e.g., a Y direction). Herein, the light of the different wavelength regions may be respectively selected from a visible wavelength region; an infrared wavelength region including a near-infrared wavelength region; and an ultraviolet (UV) wavelength region.

It will be understood that any of the organic sensors according to any of the example embodiments herein may have the pixel array structure of organic sensor 600 as shown in FIG. 6.

Figure 7:
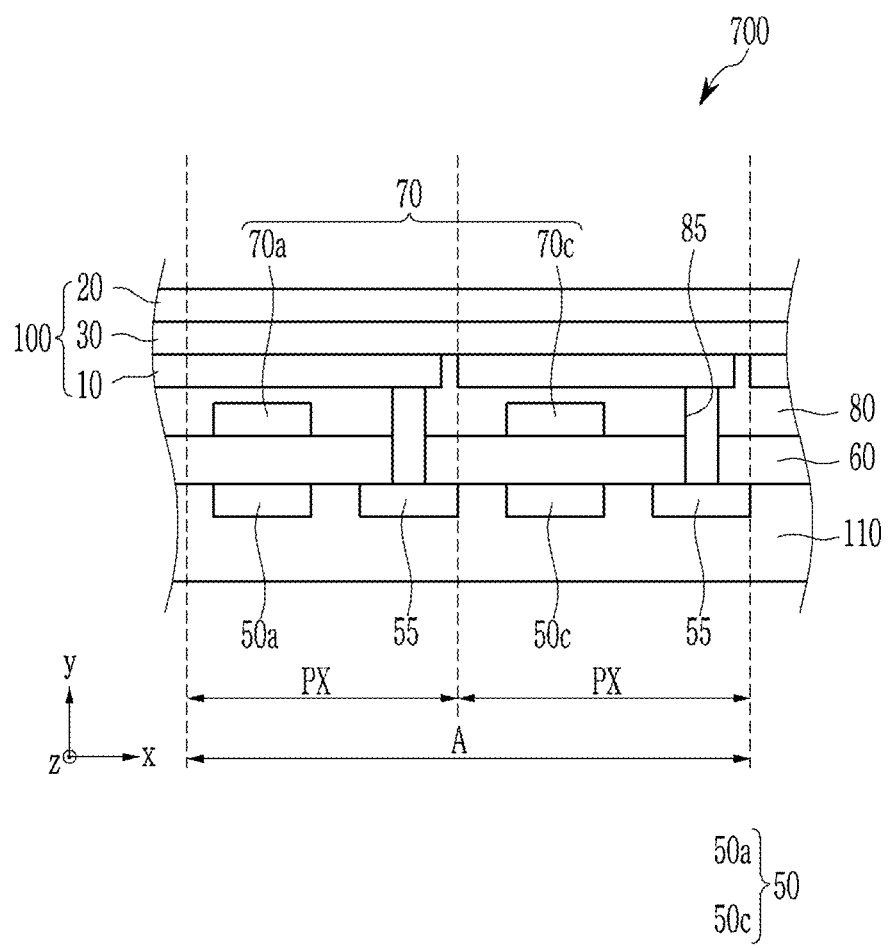
FIG. 7 is a cross-sectional view showing an organic sensor according to some example embodiments.

FIG. 7 is a cross-sectional view showing an organic sensor according to some example embodiments.

Referring to FIG. 7, an organic sensor 700 according to some example embodiments includes a semiconductor substrate 110 integrated with a visible sensor 50 that includes photo-sensing devices 50a and 50c, a transmission transistor (not shown), and a charge storage 55; a lower insulation layer 60; a color filter layer 70; an insulation layer 80 (also referred to as an upper insulation layer when present with the lower insulation layer 60 in a same organic sensor); and a photoelectric device 100.

The semiconductor substrate 110 may be a silicon substrate, and is integrated with the photo-sensing devices 50a and 50c, the transmission transistor (not shown), and the charge storage 55. The photo-sensing devices 50a and 50c may be photodiodes (e.g., silicon-based photodiodes).

The photo-sensing devices 50a and 50c may sense light, the information sensed by the photo-sensing devices may be transferred by the transmission transistor, the charge storage 55 is electrically connected to the photoelectric device 100, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but is not limited thereto. However, it is not limited to the structure, and the metal wire and pad may be disposed under the photo-sensing devices 50a and 50c.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a red filter 70a formed in the red pixel and a blue filter 70c formed in the blue pixel. In the example embodiments shown in FIG. 7, a green filter is not included, but a green filter may be further included.

The insulation layer 80 is formed on the color filter layer 70. The insulation layer 80 eliminates a step caused by the color filter layer 70 and smoothens the surface. The insulation layer 80 and lower insulation layer 60 may include a contact hole (not shown) exposing a pad, and a through hole (e.g., trench 85) exposing the charge storage 55 of a green pixel.

The photoelectric device 100 is formed on the insulation layer 80. The photoelectric device 100 includes a first electrode 10 and a second electrode 20 facing each other and an active layer 30 disposed between the first electrode 10 and the second electrode 20. The photoelectric device 100 may be the same as the photoelectric device 100 of FIG. 1. In some example embodiments, the photoelectric device 100 of FIG. 7 may be replaced with the photoelectric device 200 of FIG. 2.

The first electrode 10 and the second electrode 20 may be all light-transmitting electrodes and the active layer 30 may selectively absorb and/or convert (into electrical signals, e.g., photoelectrically convert) light in a near-infrared wavelength region. In some example embodiments, including the example embodiments shown in FIG. 7, the active layer 30 may additionally selectively absorb and/or convert (into electrical signals, e.g., photoelectrically convert) light in a visible wavelength region (e.g., red light).

Focusing lens (not shown) may be further formed on the photoelectric device 100. The focusing lens may control a direction of incident light and gather the light in one region. The focusing lens may have a shape of, for example, a cylinder or a hemisphere, but is not limited thereto.

In FIG. 7, a structure where the photoelectric device 100 selectively absorbing light in a near-infrared wavelength region is stacked on the semiconductor substrate 110 is illustrated, but the present disclosure is not limited thereto. Among the light incident on the organic sensor 700 at a top surface of the photoelectric device 100, at least light in a near-infrared wavelength region may be mainly absorbed in the active layer 30 and photoelectrically converted, and light in a visible (e.g., blue, green, and/or red) wavelength region may pass through the first electrode 10 and be sensed by the photo-sensing devices 50a and 50c.

Figure 8:
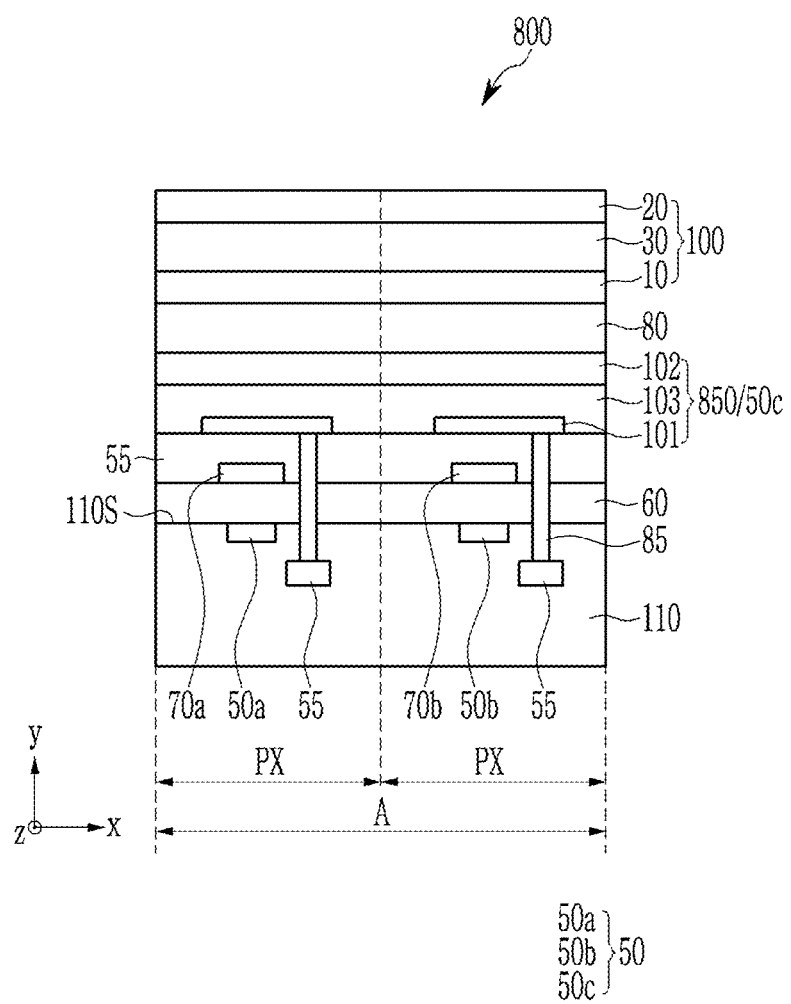
FIG. 8 is a cross-sectional view showing an organic sensor according to some example embodiments.

FIG. 8 is a cross-sectional view showing an organic sensor according to some example embodiments.

Referring to FIG. 8, the organic sensor 800 according to some example embodiments includes a visible light sensor 50, and the photoelectric device 100 as described above.

Referring to FIG. 8, in the organic sensor 800 according to some example embodiments, the visible light sensor 50 may be a combination of a photodiode integrated in the semiconductor substrate 110 and a photoelectric device disposed on the semiconductor substrate 110, and the photoelectric device 100 may be a separate photoelectric device.

Accordingly, where an organic sensor includes a photoelectric device (e.g., 100) that includes the near-infrared absorber and is configured to selectively absorb and/or convert (into electrical signals, e.g., photoelectrically convert) light in a first near-infrared wavelength region, and an additional sensor (e.g., 50a and/or 50b) configured to selectively absorb and/or convert (into electrical signals, e.g., photoelectrically convert) light in a separate wavelength region of incident light, the organic sensor may further include an additional photoelectric device (e.g., 50c) on the semiconductor substrate, the additional photoelectric device being between the photoelectric device 100 and the semiconductor substrate 110, the additional photoelectric device configured to selectively absorb and/or convert (into electrical signals, e.g., photoelectrically convert) light in an additional wavelength region of incident light that is different from the first near-infrared wavelength region and different from the separate wavelength region(s) absorbed by the additional sensor 50a and/or 50b.

In the semiconductor substrate 110, the blue photo-sensing device 50a, the red photo-sensing device 50b, the charge storage 55, and a transmission transistor (not shown) are integrated. The blue photo-sensing device 50a and the red photo-sensing device 50b are photodiodes (e.g., silicon-based photodiodes) and spaced apart from each other in a horizontal direction of the semiconductor substrate 110. The blue photo-sensing device 50a is integrated in a blue pixel, and the red photo-sensing device 50b is integrated in a red pixel.

On the semiconductor substrate 110, the lower insulation layer 60 and the color filter layer 70 are formed. The color filter layer 70 includes a blue filter 70a overlapped with the blue photo-sensing device 50a and a red filter 70b overlapped with the red photo-sensing device 50b.

An intermediate insulation layer 65 is formed on the color filter layer 70. The lower insulation layer 60 and the intermediate insulation layer 65 may have a through hole (e.g., trench 85) exposing the charge storage 140. The through hole (e.g., trench 85) may be filled with fillers. At least one of the lower insulation layer 60 or intermediate insulation layer 65 may be omitted.

On the intermediate insulation layer 65, the additional photoelectric device 850 is formed. In the example embodiments shown in FIG. 8, the additional photoelectric device 850 is also green sensor 50c, but it will be understood that in some example embodiments the additional photoelectric device 850 may be configured to sense (e.g., selectively absorb and/or convert (into electrical signals, e.g., photoelectrically convert)) light in a wavelength region that is different from the green wavelength region and may be a non-visible wavelength region (e.g., a second near-infrared wavelength region) that is different from the first near-infrared wavelength region sensed by the photoelectric device 100. The additional photoelectric device 850 includes a first electrode (lower electrode) 101 and a second electrode (upper electrode) 102 facing each other, and an active layer 103 between the first electrode 101 and the second electrode 102. One of the first electrode 101 and the second electrode 102 is an anode and the other is a cathode.

Both of the first electrode 101 and the second electrode 102 may be a light-transmitting electrode, and the light-transmitting electrode may be made of, in some example embodiments, a transparent conductor such as indium tin oxide (ITO) or indium zinc oxide (IZO), or may be a metal thin layer having a thin thickness of several nanometers or several tens of nanometers or a metal thin layer having a thin thickness of several nanometers to several tens of nanometers doped with a metal oxide.

The active layer 103 may have a composition similar to that of the active layer 30 of photoelectric device 100 and/or 200, and may include the near-infrared absorber. The active layer 103 may be a photoelectric conversion layer configured to selectively absorb and/or convert (into electrical signals, e.g., photoelectrically convert) light in at least a portion of a wavelength region (e.g., wavelength spectrum of the light) and/or convert it (e.g., the absorbed light) into an electrical signal. The active layer 103 may for example convert at least a portion of light in a green wavelength region (hereinafter, referred to as "green light"), light in a blue wavelength region (hereinafter, referred to as "blue light"), light in a red wavelength region (hereinafter, referred to as "red light"), light in an infrared wavelength region (hereinafter, referred to as "infrared light"), light in an ultraviolet wavelength region (hereinafter, referred to as "ultraviolet light"), or any combination thereof, or the like, into an electrical signal.

For example, the active layer 103 may be configured to selectively absorb and/or convert (into electrical signals, e.g., photoelectrically convert) at least one of the green light, the blue light, the red light, the infrared light, or the ultraviolet light. Herein, the selective absorption of at least one from the green light, the blue light, the red light, the infrared light, or the ultraviolet light means that a light-absorption spectrum has a peak absorption wavelength ($\lambda_{max}$) in one of about 500 nm to about 600 nm, greater than or equal to about 380 nm and less than about 500 nm, greater than about 600 nm and less than or equal to about 700 nm, and greater than about 700 nm and less than or equal to about 3000 nm and a light-absorption spectrum in the corresponding wavelength region is remarkably higher than those in the other wavelength regions.

The active layer 103 may include at least one p-type semiconductor and at least one n-type semiconductor which form a pn junction and may produce excitons by receiving light from outside and then separate the produced excitons into holes and electrons. The p-type semiconductor and the n-type semiconductor may be independently light-absorbing materials, and for example at least one of the p-type semiconductor or the n-type semiconductor may be an organic light-absorbing material. For example, at least one of the p-type semiconductor or the n-type semiconductor may be a wavelength-selective light-absorbing material that selectively absorbs light in a particular (or, alternatively, predetermined) wavelength region, and for example at least one of the p-type semiconductor or the n-type semiconductor may be a wavelength-selective organic light-absorbing material. The p-type semiconductor and the n-type semiconductor may have a peak absorption wavelength ($\lambda_{max}$) in the same wavelength region or in a different wavelength region, among a green wavelength region, a blue wavelength region, a red wavelength region, and an infrared wavelength region. For example, the p-type semiconductor may be an organic material having a core structure including an electron donating moiety, a pi conjugation linking group, and an electron accepting moiety. The p-type semiconductor may be for example represented by Chemical Formula 2, but is not limited thereto.

EDG-HA-EAG                    [Chemical Formula 2]

In Chemical Formula 2, HA may be a C2 to C30 heterocyclic group having at least one of S, Se, Te, or Si, EDG may be an electron-donating group, and EAG may be an electron accepting group. For example, the p-type semiconductor represented by Chemical Formula 2 may be for example represented by Chemical Formula 2A.

[Chemical Formula 2A]

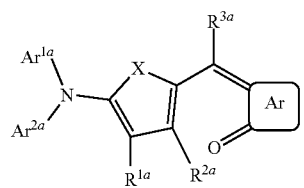

In Chemical Formula 2A, X may be S, Se, Te, SO, $SO_2$, or $SiR^aR^b$, Ar may be a substituted or unsubstituted C6 to C30 arylene group, a substituted or unsubstituted C3 to C30 heterocyclic group, or a fused ring of the foregoing two or more, Ar1a and Ar2a may independently be a substituted or unsubstituted C6 to C30 aryl group or a substituted or unsubstituted C3 to C30 heteroaryl group, Ar1a and Ar2a may independently be present alone or may be linked with each other to form a fused ring, and $R^{1a}$ to $R^{3a}$, $R^a$, and $R^b$ may independently be hydrogen, deuterium, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group.

For example, in Chemical Formula 2A, Ar1a and Ar2a may independently be one of a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group. For example, Aria and Ar2a of Chemical Formula 2A may be linked with each other to form a ring or for example, $Ar^{1a}$ and $Ar^{2a}$ may be linked with each other by one of a single bond, —$(CR^gR^h)_{n2}$— (n2 is 1 or 2), —O—, —S—, —Se—, —N═, —NR'—, —$SiR^jR^k$—, and —$GeR^lR^m$— to form a ring. Herein, $R^g$ to $R^m$ may independently be hydrogen, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group.

For example, the p-type semiconductor represented by Chemical Formula 2 may be for example represented by Chemical Formula 2B.

[Chemical Formula 2B]

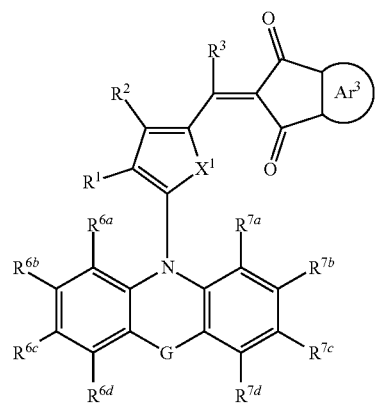

In Chemical Formula 2B, $X^1$ may be Se, Te, O, S, SO, or $SO_2$, Ara may be a substituted or unsubstituted C6 to C30 arylene group, a substituted or unsubstituted C3 to C30 heterocyclic group, or a fused ring of the foregoing two or more, $R^1$ to $R^3$ may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, and a combination thereof, G may be one of a single bond, —O—, —S—, —Se—, —N═, —(CR$^f$R$^g$)$_k$—, —NR''—, —SiR$^i$R$^j$—, —GeR$^k$R$^l$—, —(C(R$^m$)═C(R$^n$))—, and SnR$^o$R$^p$, wherein R$^f$, R$^g$, R$^h$, R$^i$, R$^j$, R$^k$, R$^l$, R$^m$, R$^n$, R$^o$, and R$^p$ may independently be one of hydrogen, a halogen, a substituted or unsubstituted C1 to C10 alkyl group, a substituted or unsubstituted C1 to C10 alkoxy group, and a substituted or unsubstituted C6 to C12 aryl group, R$^f$ and R$^g$, R$^i$ and R$^j$, R$^k$ and R$^l$, R$^m$ and R$^n$, and R$^o$ and R$^p$ may independently be present alone or may be linked with each other to provide a ring, and k may be 1 or 2, R$^{6a}$ to R$^{6d}$ and R$^{7a}$ to R$^{7d}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, and a combination thereof, R$^{6a}$ to R$^{6d}$ may independently be present alone or adjacent two thereof may be linked with each other to form a fused ring, and R$^{7a}$ to R$^{7d}$ may independently be present alone or adjacent two thereof may be linked with each other to form a fused ring.

For example, Ara of Chemical Formula 2B may be benzene, naphthylene, anthracene, thiophene, selenophene, tellurophene, pyridine, pyrimidine, or a fused ring of the foregoing two or more. The n-type semiconductor may be for example fullerene or a fullerene derivative, but is not limited thereto.

The active layer 103 may be an intrinsic layer (an I layer) wherein the p-type semiconductor and the n-type semiconductor are blended as a bulk heterojunction. Herein, the p-type semiconductor and the n-type semiconductor may be blended in a volume ratio of about 1:9 to about 9:1, for example about 2:8 to about 8:2, about 3:7 to about 7:3, about 4:6 to about 6:4, or about 5:5. The active layer 103 may include a bi-layer including a p-type layer including the aforementioned p-type semiconductor and an n-type layer including the aforementioned n-type semiconductor. Herein, a thickness ratio of the p-type layer and the n-type layer may be about 1:9 to about 9:1, for example about 2:8 to about 8:2, about 3:7 to about 7:3, about 4:6 to about 6:4, or about 5:5. The active layer 103 may further include a p-type layer and/or an n-type layer in addition to the intrinsic layer. The p-type layer may include the aforementioned p-type semiconductor and the n-type layer may include the aforementioned n-type semiconductor. For example, they may be included in various combinations of p-type layer/I layer, I layer/n-type layer, p-type layer/I layer/n-type layer, and the like.

In the example embodiments shown in FIG. 8, the active layer 103 is configured to selectively absorb and/or convert (into electrical signals, e.g., photoelectrically convert) green light, but example embodiments are not limited thereto, and in some example embodiments the active layer 103 may selectively absorb and/or convert (into electrical signals, e.g., photoelectrically convert) blue light, red light, or any visible wavelength region of light, or any non-visible wavelength region of light (e.g., a second wavelength region of near-infrared light that is selectively transmitted by the photoelectric device 100).

Figure 9:
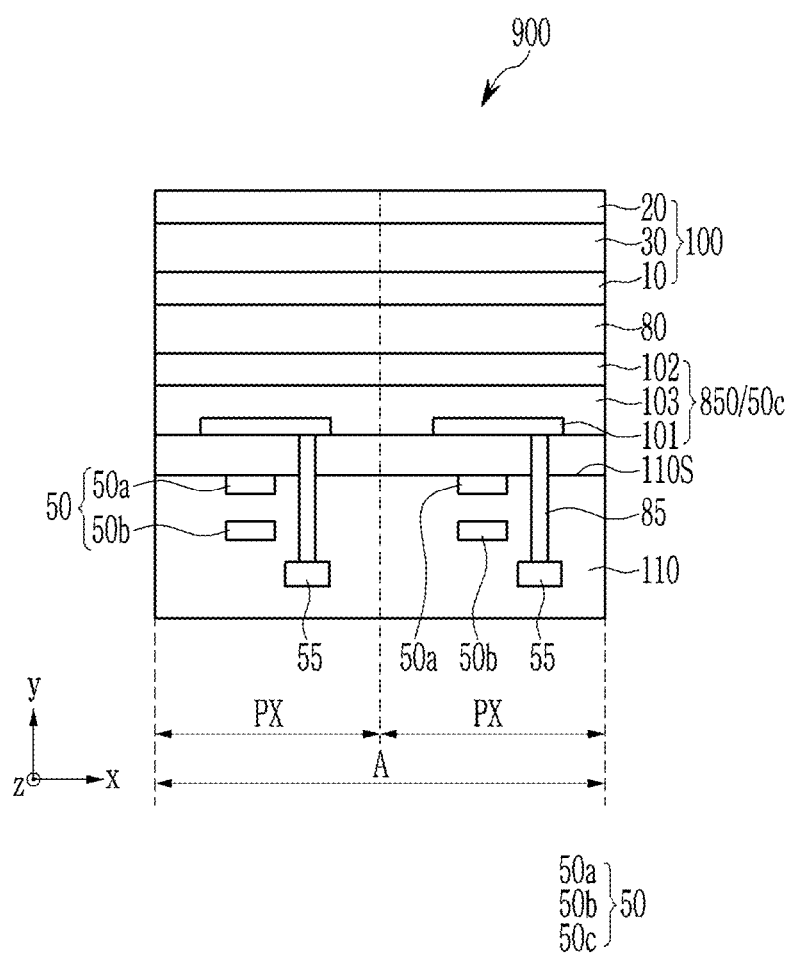
FIG. 9 is a cross-sectional view showing an organic sensor according to some example embodiments.

FIG. 9 is a cross-sectional view showing an organic sensor according to some example embodiments.

Referring to FIG. 9, the organic sensor 900 according to some example embodiments includes the visible light sensor 50, and the photoelectric device 100 like that of some example embodiments. The visible light sensor 50 includes the blue photo-sensing device 50a and the red photo-sensing device 50b integrated in the semiconductor substrate 110 and an additional photoelectric device 850 that includes a green sensor 50c disposed on the semiconductor substrate 110, wherein the blue photo-sensing device 50a and the red photo-sensing device 50b may be photodiodes (e.g., silicon-based photodiodes), and the additional photoelectric device 850 may be a green sensor 50c that may be the same as, or different than, the green sensor 50c shown in FIG. 8. The additional photoelectric device 850 includes a first electrode 101, active layer 103, and a second electrode (upper electrode) 102, and the photoelectric device 100 includes a first electrode 10, an active layer 30, and a second electrode 20.

However, in the organic sensor 900 according to some example embodiments, the blue photo-sensing device 50a and the red photo-sensing device 50b integrated in the semiconductor substrate 110 are stacked in a vertical direction (e.g., perpendicular to the top surface 110S of the semiconductor substrate 110). The blue photo-sensing device 50a and the red photo-sensing device 50b may be configured to selectively absorb and/or convert (into electrical signals, e.g., photoelectrically convert) light in each wavelength region depending on a stacking depth and thus sense it. In other words, the red photo-sensing device 50b configured to selectively absorb and/or convert (into electrical signals, e.g., photoelectrically convert) red light in a long wavelength region is disposed deeper from the surface of the semiconductor substrate 110 than the blue photo-sensing device 50a configured to selectively absorb and/or convert (into electrical signals, e.g., photoelectrically convert) blue light in a short wavelength region. In this way, the color filter layer 70 may be omitted by separating absorption wavelengths depending on the stacking depth.

Figure 10:
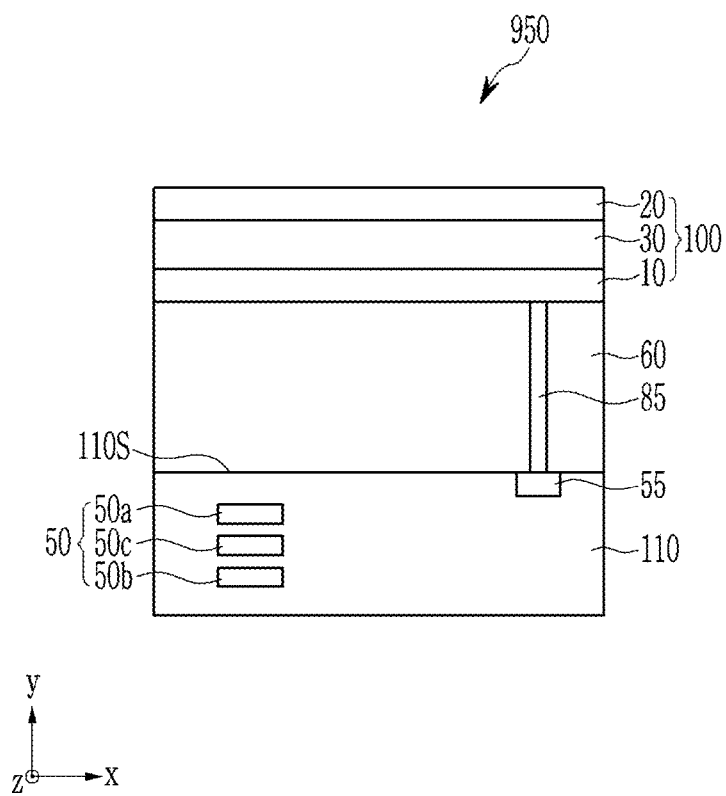
FIG. 10 is a cross-sectional view showing an organic sensor according to some example embodiments.

FIG. 10 is a cross-sectional view showing an organic sensor according to some example embodiments.

Referring to FIG. 10, the organic sensor 950 according to some example embodiments includes the visible light sensor 50, and the photoelectric device 100 like that of some example embodiments. The visible light sensor 50 includes the blue photo-sensing device 50a, green sensor 50c, and the red photo-sensing device 50b integrated in the semiconductor substrate 110, wherein the blue photo-sensing device 50a, green sensor 50c, and the red photo-sensing device 50b may be photodiodes.

In the organic sensor 950 according to some example embodiments, the blue photo-sensing device 50a, green sensor 50c, and the red photo-sensing device 50b integrated in the semiconductor substrate 110 are stacked in a vertical direction. The blue photo-sensing device 50a, green sensor 50c, and the red photo-sensing device 50b may be configured to selectively absorb and/or convert (into electrical signals, e.g., photoelectrically convert) light in each wavelength region depending on a stacking depth from the top surface 110S and thus sense it. In other words, the red photo-sensing device 50b configured to selectively absorb and/or convert (into electrical signals, e.g., photoelectrically convert) red light in a long wavelength region is disposed deeper from the top surface 110S of the semiconductor substrate 110 than the blue photo-sensing device 50a configured to selectively absorb and/or convert (into electrical signals, e.g., photoelectrically convert) blue light in a short wavelength region, and the green sensor 50c configured to selectively absorb and/or convert (into electrical signals, e.g., photoelectrically convert) green light in a medium wavelength region is disposed deeper from the top surface 110S of the semiconductor substrate 110 than the blue photo-sensing device 50*a* and closer to the top surface 110S of the semiconductor substrate 110 than the red photo-sensing device 50*b*. In this way, the color filter layer 70 may be omitted by separating absorption wavelengths depending on the stacking depth.

Figure 11:
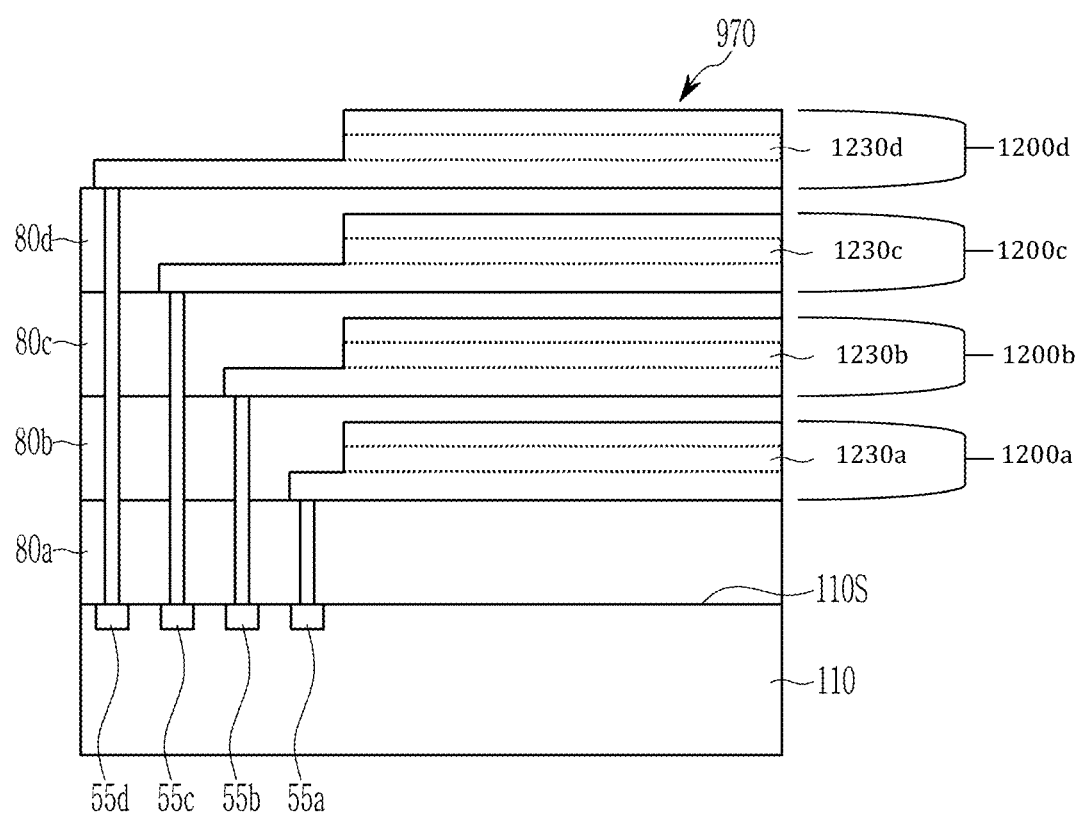
FIG. 11 is a cross-sectional view showing an organic sensor according to some example embodiments.

FIG. 11 is a cross-sectional view showing an organic sensor according to some example embodiments.

Referring to FIG. 11, the organic sensor 970 according to some example embodiments includes a first photoelectric device (e.g., infrared/near infrared photoelectric device 1200*d*) configured to selectively absorb and/or convert (into electrical signals, e.g., photoelectrically convert) light in an infrared/near infrared wavelength spectrum of incident light (e.g., a first near-infrared wavelength region), and at least one additional photoelectric device (e.g., 1200*a*-1200*c*) vertically stacked between the first photoelectric device and a semiconductor substrate (e.g., 110), each separate photoelectric device of the at least one additional photoelectric device including a separate photoelectric conversion layer and configured to selectively absorb and/or convert (into electrical signals, e.g., photoelectrically convert) a separate (e.g., respective) wavelength region of incident light that is different from the first near-infrared wavelength region and which may be a separate visible and/or non-visible wavelength region. For example, as shown in FIG. 11, the organic sensor 970 may include additional photoelectric devices that include a red photoelectric device configured to selectively absorb and/or convert (into electrical signals, e.g., photoelectrically convert) light in a red wavelength spectrum of incident light, a green photoelectric device configured to selectively absorb and/or convert (into electrical signals) light in a green wavelength spectrum of incident light, and a blue photoelectric device configured to selectively absorb and/or convert (into electrical signals) light in a blue wavelength spectrum of incident light, and they are stacked in the vertical direction (e.g., Z-direction).

Accordingly, it will be understood that, as shown in FIG. 11, the organic sensor 970 may include a plurality of photoelectric devices 1200*a*-1200*d* that are stacked vertically on the semiconductor substrate 110, such that the plurality of photoelectric devices 1200*a*-1200*d* overlap each other in a direction extending perpendicular to a top surface 110S of the semiconductor substrate 110. While the organic sensor 970 includes multiple additional photoelectric devices 1200*a*-1200*c* in addition to the first photoelectric device (e.g., fourth photoelectric device 1200*d*) configured to selectively absorb and/or convert light in the first near-infrared wavelength region, it will be understood that in some example embodiments the organic sensor 970 may be limited to a single additional photoelectric device (e.g., any of 1200*a* to 1200*c*) between the photoelectric device 1200*d* and the semiconductor substrate 110.

The organic sensor 970 according to some example embodiments includes a semiconductor substrate 110, a lower insulation layer 80*a*, an intermediate insulation layer 80*b*, another intermediate insulation layer 80*c*, an upper insulation layer 80*d*, a first photoelectric device 1200*a*, a second photoelectric device 1200*b*, a third photoelectric device 1200*c*, and a fourth photoelectric device 1200*d*. In some example embodiments, the fourth photoelectric device 1200*d* may be referred to as a first photoelectric device configured to selectively absorb and/or convert (into electrical signals, e.g., photoelectrically convert) light in a first near-infrared wavelength region, and the first to third photoelectric devices 1200*a* to 1200*c* may be collectively referred to as at least one additional photoelectric device configured to selectively absorb and/or convert (into electrical signals, e.g., photoelectrically convert) light in one or more separate wavelength regions different from the first near-infrared wavelength region. As shown, the first to fourth photoelectric devices 1200*a* to 1200*d* are stacked vertically on the semiconductor substrate 110, such that the first to fourth photoelectric devices 1200*a* to 1200*d* overlap each other in a direction extending perpendicular to a top surface 110S of the semiconductor substrate 110.

The semiconductor substrate 110 may be a silicon substrate, and is integrated with the transmission transistor (not shown) and charge storages.

The first through third photoelectric devices 1200*a*-1200*c* may have a same structure as the additional photoelectric devices 850 shown in FIGS. 8 and 9, except each separate photoelectric device 1200*a*-1200*c* may be configured to photoelectrically convert a separate wavelength region of visible and/or non-visible (e.g., near-infrared) light, and the photoelectric conversion layers 1230*a*-1230*c* may have the same structure and/or composition as various example embodiments (e.g., different example embodiments) of the active layer 103 and/or active layer 30 as described herein so as to be configured to selectively absorb and/or convert (into electrical signals, e.g., photoelectrically convert) different visible and/or non-visible wavelength regions of light, and may include the near-infrared absorber. The fourth photoelectric device 1200*d* may have a same structure as photoelectric device 100 of FIG. 1 and/or photoelectric device 200 of FIG. 2, and the photoelectric conversion layer 1230*d* may have a same structure and/or composition as the active layer 30 as described herein, and may include the near-infrared absorber.

The first photoelectric device 1200*a* is formed on the lower insulation layer 80*a*. The first photoelectric device 1200*a* includes a photoelectric conversion layer 1230*a*. The first photoelectric device 1200*a* may be any one of the photoelectric devices described herein according to any of the example embodiments. The photoelectric conversion layer 1230*a* may selectively absorb and/or convert (into electrical signals, e.g., photoelectrically convert) light in one of infrared, red, blue, and green wavelength spectra of incident light. For example, the first photoelectric device 1200*a* may be a blue photoelectric device.

An intermediate insulation layer 80*b* is formed on the first photoelectric device 1200*a*.

The second photoelectric device 1200*b* is formed on the intermediate insulation layer 80*b*. The second photoelectric 1200*b* includes a photoelectric conversion layer 1230*b*. The second photoelectric device 1200*b* may be any one of the photoelectric devices described herein according to any of the example embodiments. The photoelectric conversion layer 1230*b* may selectively absorb and/or convert (into electrical signals, e.g., photoelectrically convert) light in one of infrared, red, blue, and green wavelength spectra of incident light. For example, the second photoelectric device 1200*b* may be a green photoelectric device.

Another intermediate insulation layer 80*c* is formed on the second photoelectric device 1200*b*.

The third photoelectric device 1200*c* is formed on the intermediate insulation layer 80*c*. The third photoelectric device 1200*c* includes a photoelectric conversion layer 1230*c*. The third photoelectric device 1200*c* any one of the photoelectric devices described herein according to any of the example embodiments. The photoelectric conversion layer 1230*c* may selectively absorb and/or convert (into electrical signals, e.g., photoelectrically convert) light in one of infrared, red, blue, and green wavelength spectra of incident light. For example, the third photoelectric device 1200c may be a red photoelectric device.

The upper insulation layer 80d is formed on the third photoelectric device 1200c.

The lower insulation layer 80a, the intermediate insulation layers 80b and 80c, and the upper insulation layer 80d have a plurality of through holes exposing the charge storages 55a, 55b, 55c, and 55d.

The fourth photoelectric device 1200d is formed on the upper insulation layer 80d. The fourth photoelectric device 1200d includes a photoelectric conversion layer 1230d. The fourth photoelectric device 1200d may be any one of the photoelectric devices described herein according to any of the example embodiments. The photoelectric conversion layer 1230d may selectively absorb and/or convert (into electrical signals, e.g., photoelectrically convert) light in one of infrared, red, blue, or green wavelength spectra of light. For example, the fourth photoelectric device 1200d may be an infrared/near infrared photoelectric device that may include the near-infrared absorber.

In the drawing, the first photoelectric device 1200a, the second photoelectric device 1200b, the third photoelectric device 1200c, and the fourth photoelectric device 1200d are sequentially stacked, but the present disclosure is not limited thereto, and they may be stacked in various orders.

As described above, the first photoelectric device 1200a, the second photoelectric device 1200b, the third photoelectric device 1200c, and the fourth photoelectric device 1200d have a stack structure, and thus the size of an organic sensor may be reduced to realize a down-sized organic sensor.

Figure 12:
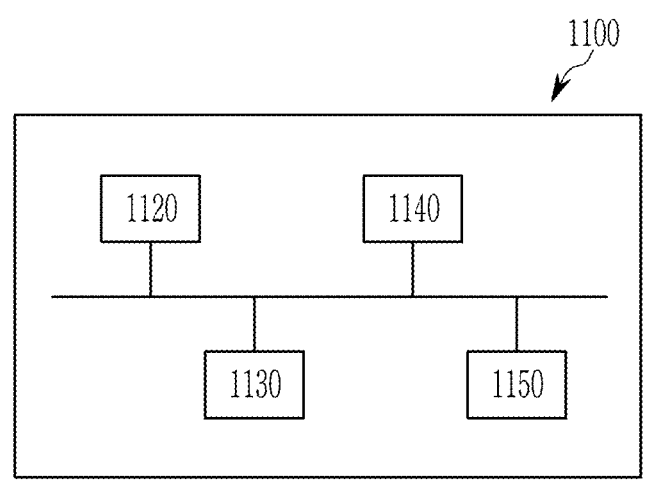
FIG. 12 is a schematic diagram of an electronic device according to some example embodiments.

FIG. 12 is a schematic diagram of an electronic device 1300 according to some example embodiments.

As shown in FIG. 12, an electronic device 1100 may include a processor 1120, a memory 1130, image sensor device 1140, and display device 1150 that are electrically coupled together via a bus 1110. The image sensor device 1140 may include any of the sensors (e.g., organic sensors, photoelectric devices, or the like) of any of the example embodiments as described herein. The memory 1130, which may be a non-transitory computer readable medium, may store a program of instructions. The processor 1120 may execute the stored program of instructions to perform one or more functions. The processor 1120 may further execute the stored program of instructions to display the generated image on display device 1150. The processor 1120 may be configured to generate an output (e.g., an image to be displayed on the display device 1150).

The organic sensor may be applied to various electronic devices, for example and the electronic devices may include for example a camera, a camcorder, a mobile phone internally having them, a display device, a security device, or a medical device, but are not limited thereto.

Figure 13:
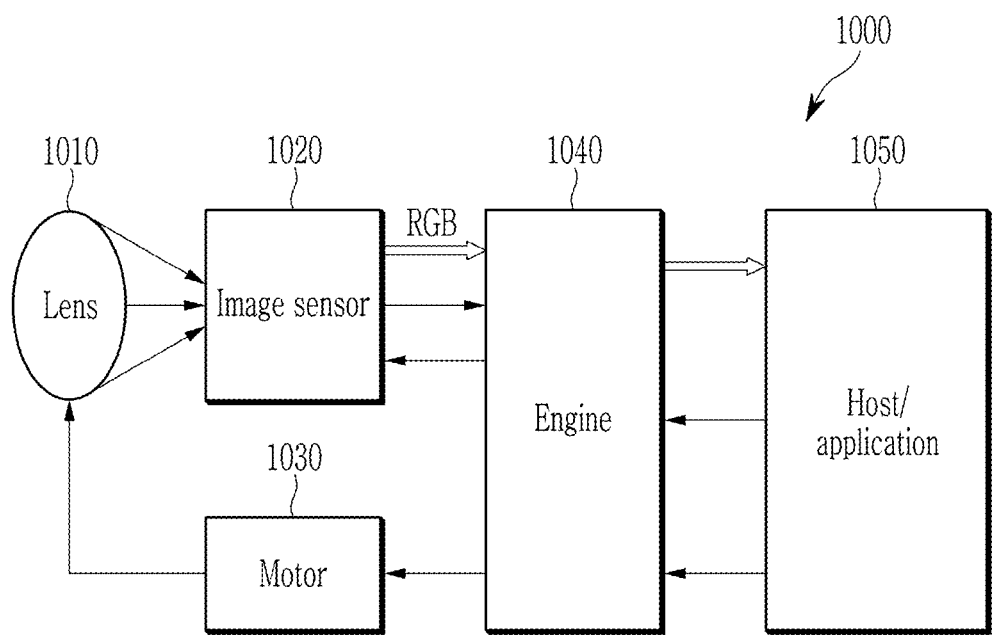
FIG. 13 is a block diagram of a digital camera including an organic sensor according to some example embodiments.

FIG. 13 is a block diagram of a digital camera including an image sensor according to some example embodiments.

Referring to FIG. 13, a digital camera 1000 includes a lens 1010, an image sensor 1020, a motor 1030, and an engine 1040. The image sensor 1020 may be one of image sensors according to some example embodiments, including the example embodiments shown in FIGS. 3 to 14.

The lens 1010 concentrates incident light on the image sensor 1020. The image sensor 1020 generates RGB data for received light through the lens 1010.

In example embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor 1030.

The engine 1040 may be connected to a host/application 1050.

One or more of the processor 1120, memory 1130, motor 1030, engine 1040, or host/application 1050 may be included in, include, and/or implement one or more instances of processing circuitry such as hardware including logic circuits, a hardware/software combination such as a processor executing software; or a combination thereof. In some example embodiments, said one or more instances of processing circuitry may include, but are not limited to, a central processing unit (CPU), an application processor (AP), an arithmetic logic unit (ALU), a graphic processing unit (GPU), a digital signal processor, a microcomputer, a field programmable gate array (FPGA), a System-on-Chip (SoC) a programmable logic unit, a microprocessor, or an application-specific integrated circuit (ASIC), etc. In some example embodiments, any of the memories, memory units, or the like as described herein may include a non-transitory computer readable storage device, for example a solid state drive (SSD), storing a program of instructions, and the one or more instances of processing circuitry may be configured to execute the program of instructions to implement the functionality of some or all of any of the processor 1120, memory 1130, motor 1030, engine 1040, or host/application 1050, or the like according to any of the example embodiments as described herein.

Hereinafter, some example embodiments are illustrated in more detail with reference to examples. However, the example embodiments are not limited to these examples.

SYNTHESIS EXAMPLES

Synthesis Example 1: Synthesis of Compound Represented by Chemical Formula 1-1

[Chemical Formula 1-1]

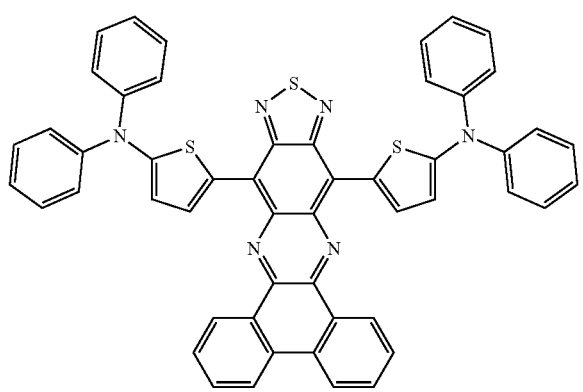

[Reaction Scheme 1-1]

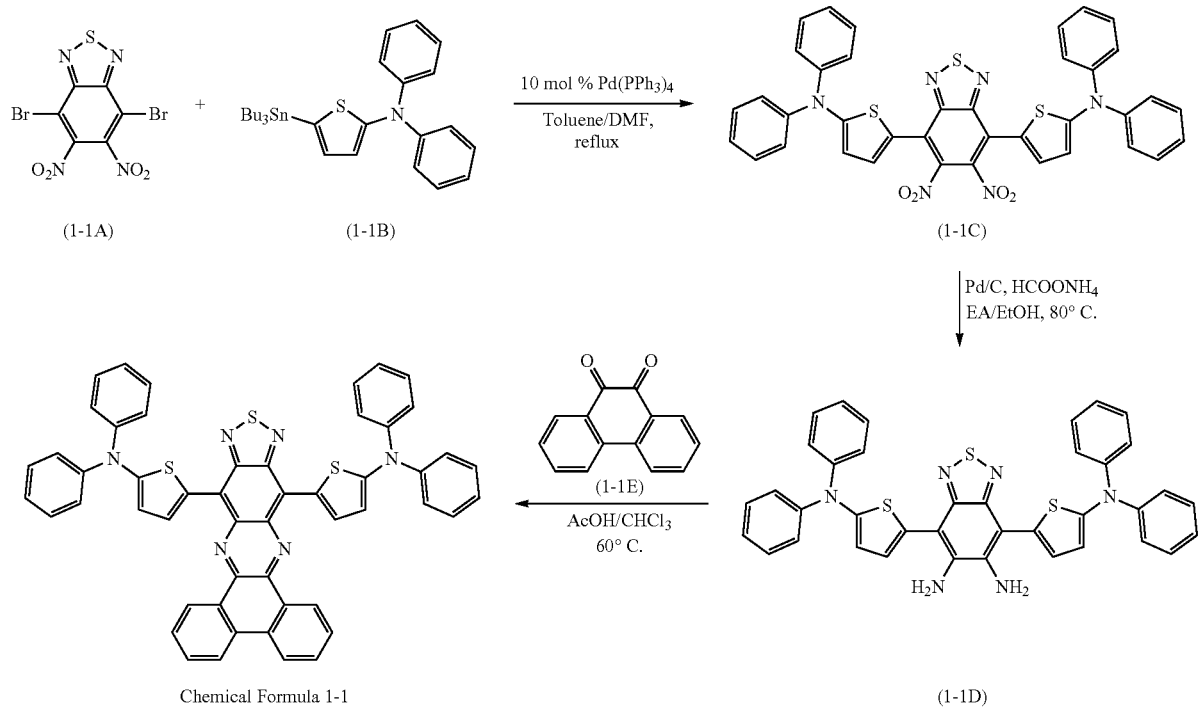

i) First Step: Synthesis of Compound (1-1C)

4,7-dibromo-5,6-dinitrobenzo[c][1,2,5]-thiadiazole (Compound (1-1A) (400 mg, 1.04 mmol) and N,N-diphenyl-5-(tributylstannyl)thiophen-2-amine (Compound (1-1B)) (1.4 g, 2.60 mmol) are dissolved in toluene (10 mL) and dimethyl formamide (DMF) (5 mL) in a round-bottomed flask under a nitrogen pressure, and tetrakis(triphenylphosphine)-palladium (0) (120 mg, 0.104 mmol) is added thereto. Subsequently, the obtained mixture is heated at 110° C. and then, refluxed and stirred for 12 hours. After cooling down the reactant to room temperature (24° C.), distilled water is added thereto. After performing an extraction with dichloromethane, an organic layer therefrom is dried by using MgSO₄. After filtering the MgSO₄, the reactant is concentrated to obtain Compound (1-1C).

UPLC-MS: [M+H]⁺ 725.07 ii) Second Step: Synthesis of Compound (1-1D)

Compound (1-1C) (15 mg, 0.02 mmol) is dissolved in ethyl acetate/ethanol (2 mL/2 mL) in a round-bottomed flask under a nitrogen pressure, and 10 wt % Pd/C (3 mg, 0.002 mmol) and ammonium formate (8 mg, 0.124 mmol) are added thereto. Subsequently, the obtained mixture is heated at 80° C. and stirred for 12 hours. The temperature of the reactant is cooled down to room temperature (24° C.) and passed through Celite to remove Pd/C. The filtrate is washed with ethyl acetate and then, concentrated. The concentrated resultant is dissolved in ethyl acetate and then, passed through Celite, and the filtrate is concentrated to obtain Compound (1-1 D).

UPLC-MS: [M+H]⁺ 664.96 iii) Third Step: Synthesis of Compound represented by Chemical Formula 1-1

Compound (1-1D) (13.7 mg, 0.02 mmol) is dissolved in acetic acid/chloroform (1 mL/2 mL) in a round-bottomed flask under a nitrogen pressure, and phenanthrene-9,10-dione (Compound (1-1E), 5.2 mg, 0.024 mmol) is added thereto and then, stirred at 60° C. for 12 hours. After adding distilled water to the reactant, a solid produced therein is filtered and sufficiently washed with hexane/ethyl acetate. The filtered solid is vacuum-dried to obtain 10 mg (Yield: 60%) of a compound represented by Chemical Formula 1-1.

UPLC-MS: [M+H]⁺ 837.22

Synthesis Example 2: Synthesis of Compound Represented by Chemical Formula 1-2

[Chemical Formula 1-2]

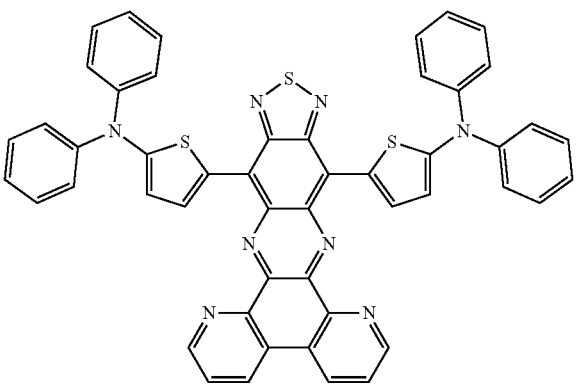

[Reaction Scheme 1-2]
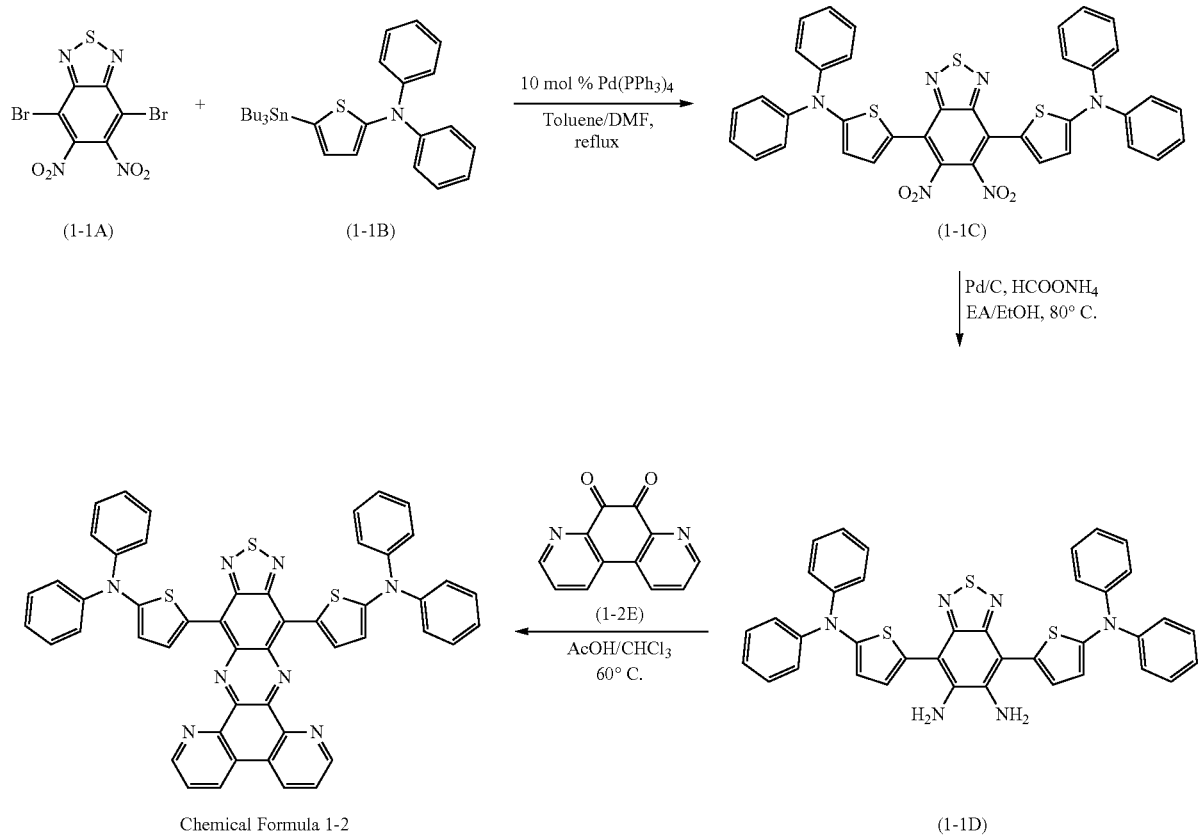
A compound represented by Chemical Formula 1-2 is synthesized according to the same method as Synthesis Example 1 except that 4,7-phenanthroline-5,6-dione (Compound (1-2E)) is used instead of Compound (1-1E) in the third step of Synthesis Example 1.
UPLC-MS: [M+H]+ 839.07
Synthesis Example 3: Synthesis of Compound Represented by Chemical Formula 1-3
[Chemical Formula 1-3]
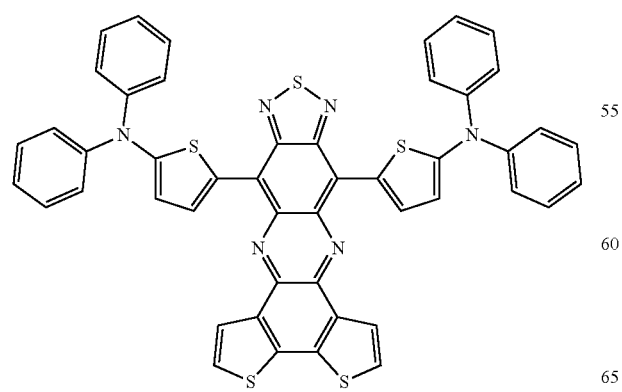

[Reaction Scheme 1-3]
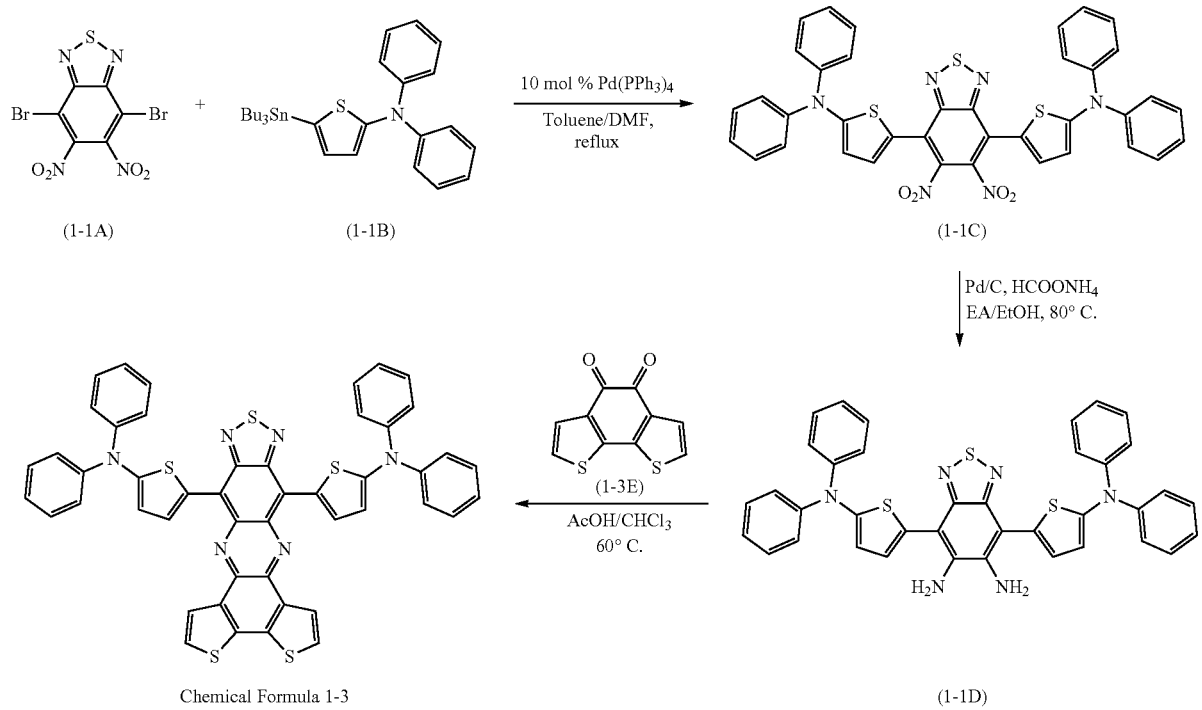
A compound represented by Chemical Formula 1-3 is synthesized according to the same method as Synthesis Example 1 except that benzo[1,2-b:4,3-b']dithiophene-4,5-dione (Compound (1-3E)) is used instead of Compound (1-1E) in the third step of Synthesis Example 1.
MALDI-TOF-MS: [M]⁺847.97:
Synthesis Example 4: Synthesis of Compound Represented by Chemical
Formula 1-4
[Chemical Formula 1-4]
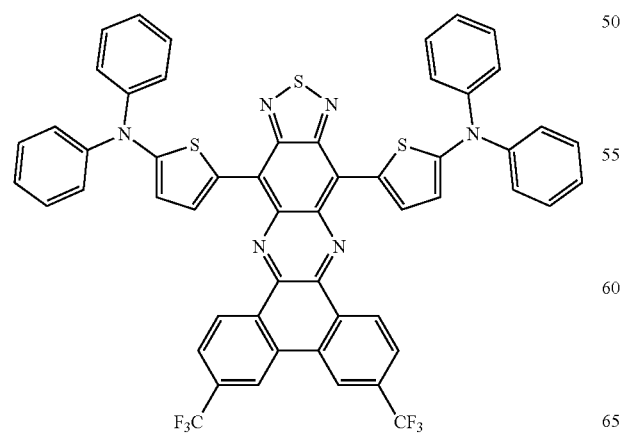

[Reaction Scheme 1-4]
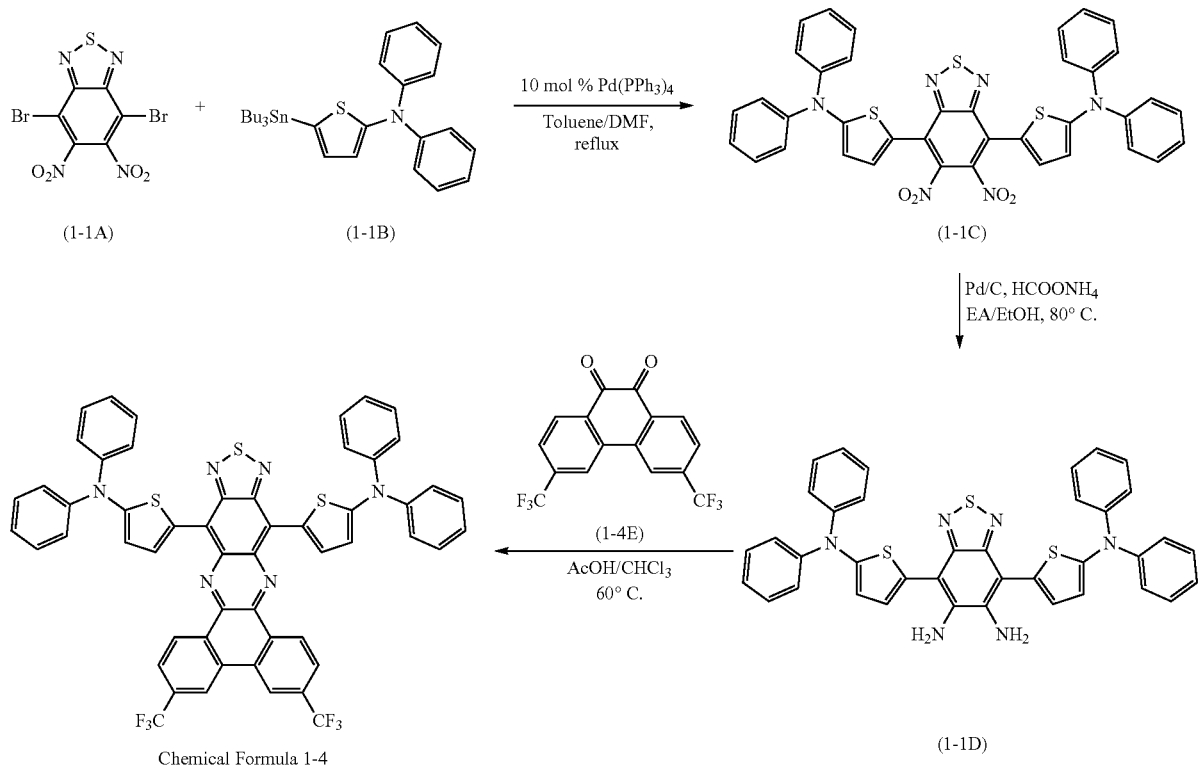
A compound represented by Chemical Formula 1-4 is synthesized according to the same method as Synthesis Example 1 except that 3,6-bis(trifluoromethyl)phenanthrene-9,10-dione (Compound (1-4E)) is used instead of Compound (1-1E) in the third step of Synthesis Example 1.
Synthesis Example 5: Synthesis of Compound Represented by Chemical Formula 1-5
[Chemical Formula 1-5]
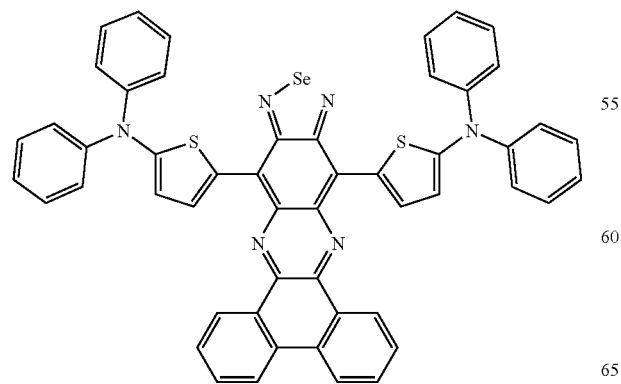

[Reaction Scheme 1-5]
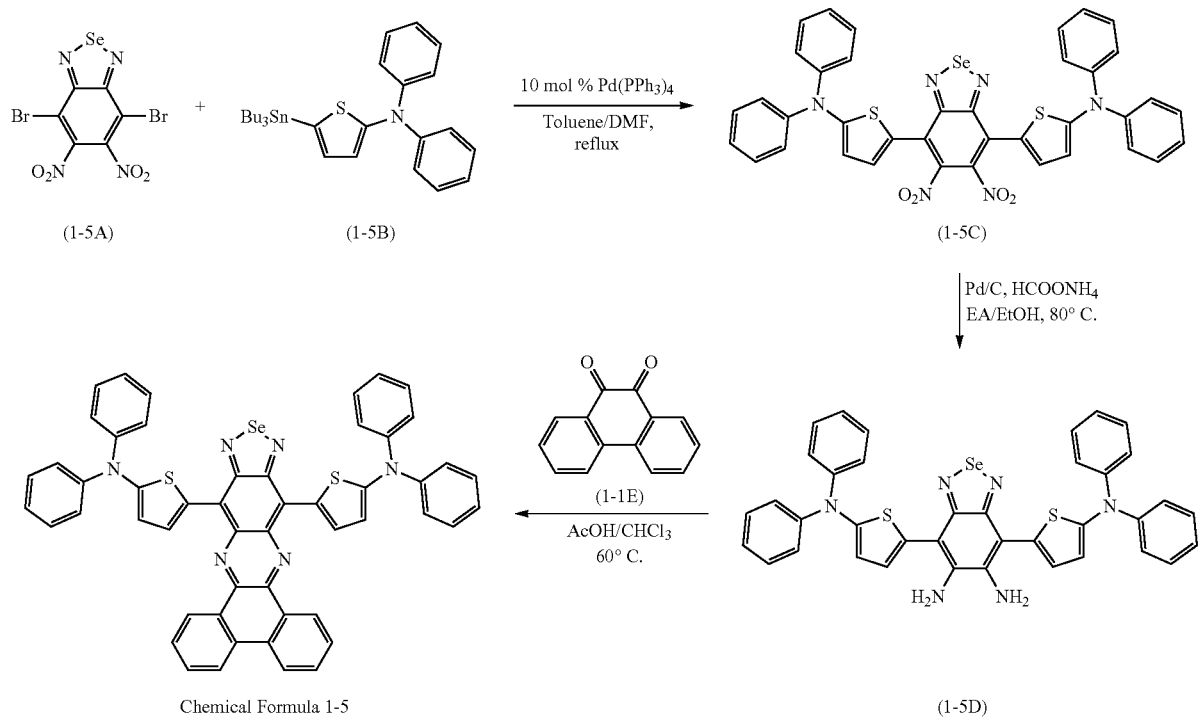
A compound represented by Chemical Formula 1-5 is synthesized according to the same method as Synthesis Example 1 except that 4,7-dibromo-5,6-dinitrobenzo[c][1,2,5]-selenadiazole (Compound (1-5A)) is used instead of Compound (1-1A) in the first step of Synthesis Example 1.
Synthesis Example 6: Synthesis of Compound Represented by Chemical Formula 1-6
[Chemical Formula 1-6]
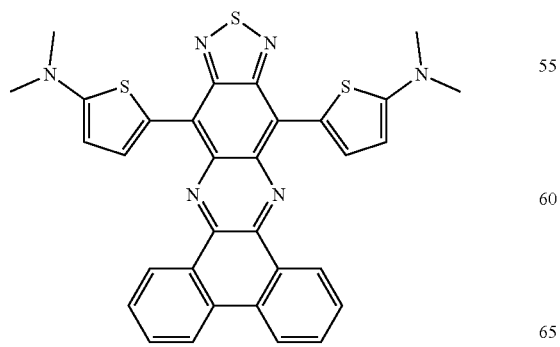

[Reaction Scheme 1-6]

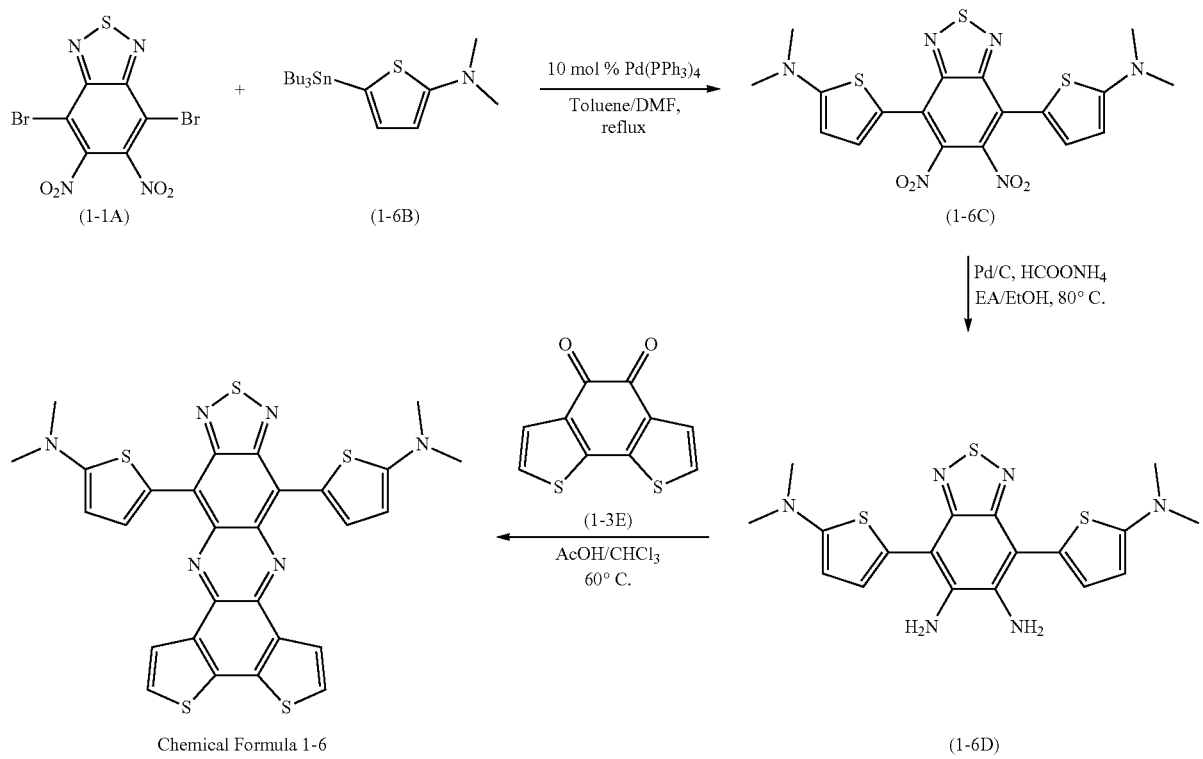

A compound represented by Chemical Formula 1-6 is synthesized according to the same method as Synthesis Example 1 except that N,N-dimethyl-5-(tributylstannyl)thiophen-2-amine (Compound (1-6B)) is used instead of Compound (1-1B) in the first step of Synthesis Example 1, and benzo[1,2-b:4,3-b']dithiophene-4,5-dione (Compound (1-3E)) is used instead of Compound (1-1E) in the third step of Synthesis Example 1.

Synthesis Example 7: Synthesis of Compound Represented by Chemical Formula 1-7

[Chemical Formula 1-7]

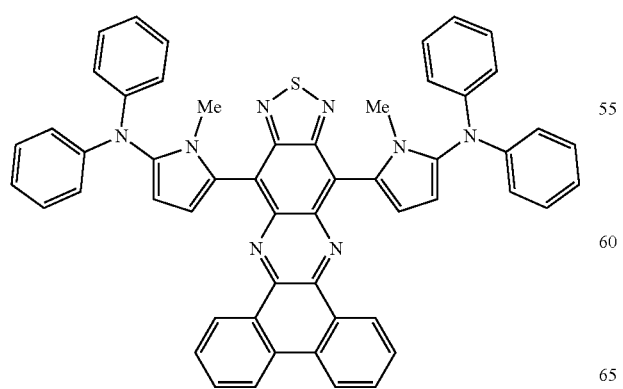

[Reaction Scheme 1-7]

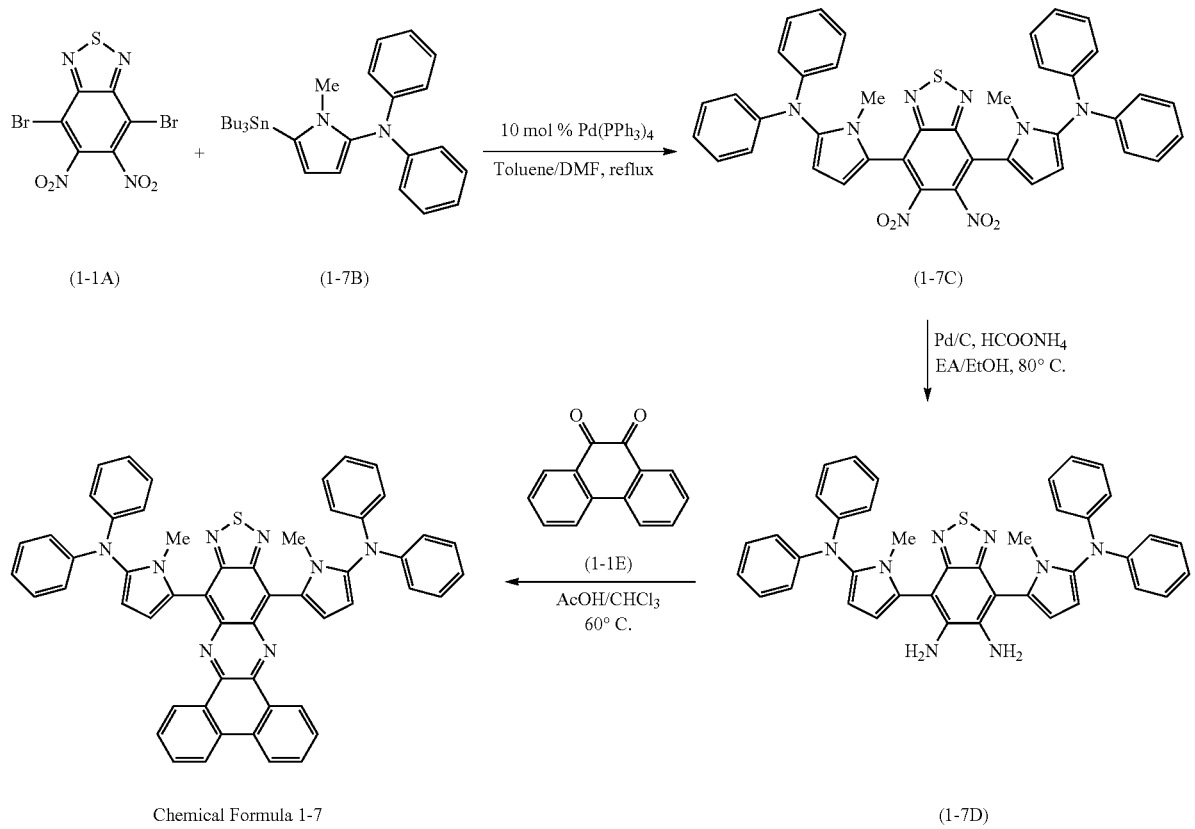

A compound represented by Chemical Formula 1-7 is synthesized according to the same method as Synthesis Example 1 except that 1-methyl-N,N-diphenyl-5-(tributyl-stannyl)-1H-pyrrol-2-amine (Compound (1-7B)) is used instead of Compound (1-1B) in the first step of Synthesis Example 1.

Synthesis Example 8: Synthesis of Compound Represented by Chemical Formula 1-8

[Chemical Formula 1-8]

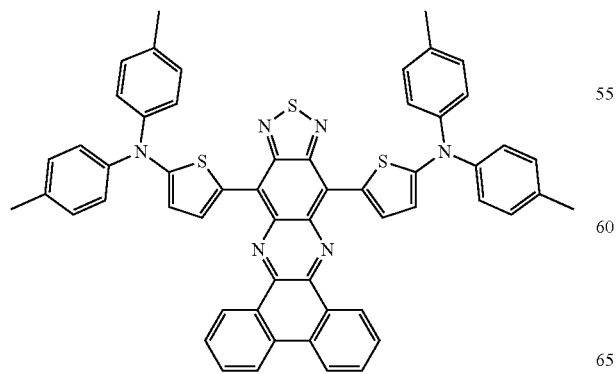

[Reaction Scheme 1-8]

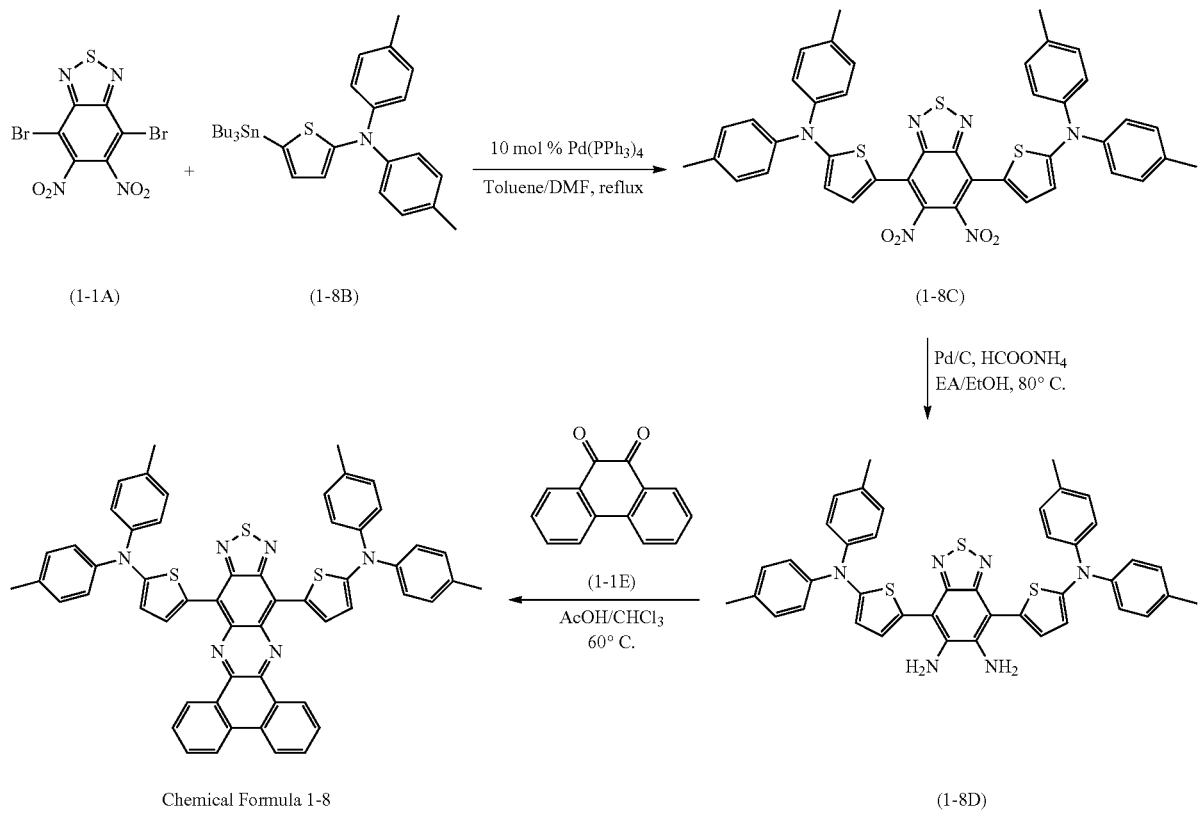

A compound represented by Chemical Formula 1-8 is synthesized according to the same method as Synthesis Example 1 except that N,N-di-p-tolyl-5-(tributylstannyl)thiophen-2-amine (Compound (1-8B)) is used instead of Compound (1-1B) in the first step of Synthesis Example 1.
UPLC-MS: [M+H]$^+$ 893.17

Synthesis Example 9: Synthesis of Compound Represented by Chemical Formula 1-9

[Chemical Formula 1-9]

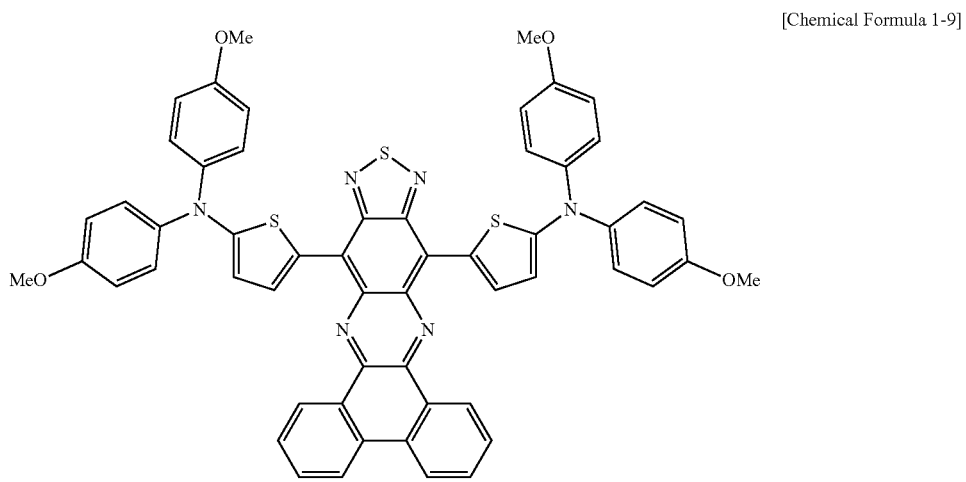 [SMILES: COc1ccc(N(c2ccc(OC)cc2)c2ccc(-c3c4nsnc4c(-c4ccc(N(c5ccc(OC)cc5)c5ccc(OC)cc5)s4)c4nc5c6ccccc6c6ccccc6c5nc34)s2)cc1]

[Reaction Scheme 1-9]

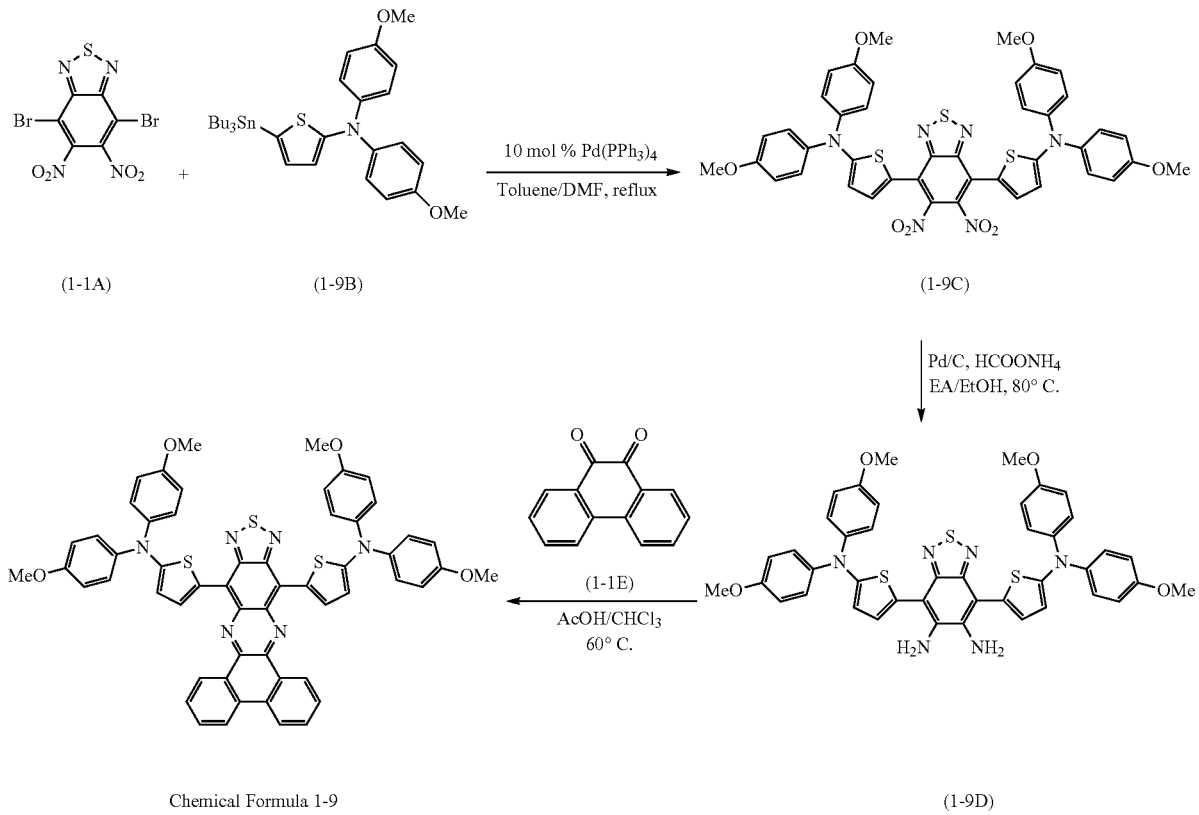

Chemical Formula 1-9            (1-9D)

A compound represented by Chemical Formula 1-9 is synthesized according to the same method as Synthesis Example 1 except that N,N-bis(4-methoxyphenyl)-5-(tributylstannyl)thiophen-2-amine (Compound (1-9B)) is used instead of Compound (1-1B).

UPLC-MS: [M+H]$^+$ 957.31

Comparative Synthesis Example 1: Synthesis of Compound Represented by Chemical Formula 2-1

A compound represented by Chemical Formula 2-1 is synthesized according to a method described in an article (D. Ma, Z. Y. Wang et al. J. Phys. Chem. C, 2009, 113, 1589 to 1595).

[Chemical Formula 2-1]

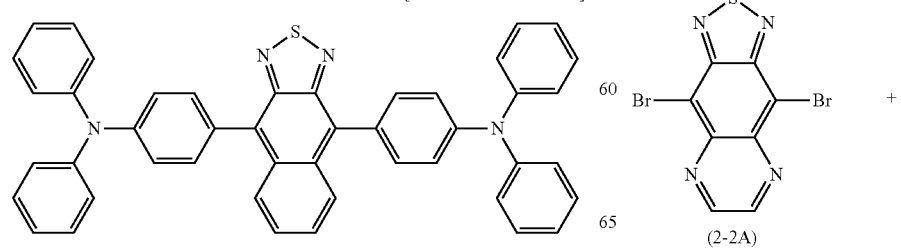

Comparative Synthesis Example 2: Synthesis of Compound Represented by Chemical Formula 2-2

[Chemical Formula 2-2]

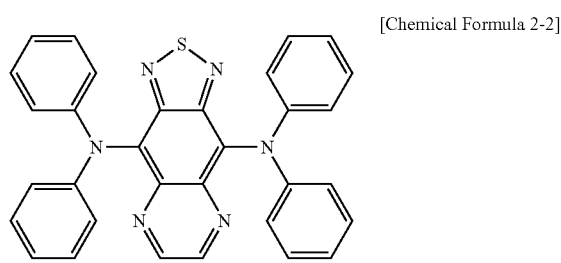 [SMILES: c1ccc(N(c2ccccc2)c2c3nccnc3c(N(c3ccccc3)c3ccccc3)c3nsnc23)cc1]

[Reaction Scheme 2-2]

-continued

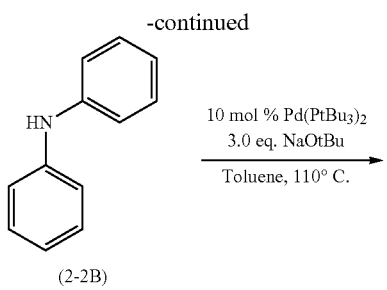

(2-2B)

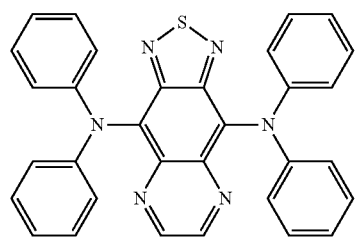

Chemical Formula 2-2

4,9-dibromo-[1,2,5]thiadiazolo[3,4-g]quinoxaline (Compound (2-3A)) (530 mg, 1.53 mmol), diphenylamine (Compound (2-3B)) (646 mg, 3.82 mmol), sodium tert-butoxide (317 mg, 4.59 mmol) are dissolved in toluene (10 mL) under a nitrogen pressure in a round-bottomed flask, and bis(tri-tert-butylphosphine)palladium (0) (78 mg, 0.153 mmol) is added thereto. Then, the mixture is heated at 110° C. and then, stirred and refluxed for 24 hours. After decreasing the temperature to room temperature (24° C.), the reactant is concentrated, and ethylacetate, distilled water, and an ammonium chloride aqueous solution are sequentially added thereto. The ethylacetate is used to extract an organic layer, and the organic layer is dried by using MgSO$_4$. After filtering the MgSO$_4$, a solution therefrom is concentrated and then, treated through silica chromatography. The purified material (Eluent: ethyl acetate:hexane=1:4) is vacuum-dried to obtain 120 mg (Yield: 15%) of a green solid.

$^1$H NMR (300 MHz, CD$_2$Cl$_2$): δ 8.57 (s, 2H), d 7.19 (d, 8H), d 7.06 (d, 8H), d 6.98 (t, 4H).

UPLC-MS: [M+H]$^+$ 523.14

Comparative Synthesis Example 3: Synthesis of Compound Represented by Chemical Formula 2-3

A compound represented by Chemical Formula 2-3 is synthesized in a method described in Scheme 1 of an article (ACS Nano, Highly Stable Organic Small Molecular Nanoparticles as an Advanced and Biocompatible Phototheranostic Agent of Tumor in Living Mice, 2017, 7177-7188).

[Chemical Formula 2-3]

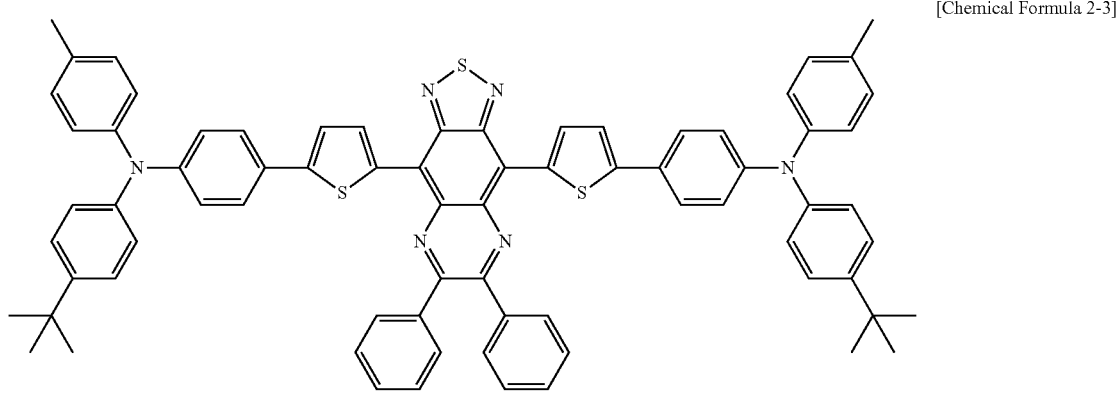 [SMILES: Cc1ccc(N(c2ccc(-c3ccc(-c4c5nsnc5c(-c5ccc(-c6ccc(N(c7ccc(C)cc7)c7ccc(C(C)(C)C)cc7)cc6)s5)c5nc(-c6ccccc6)c(-c6ccccc6)nc45)s3)cc2)c2ccc(C(C)(C)C)cc2)cc1]

Evaluation I: Light Absorption Characteristics

The compounds according to Synthesis Examples 1, 2, 3, 8, and 9 and Comparative Synthesis Examples 1 and 2 are respectively dissolved in a solvent at a concentration of $1 \times 10^{-5}$ M to prepare solutions, and light absorption characteristics of the compounds in a solution state are evaluated. The compounds of Synthesis Examples 1, 2, 8, and 9 and Comparative Synthesis Examples 1 and 2 use dichloromethane as a solvent, and the compound of Synthesis Example 3 uses chlorobenzene as a solvent. The results are shown in Table 1. The light absorption characteristics are evaluated by measuring a maximum absorption wavelength ($\lambda_{max}$) by using a UV-Vis-NIR spectrometer of Shimadzu UV-3600 Plus.

In addition, the compounds according to Synthesis Examples 1, 2, 8, and 9 and Comparative Synthesis Examples 1 and 2 are respectively spin-deposited on a glass substrate to evaluate light absorption characteristics in a thin film state. The light absorption characteristics are evaluated by measuring a maximum absorption wavelength ($\lambda_{max}$) with a UV-Vis-NIR spectrometer of Shimadzu UV-3600 Plus. The results are shown in Table 2.

On the other hand, DFT, TD-DFT (wB97X-D function with 6-311G(d,p) basis set) of the compounds of Synthesis Examples 4 to 6 and Comparative Synthesis Example 3 are calculated by using a Gaussian09 (G09) program assuming that the samples are toluene solutions. The results are shown in Table 3.

TABLE 1

|  | $\lambda_{max}$ (nm) (solution) |
| --- | --- |
| Synthesis Example 1 | 963 |
| Synthesis Example 2 | 1051 |
| Synthesis Example 3 | 1032 |
| Synthesis Example 8 | 1000 |
| Synthesis Example 9 | 1064 |
| Comparative Synthesis Example 1 | 594 |
| Comparative Synthesis Example 2 | 692 |

TABLE 2

|  | $\lambda_{max}$ (nm) (thin film) |
| --- | --- |
| Synthesis Example 1 | 1010 |
| Synthesis Example 2 | 1025 |
| Synthesis Example 8 | 1050 |
| Synthesis Example 9 | 1091 |
| Comparative Synthesis Example 1 | 623 |
| Comparative Synthesis Example 2 | 690 |

TABLE 3

|  | $\lambda_{max}$ (nm) (solution) |
| --- | --- |
| Synthesis Example 4 | 1028 |
| Synthesis Example 5 | 1023 |
| Synthesis Example 6 | 1053 |
| Comparative Synthesis Example 3 | 780 |

Referring to Tables 1 to 3, the compounds of Synthesis Examples 1 to 6, 8, and 9 exhibit satisfactory wavelength absorptions in a near-infrared wavelength region compared with the compounds of Comparative Synthesis Examples 1 to 3.

Evaluation II: Energy Level and Bandgap

The compounds of Synthesis Examples 1 to 9 and Comparative Synthesis Examples 1 to 3 are respectively deposited to form thin films, and HOMO energy level, LUMO energy level, and bandgap of each thin film are calculated in the Gaussian 09 program method by using B3LYP/6-31G(d) level theory described in [M. J. Frisch, et al., Gaussian 09, Revision D.01; Gaussian, Inc.: Wallingford, C T 2009]. The results of Synthesis Examples 1 to 9 and Comparative Synthesis Examples 1 and 2 are shown in Table 4.

TABLE 4

|  | HOMO (eV) | LUMO (eV) | Bandgap energy (eV) |
| --- | --- | --- | --- |
| Synthesis Example 1 | −4.60 | −3.31 | 1.29 eV |
| Synthesis Example 2 | −4.39 | −3.21 | 1.18 eV |
| Synthesis Example 3 | −4.52 | −3.32 | 1.20 eV |
| Synthesis Example 4 | −4.74 | −3.53 | 1.21 eV |
| Synthesis Example 5 | −4.55 | −3.34 | 1.21 eV |
| Synthesis Example 6 | −4.28 | −3.10 | 1.18 eV |
| Synthesis Example 8 | −4.46 | −3.22 | 1.24 eV |
| Synthesis Example 9 | −4.26 | −3.10 | 1.16 eV |
| Comparative Synthesis Example 1 | −5.26 | −3.70 | 1.56 eV |
| Comparative Synthesis Example 2 | −5.03 | −3.24 | 1.79 eV |

Referring to Table 4, the compounds of Synthesis Examples 1 to 9 have a smaller bandgap energy than the compounds of Comparative Synthesis Examples 1 and 2 and thus may effectively absorb light in a near-infrared wavelength region.

Evaluation III: Deposition Characteristics

Deposition characteristics of the compounds according to Synthesis Examples 1 to 9 and Comparative Synthesis Examples 1 to 3 are evaluated. The deposition characteristics is evaluated by using a thermogravimetric analysis method and sublimating the compounds under high vacuum of less than or equal to 10 Pa to measure weight losses. The result of Synthesis Example 1 is shown in Table 5.

TABLE 5

|  | $T_s$ (° C.) (−10 wt %) |
| --- | --- |
| Synthesis Example 1 | 331° C. |

* $T_s$ (° C.) (−10 wt %): a temperature that a weight of a sample is 10 wt % decreased Referring to Table 5, the compound of Synthesis Example 1 is depositable.

Example and Comparative Example: Production of Photoelectric Device

A 150 nm-thick anode is formed by sputtering ITO on a glass substrate. Subsequently, each compound according to Synthesis Examples 1 to 9 and Comparative Synthesis Examples 1 to 3 is co-deposited with C60 in a 1:1 volume ratio, respectively, to form a 150 nm-thick active layer (photoelectric conversion layer). Then, C60 is deposited on the photoelectric conversion layer to form an auxiliary layer. Then, ITO is sputtered on the auxiliary layer to form a 7 nm-thick cathode. Aluminum oxide ($Al_2O_3$) is deposited on the cathode to form a 50 nm-thick anti-reflection layer and encapsulated with a glass plate to produce the photoelectric devices according to Examples 1 to 9 and Comparative Examples 1 to 3.

Evaluation IV: Photoelectric Conversion Efficiency

Figure 14:
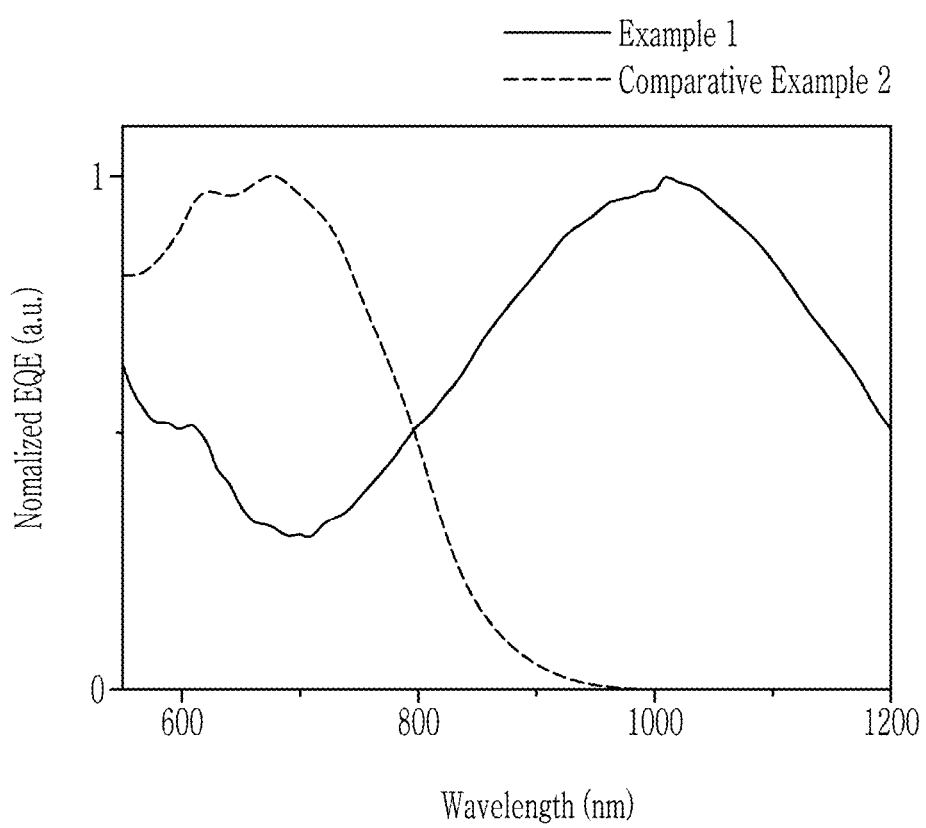
FIG. 14 is a graph showing external quantum efficiency of the photoelectric devices of Example 1 and Comparative Example 3.

Photoelectric conversion efficiency of the photoelectric devices according to Examples 1 to 9 and Comparative Examples 1 to 3 is evaluated. The photoelectric conversion efficiency is measured by using an IPCE measurement system (TNE Technology Co., Ltd., Korea). First, the system is calibrated by using a Si photodiode (Hamamatsu Photonics K.K., Japan) and then, mounted on a photoelectric device to measure the photoelectric conversion efficiency in a wavelength range of about 400 nm to about 1600 nm. The results of Example 1 and Comparative Example 2 are shown in FIG. 14. FIG. 14 is a graph showing external quantum efficiency of the photoelectric devices of Example 1 and Comparative Example 2.

Referring to FIG. 14, the photoelectric device of Example 1 exhibits excellent photoelectric conversion efficiency in a long wavelength region of about 1010 nm, compared with the photoelectric device of Comparative Example 2.

While this disclosure has been described in connection with what is presently considered to be practical example embodiments, it is to be understood that the inventive concepts are not limited to the disclosed example embodiments. On the contrary, the inventive concepts are intended to cover various modifications and equivalent arrangements included within the spirit and scope of the appended claims.

What is claimed is:

1. A near-infrared absorber, comprising:
a compound represented by Chemical Formula 1:

[Chemical Formula 1]

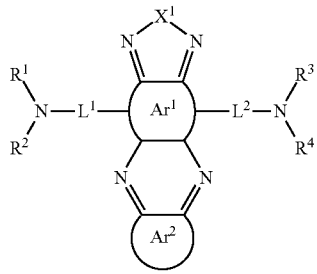

wherein, in Chemical Formula 1,
Ar$^1$ is a first moiety represented by Chemical Formula A-1, the first moiety including a first aromatic ring and left and right linking groups:

[Chemical Formula A-1]

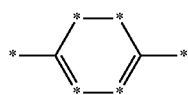

wherein, in Chemical Formula A-1,
separate adjacent pairs of *'s inside the first aromatic ring are linking portions with separate, respective ones of an N—X$^1$—N-containing pentagonal ring of Chemical Formula 1 and an N-containing hexagonal ring of Chemical Formula 1, and
*'s of the left and right linking groups are portions linked to separate, respective ones of L$^1$ and L$^2$ of Chemical Formula 1,
Ar$^2$ is a second moiety represented by Chemical Formula B-3b, the second moiety including a second aromatic ring:

[Chemical Formula B-3b]

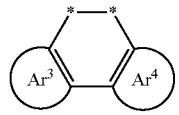

wherein, in Chemical Formula B-3b,
Ar$^3$ and Ar$^4$ are independently a substituted or unsubstituted C6 to C30 arene group or a substituted or unsubstituted C3 to C30 heteroarene group, and
*'s inside the second aromatic ring are linking portions with the N-containing hexagonal ring of Chemical Formula 1,
X$^1$ is O, S, Se, Te, S(=O), S(=O$_2$), NR$^a$, CR$^b$R$^c$, or SiR$^d$R$^e$, wherein R$^a$, R$^b$, R$^c$, and R$^d$ are independently hydrogen, a C1 to C6 alkyl group, a C1 to C6 haloalkyl group, a C6 to C12 aryl group, a C3 to C12 heteroaryl group, a halogen, a cyano group, or a combination thereof,
L$^1$ and L$^2$ are same or different and are each represented by Chemical Formula C-1:

[Chemical Formula C-1]

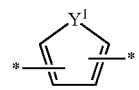

wherein, in Chemical Formula C-1,
Y$^1$ is O, S, Se, Te, S(=O), S(=O)$_2$, NR$^a$, or SiR$^b$R$^c$, wherein R$^a$, R$^b$, and R$^c$ are independently hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof,
R$^b$ and R$^c$ are independently present or linked to each other to form a ring, and
each * is a linking point with Chemical Formula 1,
R$^1$, R$^2$, R$^3$, and R$^4$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C3 to C30 heteroaryl group, a substituted or unsubstituted silyl group, a halogen, or a combination thereof, and
R$^1$ and R$^2$ are independently present or linked to each other to form a ring, and R$^3$ and R$^4$ are independently present or linked to each other to form a separate ring.

2. The near-infrared absorber of claim 1, wherein the second moiety represented by Chemical Formula B-3b is represented by Chemical Formula B-3bb, each moiety including at least one aromatic ring:

[Chemical Formula B-3bb]

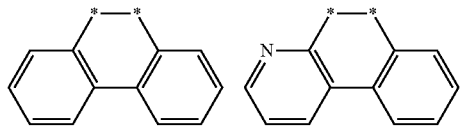

-continued

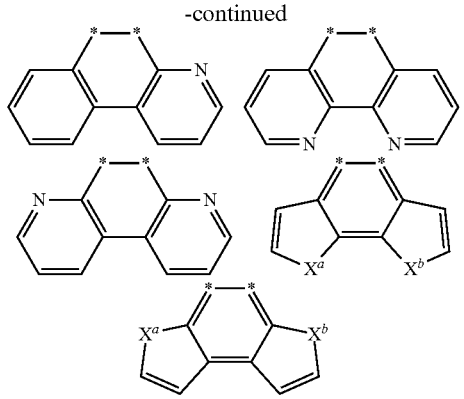

wherein, in Chemical Formula B-3bb,
hydrogen of each aromatic ring is present or is replaced by a halogen, a cyano group, a C1 to C10 alkyl group, a C1 to C10 haloalkyl group, —SiH$_3$, a C1 to C10 alkylsilyl group, a C6 to C20 aryl group, or a C3 to C20 heteroaryl group,
*'s inside the at least one aromatic ring are linking portions with an N-containing hexagonal ring of Chemical Formula 1, and
$X^a$ and $X^b$ are independently —O—, —S—, —Se—, —Te—, —NR$^a$—, —SiR$^b$R$^c$—, or —GeR$^d$R$^e$—, wherein R$^a$, R$^b$, R$^c$, R$^d$, and R$^e$ are independently hydrogen, a halogen, a substituted or unsubstituted C1 to C10 alkyl group, or a substituted or unsubstituted C6 to C10 aryl group.

3. The near-infrared absorber of claim 1, wherein in Chemical Formula 1, *—N(R$^1$)(R$^2$) and *—N(R$^3$)(R$^4$) are independently represented by Chemical Formula D-1 or Chemical Formula D-2:

[Chemical Formula D-1]

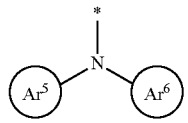

[Chemical Formula D-2]

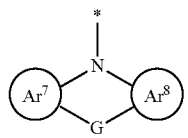

wherein, in Chemical Formula D-1,
Ar$^5$ and Ar$^6$ are independently a substituted or unsubstituted C6 to C30 aryl group or a substituted or unsubstituted C3 to C30 heteroaryl group, and
* is a linking point with Chemical Formula 1,
wherein, in Chemical Formula D-2,
Ar$^7$ and Ar$^8$ are independently a substituted or unsubstituted C6 to C30 arene group or a substituted or unsubstituted C3 to C30 heteroarene group,
G is a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ are independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a ring, and
n of —(CR$^f$R$^g$)$_n$— is an integer of 1 or 2, and
* is a linking point with Chemical Formula 1.

4. The near-infrared absorber of claim 3, wherein Chemical Formula D-1 is represented by Chemical Formula D-1a or D-1b:

[Chemical Formula D-1a]

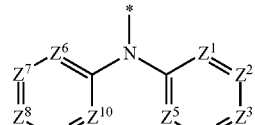

[Chemical Formula D-1b]

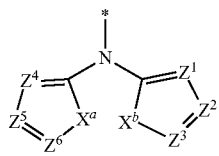

wherein, in Chemical Formula D-1a,
$Z^1$ to $Z^{10}$ are independently N or CR$^a$, wherein R$^a$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof,
when $Z^1$ to $Z^{10}$ are CR$^x$, R$^x$'s are independently present or two adjacent groups of $Z^1$ to $Z^{10}$ are linked to each other to form a 5-membered aromatic ring or a 6-membered aromatic ring, and
* is a linking point with Chemical Formula 1,
wherein, in Chemical Formula D-1b,
$X^a$ and $X^b$ are independently —O—, —S—, —Se—, —Te—, —NR$^a$—, —SiR$^b$R$^c$—, or —GeR$^d$R$^e$—, wherein R$^a$, R$^b$, R$^c$, R$^d$, and R$^e$ are independently hydrogen, a halogen, a substituted or unsubstituted C1 to C10 alkyl group, or a substituted or unsubstituted C6 to C10 aryl group,
$Z^1$ to $Z^6$ are independently N or CR$^x$, wherein R$^x$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof,
when $Z^1$ to $Z^6$ are CR$^x$, R$^x$'s are independently present or two adjacent groups of $Z^1$ to $Z^6$ are linked to each other to form a 5-membered aromatic ring or a 6-membered aromatic ring, and
* is a linking point with Chemical Formula 1.

5. The near-infrared absorber of claim 3, wherein Chemical Formula D-2 is represented by Chemical Formula D-2a, Chemical Formula D-2b, or Chemical Formula D-2c:

[Chemical Formula D-2a]

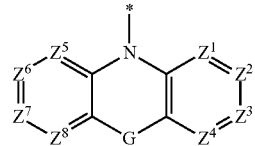

-continued

[Chemical Formula D-2b]

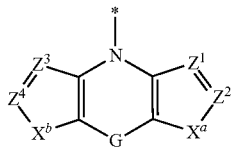

[Chemical Formula D-2c]

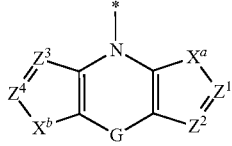

wherein, in Chemical Formula D-2a,
G is a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ are independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a ring, and n of —(CR$^f$R$^g$)$_n$— is an integer of 1 or 2, $Z^1$ to $Z^8$ are independently N or CR$^x$, wherein R$^x$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof, when $Z^1$ to $Z^8$ are CR$^x$, R$^x$ may independently be present or two adjacent groups of $Z^1$ to $Z^8$ may be linked to each other to form a 5-membered aromatic ring or a 6-membered aromatic ring, and

*is a linking point with Chemical Formula 1, wherein, in Chemical Formula D-2b and Chemical Formula D-2c,
G is a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ are independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a ring, and n of —(CR$^f$R$^g$)$_n$— is an integer of 1 or 2, $X^a$ and $X^b$ are independently —O—, —S—, —Se—, —Te—, —NR$^p$—, —SiR$^q$R$^r$— or —GeR$^s$R$^t$—, wherein R$^p$, R$^q$, R$^r$, R$^s$, and R$^t$ are independently hydrogen, a halogen, a substituted or unsubstituted C1 to C10 alkyl group, or a substituted or unsubstituted C6 to C10 aryl group, $Z^1$ to $Z^4$ are independently N or CR$^x$ (wherein R$^x$ is hydrogen, a C1 to C6 alkyl group, a C1 to C10 haloalkyl group, —SiH$_3$, a C1 to C10 alkylsilyl group, —NH$_2$, a C1 to C10 alkylamine group, a C6 to C12 aryl group, a C3 to C12 heteroaryl group, a halogen, a cyano group, or a combination thereof).

6. The near-infrared absorber of claim 1, wherein the near-infrared absorber has a peak absorption wavelength in a wavelength region of about 750 nm to about 3000 nm.

7. A near-infrared absorbing/blocking film comprising the near-infrared absorber of claim 1.

8. A photoelectric device, comprising:
a first electrode and a second electrode facing each other; and
an active layer between the first electrode and the second electrode,
wherein the active layer includes the near-infrared absorber of claim 1 that includes the compound represented by Chemical Formula 1.

9. The photoelectric device of claim 8, wherein in Chemical Formula 1, *—N(R$^1$)(R$^2$) and *—N(R$^3$)(R$^4$) are independently represented by Chemical Formula D-1 or Chemical Formula D-2:

[Chemical Formula D-1]

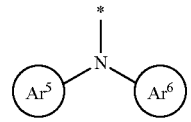

[Chemical Formula D-2]

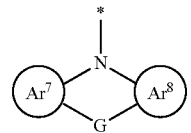

wherein, in Chemical Formula D-1,
Ar$^5$ and Ar$^6$ are independently a substituted or unsubstituted C6 to C30 aryl group or a substituted or unsubstituted C3 to C30 heteroaryl group, and
* is a linking point with Chemical Formula 1,
wherein, in Chemical Formula D-2,
Ar$^7$ and Ar$^8$ are independently a substituted or unsubstituted C6 to C30 arene group or a substituted or unsubstituted C3 to C30 heteroarene group,
G is a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ are independently hydrogen, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a ring, and n of —(CR$^f$R$^g$)$_n$— is an integer of 1 or 2, and
* is a linking point with Chemical Formula 1.

10. The photoelectric device of claim 8, wherein the active layer further includes fullerene.

11. The photoelectric device of claim 8, wherein the active layer has a peak absorption wavelength in a wavelength region of about 750 nm to about 3000 nm.

12. An organic sensor comprising the photoelectric device of claim 8.

13. An electronic device comprising the organic sensor of claim 12.

14. An electronic device comprising the photoelectric device of claim 8.

15. A photoelectric device, comprising:
a first electrode and a second electrode facing each other;
an active layer between the first electrode and the second electrode; and a charge auxiliary layer between
the active layer and the first electrode, or
the active layer and the second electrode,
wherein the charge auxiliary layer includes the near-infrared absorber of claim 1 that includes the compound represented by Chemical Formula 1.

16. The photoelectric device of claim 15, wherein the active layer further includes the near-infrared absorber.

17. An organic sensor, comprising:
a semiconductor substrate;
a first photoelectric device on the semiconductor substrate, the first photoelectric device configured to selectively absorb light in a first near-infrared wavelength region; and
an additional sensor configured to selectively absorb light in a separate wavelength region that is different from the first near-infrared wavelength region,
wherein the first photoelectric device includes the near-infrared absorber of claim 1 that includes the compound represented by Chemical Formula 1.

18. The organic sensor of claim 17, wherein
the additional sensor is an infrared light sensor at least partially embedded within the semiconductor substrate, and the separate wavelength region is a separate near-infrared wavelength region that is different from the first near-infrared wavelength region, and
the first photoelectric device and the infrared light sensor overlap in a vertical direction that is perpendicular to a top surface of the semiconductor substrate.

19. The organic sensor of claim 17, wherein
the additional sensor includes a plurality of photodiodes at least partially embedded within the semiconductor substrate, the plurality of photodiodes configured to selectively absorb light in separate visible wavelength regions, and
the first photoelectric device and the plurality of photodiodes overlap in a vertical direction that is perpendicular to a top surface of the semiconductor substrate.

20. The organic sensor of claim 19, further comprising:
an additional photoelectric device on the semiconductor substrate, the additional photoelectric device being between the first photoelectric device and the semiconductor substrate, the additional photoelectric device configured to selectively absorb light in an additional wavelength region that is different from the first near-infrared wavelength region and the separate visible wavelength regions.

21. The organic sensor of claim 17, wherein
the additional sensor includes at least one additional photoelectric device vertically stacked between the first photoelectric device and the semiconductor substrate, each separate photoelectric device of the at least one additional photoelectric device including a separate photoelectric conversion layer and configured to selectively absorb light in a respective wavelength region that is different from the first near-infrared wavelength region.

22. The organic sensor of claim 17, wherein the first photoelectric device includes
a first electrode and a second electrode facing each other; and
an active layer between the first electrode and the second electrode, wherein the active layer includes the near-infrared absorber.

23. The organic sensor of claim 17, wherein the first photoelectric device includes
a first electrode and a second electrode facing each other;
an active layer between the first electrode and the second electrode; and
a charge auxiliary layer between
the active layer and the first electrode, or
the active layer and the second electrode,
wherein the charge auxiliary layer includes the near-infrared absorber.

* * * * *